US011504327B1

(12) United States Patent
Morrison

(10) Patent No.: US 11,504,327 B1
(45) Date of Patent: Nov. 22, 2022

(54) METHOD OF PREPARING NANOPARTICLES BY HOT-MELT EXTRUSION

(71) Applicant: Eric Morrison, West Saint Paul, MN (US)

(72) Inventor: Eric Morrison, West Saint Paul, MN (US)

(*) Notice: Subject to any disclaimer, the term of this patent is extended or adjusted under 35 U.S.C. 154(b) by 133 days.

(21) Appl. No.: 16/748,399

(22) Filed: Jan. 21, 2020

Related U.S. Application Data

(60) Provisional application No. 62/794,742, filed on Jan. 21, 2019, provisional application No. 62/843,763, filed on May 6, 2019.

(51) Int. Cl.
| | | |
|---|---|---|
| *A61K 9/107* | (2006.01) | |
| *A61K 9/00* | (2006.01) | |
| *A61K 31/192* | (2006.01) | |
| *A61K 47/26* | (2006.01) | |
| *A61K 47/44* | (2017.01) | |
| *A61K 47/34* | (2017.01) | |
| *A61K 47/24* | (2006.01) | |
| *A61K 47/14* | (2017.01) | |
| *A61K 47/06* | (2006.01) | |
| *A61K 47/08* | (2006.01) | |

(52) U.S. Cl.
CPC .......... *A61K 9/1075* (2013.01); *A61K 9/0014* (2013.01); *A61K 31/192* (2013.01); *A61K 47/06* (2013.01); *A61K 47/08* (2013.01); *A61K 47/14* (2013.01); *A61K 47/24* (2013.01); *A61K 47/26* (2013.01); *A61K 47/34* (2013.01); *A61K 47/44* (2013.01)

(58) Field of Classification Search
CPC .. A61K 9/1075; A61K 9/0014; A61K 31/192; A61K 47/06; A61K 47/08; A61K 47/14; A61K 47/24; A61K 47/26; A61K 47/34; A61K 47/44
See application file for complete search history.

(56) References Cited

U.S. PATENT DOCUMENTS

| | | | |
|---|---|---|---|
| 5,713,209 | A | 2/1998 | Hunchar et al. |
| 6,207,213 | B1 | 3/2001 | Groux et al. |
| 6,221,370 | B1 | 4/2001 | Wadle et al. |
| 6,391,322 | B1 | 5/2002 | Roulier et al. |
| 7,385,001 | B2 | 6/2008 | Shim et al. |
| 8,394,441 | B2 | 3/2013 | Windhab et al. |
| 9,005,666 | B2 | 4/2015 | Saulnier et al. |
| 9,526,682 | B2 | 12/2016 | Sebillotte-Amaud et al. |
| 10,098,892 | B2 | 10/2018 | Harmon et al. |
| 2010/0068307 | A1* | 3/2010 | Nielloud ............ A61K 9/0014 424/702 |
| 2010/0137443 | A1 | 6/2010 | Carter et al. |
| 2011/0135734 | A1 | 6/2011 | Magdassi et al. |
| 2012/0232147 | A1 | 9/2012 | Hustved et al. |
| 2016/0317416 | A1 | 11/2016 | Derripe et al. |
| 2017/0087064 | A1 | 3/2017 | Ikedi et al. |
| 2017/0296496 | A1* | 10/2017 | Morrison ............ A61K 9/0014 |
| 2017/0319486 | A1 | 11/2017 | Upadhye et al. |
| 2018/0250248 | A1* | 9/2018 | Ray, II ................. A61K 31/17 |

FOREIGN PATENT DOCUMENTS

EP 0605497 9/1992

OTHER PUBLICATIONS

Bhagurkar A, Repka M, Murthy S. A Novel Approach for the Development of a Nanostructured Lipid Carrier Formulation by Hot-Melt Extrusion Technology. J Pharm Sci. Apr. 2017;106(4):1085-1091. doi: 10.1016/j.xphs.2016.12.015. Epub Dec. 28, 2016.

Bhagurkar A, Angamuthu M, Patil H, Tiwari RV, Maurya A, Hashemnejad S, Kundu S, Murthy S, Repka M. Development of an Ointment Formulation Using Hot-Melt Extrusion Technology. AAPS PharmSciTech. Feb. 2016;17(1):158-66. doi: 10.1208/s12249-015-0453-3. Epub Dec. 1, 2015.

Lang B, McGinity J, Williams R Hot-melt extrusion—basic principles and pharmaceutical applications. Drug Dev Ind Pharm. Sep. 2014;40(9):1133-55. doi: 10.3109/03639045.2013.838577. Epub Feb. 13, 2014.

Lawton D. A Thesis for the Degree of Master of Applied Science McMaster University Aug. 2013 available at https://macsphere.mcmaster.ca/bitstream/11375/15278/1/fulltext.pdf.

Patil H, Kulkarni V, Majumdar S, Repka M. Continuous manufacturing of solid lipid nanoparticles by hot melt extrusion. Int J Pharm. Aug. 25, 2014;471(1-2):153-6. doi: 10.1016/j.ijpharm.2014.05.024. Epub May 20, 2014.

Djuric D. Continuous Granulation with a Twin-Screw Extruder Cuvillier Verlag publications, available at: https://pdfs.semanticscholar.org/21f5/6a28aa118b223fbd3d3cce9d4bd0b1cd42c.pdf.

Ozgun S. Nanoemulsions in Cosmetics Nanomaterials and Nanotechnology Lecture Project Technical Report—Jan. 2013 available at: https://www.researchgate.net/publication/235890223_Nanoemulsions_in_Cosmetics.

Kunieda et al., Highly Concentrated Cubic-Phase Emulsions: Basic Study on D-Phase Emulsification using Isotropic Gels. J Oleo Sci 50(8):633-639 • Jan. 2001.

Spiering et al., Changes in Phase Behavior from the Substitution of Ethylene Oxide with Carbon Dioxide in the Head Group of Nonionic Surfactants. ChemSusChem. Nov. 25, 2019, doi: 10.1002/cssc.201902855. [Epub ahead of print]).

Gvaramia et al., Capillary condensation and gelling of microemulsions with clay Additives, Journal of Colloid and Interface Science 525 (2018) 161-165.

Müller et al. (Solid lipid nanoparticles (SLN) and nanostructured lipid carriers (NLC) in cosmetic and dermatological preparations Adv. Drug Deliv. Rev., 54 Suppl. 1 (2002) S131-S155).

Puglia et al., Lipid nanoparticles as novel delivery systems for cosmetics and dermal pharmaceuticals Expert Opin. Drug Deliv. 9 (2012) 429-441. doi:10.1517/17425247.2012.666967.

(Continued)

*Primary Examiner* — Genevieve S Alley
(74) *Attorney, Agent, or Firm* — Merchant & Gould P.C.

(57) ABSTRACT

The present invention provides a nanoparticle dispersion for topical delivery to skin of a mammal. The nanoparticle dispersion includes: one or more hydrophobic bioactive agents or one or more hydrophobic drugs; one or more surfactants; one or more water immiscible oils; and water. Methods of preparing nanoparticle dispersions by hot melt extrusion are also provided.

17 Claims, 7 Drawing Sheets

(56) References Cited

OTHER PUBLICATIONS

Montenegro et al., From nanoemulsions to nanostructured lipid carriers: A relevant development in dermal delivery of drugs and cosmetics J Drug Deliv Sci Technol vol. 32, Part B, Apr. 2016, pp. 100-112 https://doi.org/10.1016/i.jddst.2015.10.003.

Heurtault et al., A Novel Phase Inversion-Based Process for the Preparation of Lipid Nanocarriers, Pharm. Res. 19, 875, 2002.

Anton et al., Nano-emulsions and nanocapsules by the PIT method: An investigation on the role of the temperature cycling on the emulsion phase inversion Int J Pharm. Nov. 1, 2007;344(1-2):44-52.

Walters et al., The effects of surfactants on penetration across the skin Int J Cosmet Sci. Dec. 1993; 15(6):260-71.

Park et al., Enhancing effect of polyoxyethylene alkyl ethers on the skin permeation of ibuprofen Int J Pharm. Nov. 19, 2000;209(1-2):109-19.

Wu et al., Structural properties of paeonol encapsulated iposomes at physiological temperature:Synchrotron small-angle and wide-angle X-ray diffraction studies, Biomedical Spectroscopy and Imaging 5 (2016) S45-S54.

Lee et al., Cryogenic Electron Microscopy Study of Nanoemulsion Formation from Microemulsions, Langmuir 2014, 30, 36, 10826-10833.

Abdel-Mottaleb et al., Lipid nanocapsules for dermal application: A comparative study of lipid-based versus polymer-based nanocarriers, European Journal of Pharmaceutics and Biopharmaceutics 79 (2011) 36-42.

Nounoua et al., Liposomal Formulation for Dermal and Transdermal Drug Delivery: Past, Present and Future, Recent Patents on Drug Delivery & Formulation 2008, 2, 9-18.

\* cited by examiner

METHOD OF PREPARING NANOPARTICLES BY HOT-MELT EXTRUSION

RELATED APPLICATIONS

This application claims priority to U.S. Provisional Patent Application Ser. No. 62/843,763 filed May 6, 2019, 2019, and claims priority to U.S. Provisional Patent Application Ser. No. 62/794,742 fled Jan. 21, 2019, al of which are hereby incorporated by reference in their entirety for all purposes.

BACKGROUND OF THE INVENTION

It is often the case that poorly water-soluble pharmacological compounds are difficult to administer to living organisms in an effective manner because of one or more problems including poor bioavailability, too rapid decomposition and excretion, which creates a need for frequent re-dosing, and irritation or tissue damage at the location of introduction.

The bioavailability of poorly water soluble, orally administered drug is a major challenge for the pharmaceutical industry as many newly launched drugs possess low aqueous solubility, which leads to poor dissolution and low absorption. Furthermore, poor solubility results in variability in absorption and lack of dose proportionality. Compounding the problems of poor absorption is the problem that pharmacologically useful compounds may be substantially degraded in the gastrointestinal tract before absorption can occur. Solutions have been proposed including Self-Emulsifying Drug Delivery Systems (SEDDS's), defined as isotropic mixtures of one or more hydrophilic solvents and co-solvents/surfactants that are capable to form fine oil-in-water (o/w) emulsions upon mild agitation and dilution in gastrointestinal fluids, and various types of emulsions or suspensions.

What is needed is a method for making nanoparticle dispersions of hydrophobic drugs and hydrophobic bioactive and compositions thereof.

SUMMARY OF THE INVENTION

The present invention provides a nanoparticle dispersion for topical delivery to skin of a mammal. The nanoparticle dispersion includes: one or more hydrophobic bioactive agents or one or more hydrophobic drugs; one or more surfactants; one or more water immiscible oils; and water. Methods of preparing nanoparticle dispersions by hot melt extrusion are also provided.

The present invention provides a process for preparing a nanoparticle dispersion including providing a composition with one or more polyethoxylated high hydrophile-lipophile-balance (HLB) surfactants, one or more low hydrophile-lipophile-balance (HLB) surfactants, one or more water immiscible oils, and water with between about 25 and about 60 percent lipophilic content, conveying the composition through a twin screw extruder modified so as to provide the composition with a temperature change of greater than about 35° C. and a final temperature of less than about 30° C., wherein the composition forms a lamellar microemulsion between about 75° C. and 100° C. The invention provides concentrated nanoparticle dispersions that are useful for topical delivery of hydrophobic drugs and hydrophobic bioactive agents in a single step continuous process. As used herein, lipophilic content means the sum of the concentrations of surfactants, water immiscible oils, hydrophobic drugs, and hydrophobic bioactive agents.

The present invention provides a nanoparticle dispersion for topical delivery to skin of a mammal. The nanoparticle dispersion includes: one or more hydrophobic drugs each independently having a log P>1; one or more polyethoxylated high hydrophile-lipophile-balance (HLB) surfactants; one or more low hydrophile-lipophile-balance (HLB) surfactants each independently having a hydrophile-lipophile-balance (HLB) value less than about 10; one or more water immiscible oils; and water.

In one embodiment, the one or more hydrophobic drugs each independently having a log P>1 do not form crystals from the nanoparticle dispersion for greater than about 8 months at a temperature from about 18° C. to about 22° C. In one embodiment, the one or more hydrophobic drugs are selected from the group consisting of aspirin, benzocaine, hydrocortisone, ibuprofen, and lidocaine. In one embodiment, the composition with one or more hydrophobic drugs is free of ibuprofen and S-ibuprofen. In one embodiment, the one or more polyethoxylated high hydrophile-lipophile-balance (HLB) surfactants include one or more ether type polyethoxylated high hydrophile-lipophile-balance (HLB) surfactants each independently having a hydrophile-lipophile-balance (HLB) value of equal to or greater than about 14. In one embodiment, the one or more polyethoxylated high hydrophile-lipophile-balance (HLB) surfactants include one or more ester type polyethoxylated high hydrophile-lipophile-balance (HLB) surfactants each independently having a hydrophile-lipophile-balance (HLB) value of equal to or greater than about 14. In one embodiment, the one or more polyethoxylated high hydrophile-lipophile-balance (HLB) surfactants include one or more ether type polyethoxylated high hydrophile-lipophile-balance (HLB) surfactants each independently having a hydrophile-lipophile-balance (HLB) value of equal to or greater than about 14 and one or more ester type polyethoxylated high hydrophile-lipophile-balance (HLB) surfactants each independently having a hydrophile-lipophile-balance (HLB) value of equal to or greater than about 14.

In one embodiment, the nanoparticle dispersion has a weight square mean deviation value of hydrophile-lipophile-balance (HLB) (WMSD$_{HLB}$) between about 1.5 and about 4.5. In one embodiment, the nanoparticle dispersion has volume average particle size less than about 150 nm. In one embodiment, the nanoparticle dispersion has a latent lamellar structure. In one embodiment, the nanoparticle dispersion is edible.

In one embodiment, the nanoparticle dispersion further includes one or more non-polyethoxylated high hydrophile-lipophile-balance (HLB) surfactants each independently having a hydrophile-lipophile-balance (HLB) value of equal to or greater than about 14. In one embodiment, the nanoparticle dispersion further includes one or more low hydrophile-lipophile-balance (HLB) surfactants each independently having a hydrophile-lipophile-balance (HLB) value less than about 10. In one embodiment, the nanoparticle dispersion further includes one or more phospholipid low hydrophile-lipophile-balance (HLB) surfactants each independently having a hydrophile-lipophile-balance (HLB) value less than about 10.

In one embodiment, the nanoparticle dispersion further includes one or more oil soluble vitamin and provitamins. In one embodiment, the nanoparticle dispersion further includes one or more cryoprotectants. In one embodiment, the nanoparticle dispersion further includes one or more additives.

The present invention provides a nanoparticle dispersion for topical delivery to skin of a mammal. The nanoparticle dispersion includes: one or more hydrophobic drugs selected from the group consisting of aspirin, benzocaine, hydrocortisone, Ibuprofen, and lidocaine; one or more polyethoxylated high hydrophile-lipophile-balance (HLB) surfactants; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride oi, isopropyl myristate, limonene, medium chain triglyeride oil, mineral oil, omega 3 fatty acid, oleyl alcohol, a combination of isohexadecane, isododecane, and a $C_{13-15}$ alkane; and sesame oil; and water.

In one embodiment, the one or more hydrophobic drugs each independently having a log P>1 do not form crystals from the nanoparticle dispersion for greater than about 8 months at a temperature from about 18° C. to about 22° C. In one embodiment, the one or more hydrophobic drugs are present in the nanoparticle dispersion from about 0.5 weight percent (wt. %) to about 5.7 weight percent (wt. %). In one embodiment, the one or more hydrophobic drugs are present in the nanoparticle dispersion from about 1.9 weight percent (wt. %) to about 5.1 weight percent (wt. %). In one embodiment, the one or more polyethoxylated high hydrophile-lipophile-balance (HLB) surfactants include one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30.

In one embodiment, the one or more polyethoxylated high hydrophile-lipophile-balance (HLB) surfactants are present in the nanoparticle dispersion from about 1.6 weight percent (wt. %) to about 11.9 weight percent (wt. %). In one embodiment, the one or more polyethoxylated high hydrophile-lipophile-balance (HLB) surfactants are present in the nanoparticle dispersion from about 3.0 weight percent (wt. %) to about 9.2 weight percent (wt. %). In one embodiment, the one or more polyethoxylated high hydrophile-lipophile-balance (HLB) surfactants include one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80 with the proviso that the nanoparticle dispersion further includes one or more phospholipid low hydrophile-lipophile-balance (HLB) surfactants selected from the group consisting of phosphatidylcholine and lecithin. In one embodiment, the one or more polyethoxylated high hydrophile-lipophile-balance (HLB) surfactants include one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30 and one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80.

In one embodiment, the one or more low hydrophile-lipophile-balance (HLB) surfactants are present in the nanoparticle dispersion from about 2.6 weight percent (wt. %) to about 12.0 weight percent (wt. %). In one embodiment, the one or more low hydrophile-lipophile-balance (HLB) surfactants are present in the nanoparticle dispersion from about 4.4 weight percent (wt. %) to about 9.7 weight percent (wt. %). In one embodiment, the one or more water immiscible oils are present in the nanoparticle dispersion from about 13.9 weight percent (wt. %) to about 41.8 weight percent (wt. %). In one embodiment, the one or more water immiscible oils are present in the nanoparticle dispersion from about 24.2 weight percent (wt. %) to about 31.4 weight percent (wt. %). In one embodiment, the nanoparticle dispersion further includes one or more non-polyethoxylated high hydrophile-lipophile-balance (HLB) surfactants selected from the group consisting of cocoglucoside, decyl glucoside, and xylityl caprate/caprylate.

In one embodiment, the one or more non-polyethoxylated high hydrophile-lipophile-balance (HLB) surfactants are present in the nanoparticle dispersion from about 1.1 weight percent (wt. %) to about 5.8 weight percent (wt. %). In one embodiment, the one or more non-polyethoxylated high hydrophile-lipophile-balance (HLB) surfactants are present in the nanoparticle dispersion from about 2 weight percent (wt. %) to about 4 weight percent (wt. %).

In one embodiment, the nanoparticle dispersion further includes one or more phospholipid low hydrophile-lipophile-balance (HLB) surfactants selected from the group consisting of phosphatidylcholine and lecithin. In one embodiment, the one or more phospholipid low hydrophile-lipophile-balance (HLB) surfactants are present in the nanoparticle dispersion from about 0.5 weight percent (wt. %) to about 5.8 weight percent (wt. %). In one embodiment, the one or more phospholipid low hydrophile-lipophile-balance (HLB) surfactants are present in the nanoparticle dispersion from about 2.0 weight percent (wt. %) to about 3.4 weight percent (wt. %).

In one embodiment, the nanoparticle dispersion further includes one or more oil soluble vitamin and provitamins selected from the group consisting of ascorbyl palmitate and tocopheryl acetate. In one embodiment, the one or more oil soluble vitamin and provitamins are present in the nanoparticle dispersion from about 0.5 weight percent (wt. %) to about 6.3 weight percent (wt. %). In one embodiment, the one or more oil soluble vitamin and provitamins are present in the nanoparticle dispersion from about 1.8 weight percent (wt. %) to about 4.6 weight percent (wt. %).

In one embodiment, the nanoparticle dispersion further includes one or more cryoprotectants selected from the group consisting of diethylene glycol, dimethyl sulfoxide, ethylene glycol, glycerin, propylene glycol, sorbitan, and trehalose. In one embodiment, the one or more cryoprotectants are present in the nanoparticle dispersion from about 15.2 weight percent (wt. %) to about 18.0 weight percent (wt. %). In one embodiment, the one or more cryoprotectants are present in the nanoparticle dispersion from about 15.2 weight percent (wt. %) to about 18.0 weight percent (wt. %).

In one embodiment, the nanoparticle dispersion further includes one or more additives selected from the group consisting of tetrasodium ethylenediaminetetraacetic acid, citric acid. butylated hydroxytoluene, and sodium chloride. In one embodiment, the one or more additives are present in the nanoparticle dispersion from about 0.03 weight percent (wt. %) to about 1.4 weight percent (wt. %). In one embodiment, the one or more additives are present in the nanoparticle dispersion from about 0.38 weight percent (wt. %) to about 0.71 weight percent (wt. %).

The present invention provides a nanoparticle dispersion for topical delivery to skin of a mammal. The nanoparticle dispersion includes: one or more hydrophobic drugs each independently having a log P>1; one or more ether type polyethoxylated high hydrophile-lipophile-balance (HLB) surfactants each independently having a hydrophile-lipophile-balance (HLB) value of equal to or greater than about 14; one or more low hydrophile-lipophile-balance (HLB) surfactants each independently having a hydrophile-lipophile-balance (HLB) value less than about 10; one or more water immiscible oils; and water.

In one embodiment, the one or more hydrophobic drugs each independently having a log P>1 do not form crystals from the nanoparticle dispersion for greater than about 8 months at a temperature from about 18° C. to about 22° C. In one embodiment, the one or more hydrophobic drugs each independently having a log P>1 are selected from the group consisting of aspirin, benzocaine, hydrocortisone, ibuprofen, and lidocaine. In one embodiment, the one or more hydrophobic drugs each independently having a log P>1 are present in the nanoparticle dispersion from about 0.5 weight percent (wt. %) to about 5.7 weight percent (wt. %). In one embodiment, the one or more hydrophobic drugs each independently having a log P>1 are present in the nanoparticle dispersion from about 1.9 weight percent (wt. %) to about 5.1 weight percent (wt. %).

In one embodiment, the one or more ether type polyethoxylated high hydrophile-lipophile-balance (HLB) surfactants each independently having a hydrophile-lipophile-balance (HLB) value of equal to or greater than about 14 are selected from the group consisting of laureth-23, laureth-30, steareth-100, steareth-20, steareth-40, ceteareth-20, and ceteareth-30. In one embodiment, the one or more ether type polyethoxylated high hydrophile-lipophile-balance (HLB) surfactants each independently having a hydrophile-lipophile-balance (HLB) value of equal to or greater than about 14 are present in the nanoparticle dispersion from about 1.6 weight percent (wt. %) to about 11.9 weight percent (wt. %). In one embodiment, the one or more ether type polyethoxylated high hydrophile-lipophile-balance (HLB) surfactants each independently having a hydrophile-lipophile-balance (HLB) value of equal to or greater than about 14 are present in the nanoparticle dispersion from about 3.0 weight percent (wt. %) to about 9.2 weight percent (wt. %).

In one embodiment, the one or more low hydrophile-lipophile-balance (HLB) surfactants each independently having a hydrophile-lipophile-balance (HLB) value less than about 10 are selected from the group consisting of stearic acid, sorbitan oleate, and sorbitan stearate. In one embodiment, the one or more low hydrophile-lipophile-balance (HLB) surfactants each independently having a hydrophile-lipophile-balance (HLB) value less than about 10 are present in the nanoparticle dispersion from about 2.6 weight percent (wt. %) to about 12.0 weight percent (wt. %). In one embodiment, the one or more low hydrophile-lipophile-balance (HLB) surfactants each independently having a hydrophile-lipophile-balance (HLB) value less than about 10 are present in the nanoparticle dispersion from about 4.4 weight percent (wt. %) to about 9.7 weight percent (wt. %).

In one embodiment, the one or more water immiscible oils are selected from the group consisting of cocoyl caprate/caprylate, benzyl alcohol, diisopropyl adipate, capric/caprylic triglyceride oil, isopropyl myristate, limonene, medium chain triglyeride oil, mineral oil, oleyl alcohol, sesame oil, and a combination of isohexadecane, isododecane, and a $C_{13-15}$ alkane. In one embodiment, the one or more water immiscible oils are present in the nanoparticle dispersion from about 13.9 weight percent (wt. %) to about 41.8 weight percent (wt. %). In one embodiment, the one or more water immiscible oils are present in the nanoparticle dispersion from about 24.2 weight percent (wt. %) to about 31.4 weight percent (wt. %).

In one embodiment, the nanoparticle dispersion further includes one or more ester type polyethoxylated high hydrophile-lipophile-balance (HLB) surfactants each independently having a hydrophile-lipophile-balance (HLB) value of equal to or greater than about 14. In one embodiment, the one or more ester type polyethoxylated high hydrophile-lipophile-balance (HLB) surfactants each independently having a hydrophile-lipophile-balance (HLB) value of equal to or greater than about 14 are selected from the group consisting of PEG100 stearate; PEG20 stearate; and polysorbate 80. In one embodiment, the one or more ester type polyethoxylated high hydrophile-lipophile-balance (HLB) surfactants each independently having a hydrophile-lipophile-balance (HLB) value of equal to or greater than about 14 are present in the nanoparticle dispersion from about 1.6 weight percent (wt. %) to about 11.9 weight percent (wt. %). In one embodiment, the one or more ester type polyethoxylated high hydrophile-lipophile-balance (HLB) surfactants each independently having a hydrophile-lipophile-balance (HLB) value of equal to or greater than about 14 are present in the nanoparticle dispersion from about 3.0 weight percent (wt. %) to about 9.2 weight percent (wt. %).

In one embodiment, the nanoparticle dispersion further includes one or more phospholipid low hydrophile-lipophile-balance (HLB) surfactants each independently having a hydrophile-lipophile-balance (HLB) value less than about 10. In one embodiment, the one or more phospholipid low hydrophile-lipophile-balance (HLB) surfactants each independently having a hydrophile-lipophile-balance (HLB) value less than about 10 are selected from the group consisting of phosphatidylcholine and lecithin. In one embodiment, the one or more phospholipid low hydrophile-lipophile-balance (HLB) surfactants are present in the nanoparticle dispersion from about 0.5 weight percent (wt. %) to about 5.8 weight percent (wt. %). In one embodiment, the one or more phospholipid low hydrophile-lipophile-balance (HLB) surfactants are present in the nanoparticle dispersion from about 2.0 weight percent (wt. %) to about 3.4 weight percent (wt. %).

In one embodiment, the nanoparticle dispersion further includes one or more non-polyethoxylated high hydrophile-lipophile-balance (HLB) surfactants each independently having a hydrophile-lipophile-balance (HLB) value of equal to or greater than about 14. In one embodiment, the one or more non-polyethoxylated high hydrophile-lipophile-balance (HLB) surfactants each independently having a hydrophile-lipophile-balance (HLB) value of equal to or greater than about 14 are selected from the group consisting of cocoglucoside, decyl glucoside, and xylityl caprate/caprylate. In one embodiment, the one or more non-polyethoxylated high hydrophile-lipophile-balance (HLB) surfactants each independently having a hydrophile-lipophile-balance (HLB) value of equal to or greater than about 14 are present in the nanoparticle dispersion from about 1.1 weight percent (wt. %) to about 5.8 weight percent (wt. %). In one embodiment, the one or more non-polyethoxylated high hydrophile-lipophile-balance (HLB) surfactants each independently having a hydrophile-lipophile-balance (HLB) value of equal to or greater than about 14 are present in the nanoparticle dispersion from about 2 weight percent (wt. %) to about 4 weight percent (wt. %).

In one embodiment, the nanoparticle dispersion further includes one or more oil soluble vitamin and provitamins selected from the group consisting of ascorbyl palmitate and tocopheryl acetate. In one embodiment, the one or more oil soluble vitamin and provitamins are present in the nanoparticle dispersion from about 0.5 weight percent (wt. %) to about 6.3 weight percent (wt. %). In one embodiment, the one or more oil soluble vitamin and provitamins are present in the nanoparticle dispersion from about 1.8 weight percent (wt. %) to about 4.6 weight percent (wt. %).

In one embodiment, the nanoparticle dispersion further includes one or more cryoprotectants. In one embodiment, the one or more cryoprotectants are selected from the group consisting of diethylene glycol, dimethyl sulfoxide, ethylene glycol, glycerin, propylene glycol, sorbitan, and trehalose. In one embodiment, the one or more cryoprotectants are present in the nanoparticle dispersion from about 15.2 weight percent (wt. %) to about 18.0 weight percent (wt. %). In one embodiment, the one or more cryoprotectants are present in the nanoparticle dispersion from about 15.2 weight percent (wt. %) to about 18.0 weight percent (wt. %).

In one embodiment, the nanoparticle dispersion further includes one or more additives. In one embodiment, the one or more additives are selected from the group consisting of tetrasodium ethylenediaminetetraacetic acid, citric acid, butylated hydroxytoluene, and sodium chloride. In one embodiment, the one or more additives are present in the nanoparticle dispersion from about 0.03 weight percent (wt. %) to about 1.4 weight percent (wt. %). In one embodiment, the one or more additives are present in the nanoparticle dispersion from about 0.38 weight percent (wt. %) to about 0.71 weight percent (wt. %).

The present invention provides a nanoparticle dispersion for topical delivery to skin of a mammal. The nanoparticle dispersion includes: one or more hydrophobic drugs selected from the group consisting of aspirin, benzocaine, hydrocortisone, Ibuprofen, and lidocaine; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride oil, isopropyl myristate, limonene, medium chain triglyeride oil, mineral oil, oleyl alcohol, sesame oil, and a combination of isohexadecane, isododecane, and a $C_{13-15}$ alkane; and water.

In one embodiment, the one or more hydrophobic drugs each independently having a log P>1 do not form crystals from the nanoparticle dispersion for greater than about 8 months at a temperature from about 18° C. to about 22° C.

In one embodiment, the nanoparticle dispersion further includes one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80. In one embodiment, the nanoparticle dispersion further includes one or more phospholipid low hydrophile-lipophile-balance (HLB) surfactants selected from the group consisting of phosphatidylcholine and lecithin.

The present invention provides a nanoparticle dispersion for topical delivery to skin of a mammal. The nanoparticle dispersion includes: one or more hydrophobic drugs selected from the group consisting of aspirin, benzocaine, hydrocortisone, ibuprofen, and lidocaine; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride oil, isopropyl myristate, limonene, medium chain triglyeride oil, mineral oil, oleyl alcohol, sesame oil, and a combination of isohexadecane, Isododecane, and a $C_{13-15}$ alkane; and water.

In one embodiment, the one or more hydrophobic drugs each independently having a log P>1 do not form crystals from the nanoparticle dispersion for greater than about 8 months at a temperature from about 18° C. to about 22° C.

The present invention provides a nanoparticle dispersion for topical delivery to skin of a mammal. The nanoparticle dispersion includes: one or more hydrophobic drugs selected from the group consisting of aspirin, benzocaine, hydrocortisone, ibuprofen, and lidocaine; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80; one or more phospholipid low hydrophile-lipophile-balance (HLB) surfactants selected from the group consisting of phosphatidylcholine and lecithin; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride oil, isopropyl myristate, limonene, medium chain triglyeride oil, mineral oil, oleyl alcohol, sesame oil, and a combination of isohexadecane, isododecane, and a $C_{13-15}$ alkane; and water. In one embodiment, the one or more hydrophobic drugs each independently having a log P>1 do not form crystals from the nanoparticle dispersion for greater than about 8 months at a temperature from about 18° C. to about 22° C.

The present invention provides a nanoparticle dispersion for topical delivery to skin of a mammal. The nanoparticle dispersion includes: one or more hydrophobic drugs selected from the group consisting of aspirin, benzocaine, hydrocortisone, ibuprofen, and lidocaine; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80; one or more non-polyethoxylated high hydrophile-lipophile-balance (HLB) surfactants selected from the group consisting of cocoglucoside, decyl glucoside, and xylityl caprate/caprylate; one or more phospholipid low hydrophile-lipophile-balance (HLB) surfactants selected from the group consisting of phosphatidylcholine and lecithin; one or more low hydrophile-lipophile-balance (HLB) surfactants selected from the group consisting of stearic acid, sorbitan oleate, and sorbitan stearate; one or more water immiscible oils selected from the group consisting of cocoyl caprylate, benzyl alcohol, diisopropyl adipate, capric/caprylic triglyceride oi, isopropyl myristate, limonene, medium chain triglyeride oil, mineral oil, oleyl alcohol, sesame oil, and a combination of isohexadecane, isododecane, and a $C_{13-15}$ alkane; and water. In one embodiment, the one or more hydrophobic drugs each independently having a log P>1 do not form crystals from the nanoparticle dispersion for greater than about 8 months at a temperature from about 18° C. to about 22° C.

The present invention provides a nanoparticle dispersion for topical delivery to skin of a mammal. The nanoparticle dispersion includes: ibuprofen; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride ol, isopropyl myristate, limonene, medium chain triglyeride oil, mineral oi, omega 3 fatty acid, oleyl alcohol, sesame oil, and a combination of isohexadecane, isododecane, and a $C_{13-15}$ alkane; and water. In one embodiment, the ibuprofen does not form crystals from the nanoparticle dispersion for greater than about 8 months at a temperature from about 18° C. to about 22° C.

In one embodiment, the nanoparticle dispersion further includes one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80. In one embodiment, the nanoparticle dispersion further includes one or more phospholipid low hydrophile-lipophile-balance (HLB) surfactants selected from the group consisting of phosphatidylcholine and lecithin.

The present invention provides a nanoparticle dispersion for topical delivery to skin of a mammal. The nanoparticle dispersion includes: Ibuprofen; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride oil, isopropyl myristate, limonene, medium chain triglyeride oil, mineral oi, omega 3 fatty acid, oleyl alcohol, sesame oil, and a combination of isohexadecane, isododecane, and a $C_{13-15}$ alkane; and water. In one embodiment, the ibuprofen does not form crystals from the nanoparticle dispersion for greater than about 8 months at a temperature from about 18° C. to about 22° C.

The present invention provides a nanoparticle dispersion for topical delivery to skin of a mammal. The nanoparticle dispersion includes: ibuprofen; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80; one or more phospholipid low hydrophile-lipophile-balance (HLB) surfactants selected from the group consisting of phosphatidylcholine and lecithin; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride oil, isopropyl myristate, limonene, medium chain triglyeride oil, mineral oil, omega 3 fatty acid, oleyl alcohol, sesame oil, and a combination of isohexadecane, isododecane, and a $C_{13-15}$ alkane; and water. In one embodiment, the ibuprofen does not form crystals from the nanoparticle dispersion for greater than about 8 months at a temperature from about 18° C. to about 22° C.

The present invention provides a nanoparticle dispersion for topical delivery to skin of a mammal. The nanoparticle dispersion includes: ibuprofen; one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30; one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80; one or more non-polyethoxylated high hydrophile-lipophile-balance (HLB) surfactants selected from the group consisting of cocoglucoside, decyl glucoside, and xylityl caprate/caprylate; one or more phospholipid low hydrophile-lipophile-balance (HLB) surfactants selected from the group consisting of phosphatidylcholine and lecithin; one or more low hydrophile-lipophile-balance (HLB) surfactants selected from the group consisting of stearic acid, sorbitan oleate, and sorbitan stearate; one or more water immiscible oils selected from the group consisting of cocoyl caprate/caprylate, benzyl alcohol, diisopropyl adipate, capric/caprylic triglyceride oil, isopropyl myristate, limonene, medium chain triglyeride oil, mineral oil, omega 3 fatty acid, oleyl alcohol, sesame oil, and a combination of isohexadecane, isododecane, and a $C_{13-15}$ alkane; and water. In one embodiment, the ibuprofen does not form crystals from the nanoparticle dispersion for greater than about 8 months at a temperature from about 18° C. to about 22° C.

The present invention provides a nanoparticle dispersion for topical delivery to skin of a mammal. The nanoparticle dispersion includes: ibuprofen; one or more ester type polyethoxylated high hydrophile-lipophile-balance (HLB) surfactants each independently having a hydrophile-lipophile-balance (HLB) value of equal to or greater than about 14; one or more phospholipid low hydrophile-lipophile-balance (HLB) surfactants each independently having a hydrophile-lipophile-balance (HLB) value less than about 10; one or more low hydrophile-lipophile-balance (HLB) surfactants each independently having a hydrophile-lipophile-balance (HLB) value less than about 10; one or more water immiscible oils; and water.

In one embodiment, the ibuprofen does not form crystals from the nanoparticle dispersion for greater than about 8 months at a temperature from about 18° C. to about 22° C. In one embodiment, the ibuprofen is present in the nanoparticle dispersion from about 0.5 weight percent (wt. %) to about 5.7 weight percent (wt. %). In one embodiment, the ibuprofen Is present in the nanoparticle dispersion from about 1.9 weight percent (wt. %) to about 5.1 weight percent (wt. %).

In one embodiment, the one or more ester type polyethoxylated high hydrophile-lipophile-balance (HLB) surfactants each independently having a hydrophile-lipophile-balance (HLB) value of equal to or greater than about 14 are selected from the group consisting of PEG32 stearate and polysorbate 80. In one embodiment, the one or more ester type polyethoxylated high hydrophile-lipophile-balance (HLB) surfactants each independently having a hydrophile-lipophile-balance (HLB) value of equal to or greater than about 14 are present in the nanoparticle dispersion from about 1.6 weight percent (wt. %) to about 11.9 weight percent (wt. %). In one embodiment, the one or more ester type polyethoxylated high hydrophile-lipophile-balance (HLB) surfactants each independently having a hydrophile-lipophile-balance (HLB) value of equal to or greater than about 14 are present in the nanoparticle dispersion from about 3.0 weight percent (wt. %) to about 9.2 weight percent (wt. %).

In one embodiment, the one or more phospholipid low hydrophile-lipophile-balance (HLB) surfactants each independently having a hydrophile-lipophile-balance (HLB) value less than about 10 are selected from the group consisting of phosphatidylcholine and lecithin. In one embodiment, the one or more phospholipid low hydrophile-lipophile-balance (HLB) surfactants each independently having a hydrophile-lipophile-balance (HLB) value less than about 10 are present in the nanoparticle dispersion from about 0.5 weight percent (wt. %) to about 5.8 weight percent (wt. %). In one embodiment, the one or more phospholipid low hydrophile-lipophile-balance (HLB) surfactants each independently having a hydrophile-lipophile-balance (HLB) value less than about 10 are present in the nanoparticle dispersion from about 2.0 weight percent (wt. %) to about 3.4 weight percent (wt. %).

In one embodiment, the one or more low hydrophile-lipophile-balance (HLB) surfactants each independently having a hydrophile-lipophile-balance (HLB) value less than about 10 includes sorbitan oleate. In one embodiment, the one or more low hydrophile-lipophile-balance (HLB) surfactants each independently having a hydrophile-lipophile-balance (HLB) value less than about 10 are present in the nanoparticle dispersion from about 2.6 weight percent (wt. %) to about 12.0 weight percent (wt. %). In one embodiment, the one or more low hydrophile-lipophile-balance (HLB) surfactants each independently having a hydrophile-lipophile-balance (HLB) value less than about 10 are present in the nanoparticle dispersion from about 4.4 weight percent (wt. %) to about 9.7 weight percent (wt. %).

In one embodiment, the one or more water immiscible oils are selected from the group consisting of capric/caprylic triglyceride oil, isopropyl myristate, limonene, and a combination of isohexadecane, isododecane, and a $C_{13-15}$ alkane. In one embodiment, the one or more water immiscible oils are present in the nanoparticle dispersion from about 13.9 weight percent (wt. %) to about 41.8 weight percent (wt. %). In one embodiment, the one or more water immiscible oils are present in the nanoparticle dispersion from about 24.2 weight percent (wt. %) to about 31.4 weight percent (wt. %). In one embodiment, the nanoparticle dispersion further includes one or more additives. In one embodiment, the one or more additives includes sodium chloride. In one embodiment, the one or more additives are present in the nanoparticle dispersion from about 0.03 weight percent (wt. %) to about 1.4 weight percent (wt. %). In one embodiment, the one or more additives are present in the nanoparticle dispersion from about 0.38 weight percent (wt. %) to about 0.71 weight percent (wt. %).

The present invention provides a nanoparticle dispersion for topical delivery to skin of a mammal. The nanoparticle dispersion includes: Ibuprofen; one or more ester type polyethoxylated high hydrophile-lipophile-balance (HLB) surfactants selected from the group consisting of PEG32 stearate and polysorbate 80; one or more phospholipid low hydrophile-lipophile-balance (HLB) surfactants selected from the group consisting of phosphatidylcholine and lecithin; one or more low hydrophile-lipophile-balance (HLB) surfactants including sorbitan oleate; one or more water immiscible oils selected from the group consisting of capric/caprylic triglyceride oi, isopropyl myristate, limonene, and a combination of isohexadecane, isododecane, and a $C_{13-15}$ alkane; and water.

In one embodiment, the ibuprofen does not form crystals from the nanoparticle dispersion for greater than about 8 months at a temperature from about 18° C. to about 22° C. In one embodiment, the ibuprofen is present in the nanoparticle dispersion from about 0.5 weight percent (wt. %) to about 5.7 weight percent (wt. %). In one embodiment, the ibuprofen is present in the nanoparticle dispersion from about 1.9 weight percent (wt. %) to about 5.1 weight percent (wt. %).

In one embodiment, the one or more ester type polyethoxylated high hydrophile-lipophile-balance (HLB) surfactants selected from the group consisting of PEG32 stearate and polysorbate 80 are present in the nanoparticle dispersion from about 1.6 weight percent (wt. %) to about 11.9 weight percent (wt. %). In one embodiment, the one or more ester type polyethoxylated high hydrophile-lipophile-balance (HLB) surfactants selected from the group consisting of PEG32 stearate and polysorbate 80 are present in the nanoparticle dispersion from about 3.0 weight percent (wt. %) to about 9.2 weight percent (wt. %).

In one embodiment, the one or more phospholipid low hydrophile-lipophile-balance (HLB) surfactants selected from the group consisting of phosphatidylcholine and lecithin are present in the nanoparticle dispersion from about 0.5 weight percent (wt. %) to about 5.8 weight percent (wt. %). In one embodiment, the one or more phospholipid low hydrophile-lipophile-balance (HLB) surfactants selected from the group consisting of phosphatidylcholine and lecithin are present in the nanoparticle dispersion from about 2.0 weight percent (wt. %) to about 3.4 weight percent (wt. %). In one embodiment, the one or more low hydrophile-lipophile-balance (HLB) surfactants including sorbitan oleate are present in the nanoparticle dispersion from about 2.6 weight percent (wt. %) to about 12.0 weight percent (wt. %). In one embodiment, the one or more low hydrophile-lipophile-balance (HLB) surfactants including sorbitan oleate are present in the nanoparticle dispersion from about 4.4 weight percent (wt. %) to about 9.7 weight percent (wt. %).

In one embodiment, the one or more water immiscible oils selected from the group consisting of capric/caprylic triglyceride oil, isopropyl myristate, limonene, and a combination of isohexadecane, Isododecane, and a $C_{13-15}$ alkane are present in the nanoparticle dispersion from about 13.9 weight percent (wt. %) to about 41.8 weight percent (wt. %). In one embodiment, the one or more water immiscible oils selected from the group consisting of capric/caprylic triglyceride oil, isopropyl myristate, limonene, and a combination of isohexadecane, isododecane, and a $C_{13-15}$ alkane are present in the nanoparticle dispersion from about 24.2 weight percent (wt. %) to about 31.4 weight percent (wt. %).

In one embodiment, the nanoparticle dispersion further includes one or more additives. In one embodiment, the one or more additives include sodium chloride. In one embodiment, the one or more additives are present in the nanoparticle dispersion from about 0.03 weight percent (wt. %) to about 1.4 weight percent (wt. %). In one embodiment, the one or more additives are present in the nanoparticle dispersion from about 0.38 weight percent (wt. %) to about 0.71 weight percent (wt. %).

The present invention provides a nanoparticle dispersion for topical delivery to skin of a mammal. The nanoparticle dispersion includes: ibuprofen; sorbitan oleate; laureth-23; PEG100 stearate; capric/caprylic triglyceride oil; isopropyl myristate; limonene; phosphatidylcholine; and water.

The present invention provides a nanoparticle dispersion for topical delivery to skin of a mammal. The nanoparticle dispersion includes: about 5.2 weight percent (wt. %). Ibuprofen; about 3.1 weight percent (wt. %) sorbitan oleate; about 6.2 weight percent (wt. %) laureth-23; about 4.6 weight percent (wt. %) PEG100 stearate; about 1.0 weight percent (wt. %) capric/caprylic triglyceride oil; about 20.5 weight percent (wt. %) isopropyl myristate; about 5.2 weight percent (wt. %) limonene; about 0.5 weight percent (wt. %) phosphatidylcholine; and about 53.7 weight percent (wt. %) water.

The present invention provides a nanoparticle dispersion for topical delivery to skin of a mammal. The nanoparticle dispersion includes: lidocaine; sorbitan oleate; ceteareth-30; xylityl caprate/caprylate; isopropyl myristate; mineral oil; capric/caprylic triglyceride oil; lecithin; and water.

The present invention provides a nanoparticle dispersion for topical delivery to skin of a mammal. The nanoparticle dispersion includes: about 1.1 weight percent (wt. %) lidocaine; about 5.4 weight percent (wt. %) sorbitan oleate; about 5.4 weight percent (wt. %) ceteareth-30; about 5.4 weight percent (wt. %) xylityl caprate/caprylate; about 8.7 weight percent (wt. %) isopropyl myristate; about 8.6 weight percent (wt. %) mineral oil; about 8.6 weight percent (wt. %) capric/caprylic triglyceride oil; about 3.2 weight percent (wt. %) lecithin; and about 53.7 weight percent (wt. %) water.

The present invention provides a nanoparticle dispersion for topical delivery to skin of a mammal. The nanoparticle dispersion includes: ibuprofen; sorbitan oleate; PEG32 stearate; capric/caprylic triglyceride oil; isopropyl myristate; limonene; lecithin; and water.

The present invention provides a nanoparticle dispersion for topical delivery to skin of a mammal. The nanoparticle dispersion includes: about 5.5 weight percent (wt. %) ibuprofen; about 4.8 weight percent (wt. %) sorbitan oleate; about 10.9 weight percent (wt. %) PEG32 stearate; about 13.3 weight percent (wt. %) capric/caprylic triglyceride oil; about 13.3 weight percent (wt. %) isopropyl myristate; about 4.1 weight percent (wt. %) limonene; about 3.5 weight percent (wt. %) lecithin; and about 44.6 weight percent (wt. %) water.

The present invention provides a nanoparticle dispersion for topical delivery to skin of a mammal. The nanoparticle dispersion includes: ibuprofen; sorbitan oleate; ceteareth-20, capric/caprylic triglyceride oil; isopropyl myristate; limonene; glycerin; dimethyl sulfoxide; and water.

The present invention provides a nanoparticle dispersion for topical delivery to skin of a mammal. The nanoparticle dispersion includes: about 5.5 weight percent (wt. %) ibuprofen; about 4.8 weight percent (wt. %) sorbitan oleate; about 11.1 weight percent (wt. %) ceteareth-20, about 13.5 weight percent (wt. %) capric/caprylic triglyceride oil; about 13.5 weight percent (wt. %) isopropyl myristate; about 3.9 weight percent (wt. %) limonene; about 16.0 weight percent (wt. %) glycerin; about 2.0 weight percent (wt. %) dimethyl sulfoxide; and about 29.7 weight percent (wt. %) water.

The present invention provides a nanoparticle dispersion for topical delivery to skin of a mammal. The nanoparticle dispersion includes: one or more hydrophobic bioactive agents; one or more low hydrophile-lipophile-balance (HLB) surfactants each independently having a hydrophile-lipophile-balance (HLB) value less than about 10; one or more water immiscible oils; and water.

In one embodiment, the one or more hydrophobic bioactive agents do not form crystals from the nanoparticle dispersion for greater than about 8 months at a temperature from about 18° C. to about 22° C. In one embodiment, the nanoparticle dispersion is essentially free of ibuprofen and S-ibuprofen. In one embodiment, the one or more hydrophobic bioactive agents are selected from the group consisting of ascorbyl palmitate, coenzyme Q, retinyl palmitate, tocopheryl acetate, birch bark extract, cannabidiol, frankincense essential oil, methyl salicylate, resveratrol, and undecylenic acid. In one embodiment, the one or more low hydrophile-lipophile-balance (HLB) surfactants each independently having a hydrophile-lipophile-balance (HLB) value less than about 10 are selected from the group consisting of glyceryl monostearate, octanoic acid, stearic acid, sorbitan oleate, and sorbitan stearate. In one embodiment, the one or more water immiscible ois are selected from the group consisting of soy biodiesel extract, diisopropyl adipate, ethyl oleate, capric/caprylic triglyceride oil, isopropyl myristate, limonene, medium chain triglyeride oil, mineral oil, and omega 3 fatty acid.

In one embodiment, the nanoparticle dispersion further includes one or more ether type polyethoxylated high hydrophile-lipophile-balance (HLB) surfactants each independently having a hydrophile-lipophile-balance (HLB) value of equal to or greater than about 14. In one embodiment, the one or more ether type polyethoxylated high hydrophile-lipophile-balance (HLB) surfactants each independently having a hydrophile-lipophile-balance (HLB) value of equal to or greater than about 14 are selected from the group consisting of laureth-23, laureth-30, ceteareth-20, and ceteareth-30. In one embodiment, the nanoparticle dispersion further includes one or more ester type polyethoxylated high hydrophile-lipophile-balance (HLB) surfactants each independently having a hydrophile-lipophile-balance (HLB) value of equal to or greater than about 14. In one embodiment, the one or more ester type polyethoxylated high hydrophile-lipophile-balance (HLB) surfactants each independently having a hydrophile-lipophile-balance (HLB) value of equal to or greater than about 14 are selected from the group consisting of PEG100 stearate, polysorbate 20, polysorbate 80.

In one embodiment, the nanoparticle dispersion further includes one or more ether type polyethoxylated high hydrophile-lipophile-balance (HLB) surfactants each independently having a hydrophile-lipophile-balance (HLB) value of equal to or greater than about 14 and one or more ester type polyethoxylated high hydrophile-lipophile-balance (HLB) surfactants each independently having a hydrophile-lipophile-balance (HLB) value of equal to or greater than about 14. In one embodiment, the one or more ether type polyethoxylated high hydrophile-lipophile-balance (HLB) surfactants each independently having a hydrophile-lipophile-balance (HLB) value of equal to or greater than about 14 are selected from the group consisting of laureth-23, laureth-30, ceteareth-20, and ceteareth-30 and one or more ester type polyethoxylated high hydrophile-lipophile-balance (HLB) surfactants each independently having a hydrophile-lipophile-balance (HLB) value of equal to or greater than about 14 are selected from the group consisting of PEG100 stearate, polysorbate 20, polysorbate 80.

In one embodiment, the nanoparticle dispersion further includes one or more non-polyethoxylated high hydrophilelipophile-balance (HLB) surfactants each independently having a hydrophile-lipophile-balance (HLB) value of equal to or greater than about 14. In one embodiment, the one or more non-polyethoxylated high hydrophile-lipophile-balance (HLB) surfactants each independently having a hydrophile-lipophile-balance (HLB) value of equal to or greater than about 14 include sodium lauryl sulfate.

In one embodiment, the nanoparticle dispersion further includes one or more low hydrophile-lipophile-balance (HLB) surfactants each independently having a hydrophile-lipophile-balance (HLB) value less than about 10. In one embodiment, the one or more non-polyethoxylated high hydrophile-lipophile-balance (HLB) surfactants each independently having a hydrophile-lipophile-balance (HLB) value of equal to or greater than about 14 are selected from the group consisting of phosphatidylcholine and lecithin.

In one embodiment, the nanoparticle dispersion further includes one or more additives selected from the group consisting of tetrasodium ethylenediaminetetraacetic acid, citric acid, butylated hydroxytoluene, and sodium chloride.

The present invention provides a nanoparticle dispersion for topical delivery to skin of a mammal. The nanoparticle dispersion includes: one or more hydrophobic bioactive agents; the one or more hydrophobic bioactive agents selected from the group consisting of ascorbyl palmitate, coenzyme Q, retinyl palmitate, tocopheryl acetate, birch bark extract, cannabidiol, frankincense essential oil, methyl salicylate, resveratrol, and undecylenic acid.

In one embodiment, the or more low hydrophile-lipophile-balance (HLB) surfactants selected from the group consisting of glyceryl monostearate, octanoic acid, stearic acid, sorbitan oleate, and sorbitan stearate; one or more water immiscible oils selected from the group consisting of soy biodiesel extract, diisopropyl adipate, ethyl oleate, capric/caprylic triglyceride oil, isopropyl myristate, limonene, medium chain triglyceride oil, mineral oil, and omega 3 fatty acid; and water.

In one embodiment, the nanoparticle dispersion further includes one or more ether type polyethoxylated high hydrophile-lipophile-balance (HLB) surfactants each independently having a hydrophile-lipophile-balance (HLB) value of equal to or greater than about 14 are selected from the group consisting of laureth-23, laureth-30, ceteareth-20, and ceteareth-30. In one embodiment, the nanoparticle dispersion further one or more ester type polyethoxylated high hydrophile-lipophile-balance (HLB) surfactants selected from the group consisting of PEG100 stearate, polysorbate 20, polysorbate 80. In one embodiment, the nanoparticle dispersion further includes one or more ether type polyethoxylated high hydrophile-lipophile-balance (HLB) surfactants selected from the group consisting of laureth-23, laureth-30, ceteareth-20, and ceteareth-30 and one or more ester type polyethoxylated high hydrophile-lipophile-balance (HLB) surfactants selected from the group consisting of PEG100 stearate, polysorbate 20, polysorbate 80. In one embodiment, the nanoparticle dispersion further includes one or more non-polyethoxylated high hydrophile-lipophile-balance (HLB) surfactants including sodium lauryl sulfate. In one embodiment, the nanoparticle dispersion further includes one or more low hydrophile-lipophile-balance (HLB) surfactants selected from the group consisting of phosphatidylcholine and lecithin. In one embodiment, the nanoparticle dispersion further includes one or more additives selected from the group consisting of tetrasodium ethylenediaminetetraacetic acid, citric acid, butylated hydroxytoluene, and sodium chloride.

The present invention provides a nanoparticle dispersion for topical delivery to skin of a mammal. The nanoparticle dispersion includes: cannabidiol; polysorbate 20; polysorbate 80; glyceryl monostearate; lecithin; ethyl oleate; medium chain triglyceride oil; and water.

The present invention provides a nanoparticle dispersion for topical delivery to skin of a mammal. The nanoparticle dispersion includes: about 1.7 weight percent (wt. %) cannabidiol; about 3.3 weight percent (wt. %) polysorbate 20; about 6.4 weight percent (wt. %) polysorbate 80; about 1.3 weight percent (wt. %) glyceryl monostearate; about 5.8 weight percent (wt. %) lecithin; about 30.1 weight percent (wt. %) ethyl oleate; about 11.7 weight percent (wt. %) medium chain triglyeride oil; and about 39.6 weight percent (wt. %) water.

The present invention provides a method of preparing nanoparticles by a modified hot-melt extruder. The method includes: providing a parallel twin screw extruder having about 40 length/diameter (L/D), a first zone, a second zone, a third zone, a fourth zone, a fifth zone, a sixth zone, a seventh zone, and eight zone, and an external cooling jacket, wherein the first about 13 length/diameter (L/D) of the parallel twin screw extruder consisted of 1/1 pitch conveying elements, the second about 6 length/diameter (L/D) of the parallel twin screw extruder consisted of mixing elements, and the final about 21 length/diameter (LID) of the parallel twin screw extruder consisted of 1/1 pitch conveying elements, wherein the first zone, the second zone, the third zone, the fourth zone, the fifth zone, the sixth zone, the seventh zone, and the eighth zone are in series, wherein the external cooling jacket was in contact with the final about 21 length/diameter (L/D) and was at a temperature from about 6° C. to about 30° C., wherein the first zone was at a temperature from about 56° C. to about 95° C., wherein the second zone was at a temperature from about 54° C. to about 95° C., wherein the third zone was at a temperature from about 17° C. to about 94° C., wherein the fourth zone was at a temperature from about 15° C. to about 89° C., wherein the fifth zone was at a temperature from about 13° C. to about 65° C., wherein the sixth zone was at a temperature from about 14° C. to about 39° C., wherein seventh zone was at a temperature from about 18° C. to about 34° C., wherein eighth zone was at a temperature from about 15° C. to about 30° C., wherein the twin screws were rotated at from about 50 rpm to about 250 rpm; introducing a mill base into the first zone of the parallel twin screw extruder at a rate from about 14 grams/minute to about 380 grams/minute, wherein the mill base was maintained at a temperature from about 40° C. to about 100° C.; wherein the mill base includes: from about 1.5 to about 11.9 weight percent (wt. %) polyethoxylated high hydrophile-lipophile-balance (HLB) surfactant, from about 2.6 to about 12.0 weight percent (wt. %) low hydrophile-lipophile-balance (HLB) surfactant, from about 13.9 to about 41.8 weight percent (wt. %) water immiscible oil, and from about 40 to about 75 weight percent (wt. %) aqueous phase, wherein the mill base forms a lamellar structure microemulsion between about 60° C. and about 100° C.; collecting the nanoparticle dispersion exiting the eighth zone, and wherein the nanoparticle dispersion was at a temperature from about 7° C. to about 30° C.

The present invention provides a method of preparing nanoparticles by a modified hot-melt extruder. The method includes: providing a parallel twin screw extruder having about 40 length/diameter (L/D), a first zone, a second zone, a third zone, a fourth zone, a fifth zone, a sixth zone, a seventh zone, and eight zone, and an external cooling jacket, wherein the first about 13 length/diameter (L/D) of the parallel twin screw extruder consisted of 1/1 pitch conveying elements, the second about 6 length/diameter (L/D) of the parallel twin screw extruder consisted of mixing elements, and the final about 21 length/diameter (L/D) of the parallel twin screw extruder consisted of 1/1 pitch conveying elements, wherein the first zone, the second zone, the third zone, the fourth zone, the fifth zone, the sixth zone, the seventh zone, and the eighth zone are in series, wherein the external cooling jacket was in contact with the final about 21 length/diameter (L/D) and was at a temperature from about 6° C. to about 30° C., wherein the first zone was at a temperature from about 56° C. to about 95° C., wherein the second zone was at a temperature from about 54° C. to about 95° C., wherein the third zone was at a temperature from about 17° C. to about 94° C., wherein the fourth zone was at a temperature from about 15° C. to about 89° C., wherein the fifth zone was at a temperature from about 13° C. to about 65° C., wherein the sixth zone was at a temperature from about 14° C. to about 39° C., wherein seventh zone was at a temperature from about 18° C. to about 34° C., wherein eighth zone was at a temperature from about 15° C. to about 30° C., wherein the twin screws were rotated at from about 50 rpm to about 250 rpm; introducing a mill base into the first zone of the parallel twin screw extruder at a rate from about 14 grams/minute to about 380 grams/minute, wherein the mill base was maintained at a temperature from about 40° C. to about 100° C.; wherein the mill base includes: any composition described herein, wherein the mill base forms a lamellar structure microemulsion between about 60° C. and about 100° C.; collecting the nanoparticle dispersion exiting the eighth zone, and wherein the nanoparticle dispersion was at a temperature from about 7° C. to about 30° C.

The present invention provides a method of preparing nanoparticles by a modified hot-melt extruder. The method includes: providing a parallel twin screw extruder having one or more zones and an external cooling jacket, wherein the external cooing jacket was at a temperature from about 6° C. to about 30° C., wherein the one or more zones were at a temperature from about 13° C. to about 95° C., wherein the twin screws were rotated at from about 50 rpm to about 250 rpm; introducing a mill base into the one or more zones of the parallel twin screw extruder at a rate from about 14 grams/minute to about 380 grams/minute, wherein the mill base was maintained at a temperature from about 40° C. to about 100° C.; wherein the mill base includes: from about 1.5 to about 11.9 weight percent (wt. %) polyethoxylated high hydrophile-lipophile-balance (HLB) surfactant, from about 2.6 to about 12.0 weight percent (wt. %) low hydrophile-lipophile-balance (HLB) surfactant, from about 13.9 to about 41.8 weight percent (wt. %) water immiscible oil, and from about 40 to about 75 weight percent (wt. %) aqueous phase, wherein the mill base forms a lamellar structure microemulsion between 60° C. and 100° C.; collecting the nanoparticle dispersion exiting the eighth zone, and wherein the nanoparticle dispersion was at a temperature from about 7° C. to about 30° C.

The present invention provides a method of preparing nanoparticles by a modified hot-melt extruder. The method includes: providing a parallel twin screw extruder having one or more zones and an external cooling jacket, wherein the external cooling jacket was at a temperature from about 6° C. to about 30° C., wherein the one or more zones were at a temperature from about 13° C. to about 95° C., wherein the twin screws were rotated at from about 50 rpm to about 250 rpm; introducing a mill base into the one or more zones of the parallel twin screw extruder at a rate from about 14 grams/minute to about 380 grams/minute, wherein the mill base was maintained at a temperature from about 40° C. to about 100° C.; wherein the mill base includes any composition described herein, wherein the mill base forms a lamellar structure microemulsion between 60° C. and 100° C.; collecting the nanoparticle dispersion exiting the eighth zone, and wherein the nanoparticle dispersion was at a temperature from about 7° C. to about 30° C.

The present invention provides a method of preparing nanoparticles by a modified hot-melt extruder. The method includes: providing a parallel twin screw extruder having one or more cooling zones, wherein the one or more cooling zones were at a temperature from about 0° C. to about 30° C., wherein the twin screws were rotated at from about 50 rpm to about 250 rpm; introducing a mill base into the one or more zones of the parallel twin screw extruder at a rate from about 15 grams/minute to about 380 grams/minute, wherein the mill base was maintained at a temperature from about 40° C. to about 100° C.; wherein the mill base includes: from about 1.5 to about 11.9 weight percent (wt. %) polyethoxylated high hydrophile-lipophile-balance (HLB) surfactant, from about 2.6 to about 12.0 weight percent (wt. %) low hydrophile-lipophile-balance (HLB) surfactant, from about 13.9 to about 41.8 weight percent (wt. %) water immiscible oil, and from about 40 to about 75 weight percent (wt. %) aqueous phase, wherein the mill base forms a lamellar structure microemulsion between 60° C. and 100° C.; collecting the nanoparticle dispersion exiting the twin screw extruder, and wherein the nanoparticle dispersion exiting the twin screw extruder was at a temperature from about 7° C. to about 30° C.

The present invention provides a method of preparing nanoparticles by a modified hot-melt extruder. The method includes: providing a parallel twin screw extruder having one or more cooling zones, wherein the one or more cooling zones were at a temperature from about 0° C. to about 30° C., wherein the twin screws were rotated at from about 50 rpm to about 250 rpm; introducing a mill base into the one or more zones of the parallel twin screw extruder at a rate from about 15 grams/minute to about 380 grams/minute, wherein the mill base was maintained at a temperature from about 40° C. to about 100° C.; wherein the mill base includes any composition described herein, wherein the mill base forms a lamellar structure microemulsion between 60° C. and 100° C.; collecting the nanoparticle dispersion exiting the twin screw extruder, and wherein the nanoparticle dispersion exiting the twin screw extruder was at a temperature from about 7° C. to about 30° C.

BRIEF DESCRIPTION OF THE DRAWINGS

Embodiments of the invention may be best understood by referring to the following description and accompanying drawings, which illustrate such embodiments. In the drawings.

Figure 1:
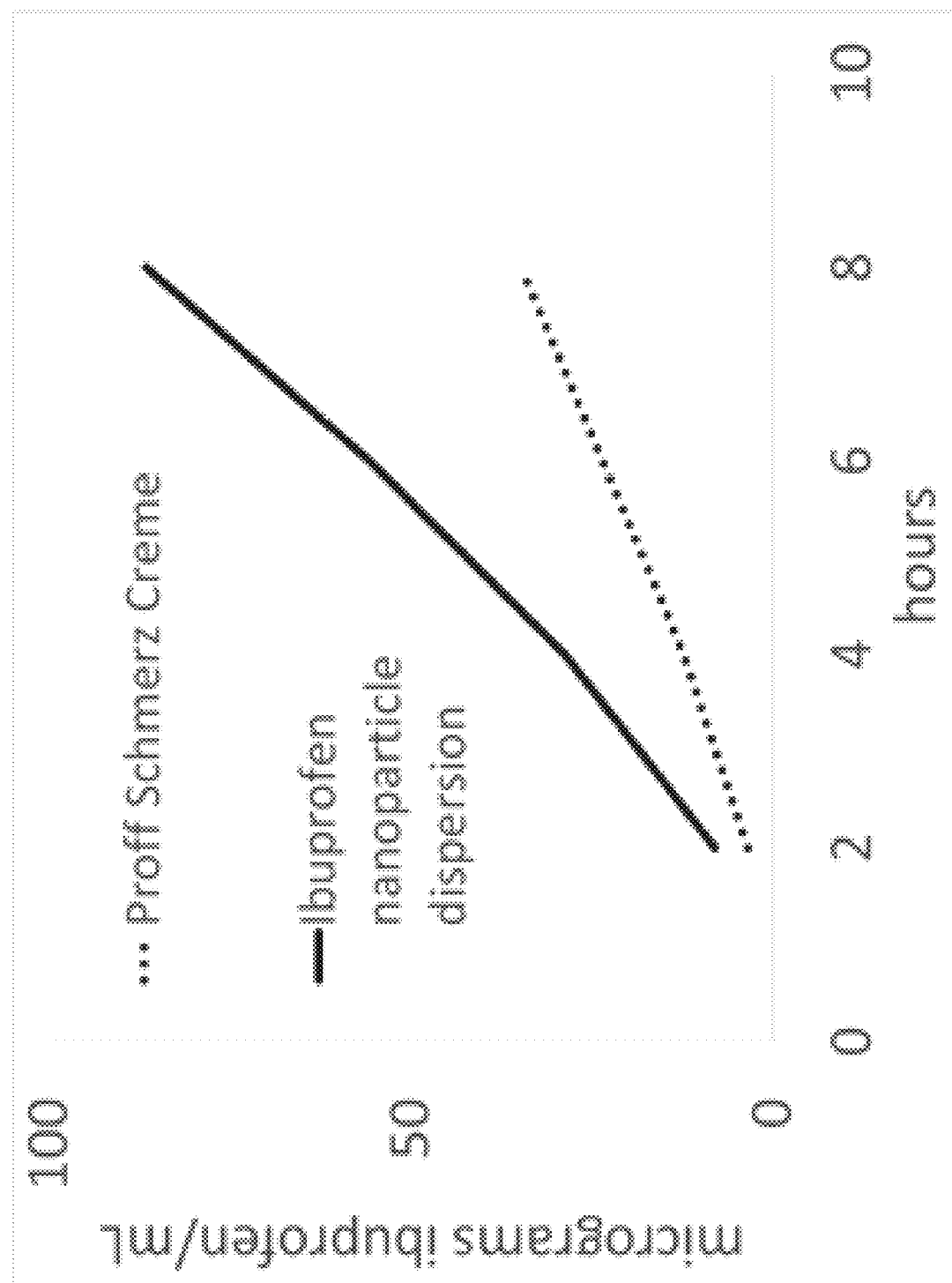
FIG. 1 is a plot of dermal permeation of ibuprofen from nanoparticle dispersion and Proff Schmerz Crème.

The drawings are not necessarily to scale. Like numbers used in the figures refer to like components, steps, and the like. However, it will be understood that the use of a number to refer to a component in a given figure is not intended to limit the component in another figure labeled with the same number.

DETAILED DESCRIPTION OF THE INVENTION

The present invention provides a nanoparticle dispersion for topical delivery to skin of a mammal. The nanoparticle dispersion includes: one or more hydrophobic bioactive agents or one or more hydrophobic drugs; one or more surfactants; one or more water immiscible oils; and water. Methods of preparing nanoparticle dispersions by hot melt extrusion are also provided.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed Independently, or In combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, M A, 1993 and *The American Heritage Dictionary of the English Language*, Houghton Mifflin, Boston Mass., 1981.

References in the specification to "one embodiment" indicate that the embodiment described may include, for example, a particular feature, structure, or characteristic, but every embodiment may not necessarily include, for example, the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example, about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "administration" refers to a method of placing a device to a desired site. The placing of a device can be by any pharmaceutically accepted means, for example, by swallowing, retaining it within the mouth until the drug has been dispensed, placing it within the buccal cavity, inserting, implanting, attaching, etc. These and other methods of administration are known in the art.

As used herein, the term "active pharmaceutical ingredient," or API, refers to a molecular entity adapted for treatment of a malcondition in a patient in need thereof.

As used herein, the term "drug" refers to a molecular entity adapted for treatment of a malcondition in a patient in need thereof.

As used herein, the term "bioactive agent" refers to a molecular entity adapted for treatment of a malcondition in a patient in need thereof.

As used herein, the term "comprising" or "comprises" is intended to mean that the compositions and methods include the recited elements, but not excluding others.

As used herein, the phrase "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the phrase "consisting of" shall mean excluding more than trace elements of other ingredients and substantial method steps.

As used herein, the terms "consisting essentially of" and "consisting of" are embodied in the term "comprising." In any chemical embodiment described herein, the term "comprising" may be amended, where appropriate, to the recite the terms "consisting essentially of" and "consisting of."

As used herein, the term "delivery" refers to the release of a drug from a device including that drug into an environment surrounding the device. The environment into which the drug so released may or may not be the ultimate site of activity for that drug. In some instances, the released drug may need to be transported to its ultimate site of activity.

As used herein, the term "dermis" refers to the sensitive connective tissue layer of the skin located below the epidermis, containing nerve endings, sweat and sebaceous glands, and blood and lymph vessels. Histologically, the dermis consists of a papillary layer and a reticular layer. The papillary layer contains the vessels and nerve endings supplying the epidermis. The reticular consists predominantly of elastic fibers and collagen.

As used herein, the term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

As used herein, the term "dispersing agent" refers to an agent that facilitates the formation of a dispersion of one or more internal phases in a continuous phase. Examples of such dispersions include suspensions and emulsions, wherein the continuous phase may be water, for example, and the internal phase is a solid or a water-immiscible liquid, respectively. Thus, dispersing agents may include suspending agents and emulsifying agents.

As used herein, the term "dosage form" refers to a physical and chemical composition of an active pharmaceutical ingredient (API) that is adapted for administration to a patient in need thereof. The inventive dosage form is a tablet. By a tablet is meant a relatively hard, compact object, suitable for oral ingestion, prepared by compression of a powder including an active pharmaceutical ingredient and, usually, excipients.

As used herein, the term "dosing event" refers to administration of an antiviral agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectible system); and a single subcutaneous injection followed by installation of a continuous delivery system.

As used herein, the term "edible" refers to substances approved by the United States Food and Drug Administration as foods or as additives to foods."

As used herein, the phrase "capric/caprylic triglyceride" refers to fractionated coconut oil, which is also called capric/caprylic triglyceride (CAS No. 65381-09-1).

As used herein, the term "drug" refers to a therapeutic agent or a diagnostic agent and includes any substance, other than food, used in the prevention, diagnosis, alleviation, treatment, or cure of a disease. *Stedman's Medical Dictionary*, 25$^{th}$ Edition (1990). The drug can include, for example, any substance disclosed in at least one of: *The Merck Index*, 13$^{th}$ Edition, 1998, published by Merck & Co., Rahway, N.J.; Pei-Show Juo, *Concise Dictionary of Biomedicine and Molecular Biology*. (1996); *U.S. Pharmacopeia Dictionary*. 2000 Edition; and *Physician's Desk Reference*, 2001 Edition.

As used herein, the term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

As used herein, the term "enantiomeric excess" refers to the degree to which a sample of a compound of a chiral substance contains one enantiomer in greater amounts than the other. Percent enantiomeric excess is defined as =100* ([enantiomer 1]−[enantiomer 2])/([enantiomer 1]+[enantiomer 2]).

As used herein, the term "epidermis" refers to the outer, protective, nonvascular layer of the skin of vertebrates, covering the dermis. The epidermis consists histologically of five layers, i.e., the stratum corneum, the stratum lucidum, the stratum granulosum, the stratum spinosum, and the stratum basale.

As used herein, the term "essential oil" refers to a volatile oil derived from the leaves, stem, flower or twigs of plants or synthetically-made compounds that have the same chemical attributes. The essential oil usually carries the odor or flavor of the plant. Chemically, each plant essential oil or derivative thereof, which may be extracted from natural sources or synthetically made, generally contains, as a major constituent, an acyclic monoterpene alcohol or aldehyde, a benzenoid aromatic compound containing at least one oxygenated substituent or side chain, or a monocarbocyclic terpene generally having a six-membered ring bearing one or more oxygenated substituents.

As used herein, the term "essential oil" includes derivatives thereof, including racemic mixtures, enantiomers, diastereomers, hydrates, salts, solvates, metabolites, analogs, and homologs Essential oils, their chemistry and plant families are known in the art. See, for example, S. Price, Aromatherapy Workbook-Understanding Essential Oils from Plant to Bottle, (HarperCollins Publishers, 1993; J. Rose. The Aromatherapy Book—Applications & Inhalations (North Atlantic Books, 1992); and The Merck Index (12th Ed. 1996), each of which is incorporated herein by reference.

As used herein, the term 'HLB' refers to Hydrophile-Lipophile Balance, which is an empirical expression for the relationship of the hydrophilic ("water-loving") and hydrophobic ("water-hating") groups of a surfactant.

As used herein, "latent lamellar structure" refers to lamellar structure that is not observable in a dispersion including surfactants, oil and water but becomes observable when the dispersion undergoes heating or evaporation.

As used herein, the phrase "low hydrophile-lipophile-balance (HLB) surfactant" refers to a surfactant with an hydrophile-lipophile-balance (HLB) value of less than about 10.

As used herein, the term "log P" refers to the base 10 logarithm of the n-octanol/water partition coefficient."

As used herein, the phrase "high hydrophile-lipophile-balance (HLB) surfactant" refers to a surfactant with an hydrophile-lipophile-balance (HLB) value of equal to or greater than about 14.

As used herein, the phrase "medium hydrophile-lipophile-balance (HLB) surfactant" refers to a surfactant with an hydrophile-lipophile-balance (HLB) value of equal between about 10 and about 14.

As used herein, the phrase "High $K_{ow}$ pharmacologically active compounds" refers to useful pharmacologically active compounds that have a $pK_{ow}$ value greater than about 1.5.

As used herein, the term "immersing" refers to dipping, plunging, or sinking into a liquid.

As use herein, the term "immiscible" refers to polymers that will not mix or remain mixed with each other, although at certain conditions, for example, high temperatures, they might mix, but any such mixture will typically be thermodynamically unstable and will typically separate into distinct phases at lower temperatures.

As used herein, the terms "include," "for example," "such as," and the like are used illustratively and are not intended to limit the present invention.

As used herein, the terms "individual," "host," "subject," and "patient" are used interchangeably, and refer to a mammal, including, but not limited to, primates, including simians and humans.

As used herein, the term "Infection" refers to the invasion of the host by germs that reproduce and multiply, causing disease by local cell injury, release of poisons, or germ-antibody reaction in the cells. The infection can be in a mammal (e.g., human).

As used herein, the term "lipid" refers fats and fat-derived materials. See, e.g., *Concise Chemical and Technical Dictionary*, $4^{th}$ Edition, Chemical Publishing Co., Inc., p. 704, New York, N.Y. (1986).

As used herein, the term "liquid" refers to a substance that undergoes continuous deformation under a shearing stress. See, e.g., *Concise Chemical and Technical Dictionary*, $4^{th}$ Edition, Chemical Publishing Co., Inc., p. 707, New York, N.Y. (1986).

As used herein, the term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, for example, horses, cattle, sheep, and goats, and research and domestic species, including dogs, cats, mice, rats, guinea pigs, and rabbits.

As used herein, the phrase "medium chain triglyceride oil" refers to the chemical with CAS Number 438544-49-1.

As used herein, the term "miscible" refers to two or more polymeric materials that will form a homogeneous mixture, that is, dissolve in each other. As used herein, the term "molecular weight" refers to a weight-average molecular weight, as is well known in the art.

As used herein, the term "molecular weight" refers to a weight-average molecular weight, as is well known in the art.

As used herein, the term "oil" refers to any of various lubricious, hydrophobic and combustible substances obtained from animal, vegetable and mineral matter. Suitable oils may include, for example, petroleum-based oil derivatives, for example, purified petrolatum and mineral oil. Petroleum-derived oils include, for example, aliphatic or wax-based oils, aromatic or asphalt-based oils and mixed base oils and may include, for example, relatively polar and non-polar oils. "Non-polar" oils are generally oils, for example, petrolatum or mineral oil or its derivatives, which are hydrocarbons and are more hydrophobic and lipophilic compared to synthetic oils, for example, esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase, which is used herein.

As used herein, the terms "optional" or "optionally" mean that the subsequently described event or condition may but need not occur, and that the description includes instances where the event or condition occurs and instances in which it does not.

As used herein, the term "patient" refers to a warm-blooded animal, and preferably a mammal, for example, a cat, dog, horse, cow, pig, mouse, rat, or primate, including a human.

As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications, for example, The United States Pharmacopeia describe the analytical criteria to assess the pharmaceutical acceptability of numerous ingredients of interest.

As used herein, the term "pharmacologically active agent" refers to a chemical compound, complex or composition that exhibits a desirable effect in the biological context, i.e., when administered to a subject. The term includes pharmacologically active, pharmaceutically acceptable derivatives of those active agents specifically mentioned herein, including, but not limited to, salts, esters, amides, prodrugs, active metabolites, isomers, analogs, crystalline forms, hydrates, and the like.

As used herein, the terms 'preferred' and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

It win be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the teachings of the disclosure.

As used herein, the terms "prevent," "preventative," "prevention," "protect," and "protection" refer to medical procedures that keep the malcondition from occurring in the first place. The terms mean that there is no or a lessened development of disease or disorder where none had previously occurred, or no further disorder or disease development if there had already been development of the disorder or disease.

As used herein, the term "%" or "percent" refers to weight percent (%).

As used herein, the term "polysaccharide" refers to biological carbohydrate molecules consisting of carbon (C), hydrogen (H) and oxygen (O) formed from linking saccharides through glycosidic bonds As used herein, the term "purified" compound refers to a compound that is present in a given quantity at a concentration of at least 50%, 60%, 70%, 80%, 90% and intermediate values thereof and all in weight percent (%). For example, an isolated compound may be present at 51%, 52%, 53%, 54% and the like. Preferably the compound is present at 90% to 95% and intermediate values thereof. More preferably the compound is present at 95% to 99%, and intermediate values thereof. Even more preferably the compound is present at 99% to 99.9% and intermediate values thereof. Most preferably the compound is present at greater than 99.9% of a given quantity.

As used herein, the term "skin" refers to the external tissue layer in humans and animals consisting of epidermis and dermis.

As used herein, the phrase "room temperature" refers to a temperature in the range of about 20° C. to about 30° C.

As used herein, the phrase "subcutaneous tissue layer" refers to a tissue layer located below the skin. This tissue layer is typically characterized by a loose meshwork of connective tissue, for example, collagen and elastic fibers. It is rich in small vessels, e.g., arterioles and venoles, and capillaries.

As used herein, the term "therapeutic agent" refers to any agent, which serves to repair damage to a living organism to heal the organism, to cure a malcondition, to combat an infection by a microorganism or a virus, to assist the body of the living mammal to return to a healthy state.

As used herein, the term "therapeutic composition" refers to an admixture with an organic or inorganic carrier or excipient, and can be compounded, for example, with the usual non-toxic, pharmaceutically acceptable carriers for tablets, pellets, capsules, suppositories, solutions, emulsions, suspensions, or other form suitable for use.

As used herein, the term "therapeutically effective amount" is intended to include, for example, an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example, by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, the terms "therapy," and "therapeutic" refer to either "treatment" or "prevention," thus, agents that either treat damage or prevent damage are "therapeutic."

As used herein, the phrase "therapeutic kit" refers to a collection of components that can be used in a medical treatment.

As used herein, the phrase "therapeutic dosage" refers to a dosage considered to be sufficient to produce an intended effect.

As used herein, the phrase "therapeutically effective modality" refers to a manner in which a medical treatment is performed and is considered to be sufficient to produce an intended effect.

As used herein, the term "tissue" refers to an organized biomaterial usually composed of cells.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells, which line hollow organs or body cavities).

As used herein, the term "topically active agents" refers to compositions of the present invention that are applied to skin or mucosal surfaces. Desired pharmacological results are intended at or near the site of application (contact) to a subject.

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

As used herein, the term "treatment," covers any treatment of a disease in a mammal, particularly in a human, and includes: (a) preventing the disease from occurring in a subject, which may be predisposed to the disease but has not yet been diagnosed as having it; (b) inhibiting the disease, i.e., arresting its development; and (c) relieving the disease, i.e., causing regression of the disease.

As used herein, "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar, and "nm" denotes nanometer.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible sub ranges as well as individual numerical values within that range. For example, description of a range such as 1% to 8% should be considered to have specifically disclosed sub ranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

The invention illustratively disclosed herein suitably may be practiced in the absence of any element which is not specifically disclosed herein.

The present invention provides a nanoparticle dispersion for topical delivery to skin of a mammal. The nanoparticle dispersion includes: one or more hydrophobic bioactive agents or one or more hydrophobic drugs each independently having a log P>1; one or more polyethoxylated high hydrophile-lipophile-balance (HLB) surfactants; one or more low hydrophile-lipophile-balance (HLB) surfactants each independently having a hydrophile-lipophile-balance (HLB) value less than about 10; one or more water immiscible oils; and water.

Suitable hydrophobic bioactive agents may include, for example, (1) oil soluble vitamins and provitamins such as retinol (Vitamin A), retinyl palmitate (Vitamin A), retinyl sunflowerate (Vitamin A), ascorbyl palmitate (vitamin C), tetrahexyldecyl ascorbate (vitamin C), cholecalciferol (Vitamin D3), ergocalciferol (vitamin D2), tocopherol (Vitamin E), and tocopheryl acetate (Vitamin E), phylloquinone and derivatives (Vitamin K), and coenzyme Q; (2) Essential oils extracted from plants through distillation (via steam and/or water) or mechanical methods such as cold pressing, such as frankincense essential oil, lavender essential oil, raspberry seed oil, cranberry seed oil, tomato seed oil, black cumin seed oil, hemp flower extract, hemp seed oil, tea tree essential oil, peppermint essential oil, lemongrass essential oil, *eucalyptus* essential oil, rosemary essential oil, cedarwood essential oil, clove essential oil, bergamot essential oil, arnica flower essential oil, omega-3 algae oil, blackberry seed oil, broccoli seed oil, carrot seed oil, cucumber seed oil, flaxseed oil, grape seed oil, pumpkin seed oil, pomegranate seed oil and camphor essential oil; (3) Terpenoids, diterpenoids and polyterpenoids and derivatives thereof including methyl salicylate, birch bark extract, geraniol, limonene, camphor, and menthol; (4) Cannabinoids such as cannabidiol and tetrahydrocannabinol; (5) Polyphenol compounds such as reservatrol, ellagic acid, tannic acid; and (6) Bioactive fatty acids derived from castor oil such as ricinoleic acid and undecylenic acid Preferably, the one or more hydrophobic bioactive agents are selected from the group consisting of ascorbyl palmitate, coenzyme Q, retinyl palmitate, tocopheryl acetate, birch bark extract, cannabidiol, frankincense essential oil, methyl salicylate, resveratrol, and undecylenic acid.

Suitable hydrophobic drugs may include, for example, aspirin, atropine, benzocaine, cortisol, cortisone, diclofenac, diflusinal, dronabinol, estradiol, flurbiprofen, haloperidol, hydrocortisone, ibuprofen, S-ibuprofen, ketoprofen, ketorolac, lidocaine, minoxidil, naproxen, nicotine, penicillin V, prednisone, progesterone, salicylic acid, and sulindac.

Preferably, the one or more hydrophobic drugs are selected from the group consisting of aspirin, benzocaine, hydrocortisone, ibuprofen, and lidocaine.

Suitable polyethoxylated high hydrophile-lipophile-balance (HLB) surfactants may include, for example, one or more ether type polyethoxylated high hydrophile-lipophile-balance (HLB) surfactants each independently having a hydrophile-lipophile-balance (HLB) value of equal to or greater than about 14; one or more ester type polyethoxylated high hydrophile-lipophile-balance (HLB) surfactants each independently having a hydrophile-lipophile-balance (HLB) value of equal to or greater than about 14; one or more non-polyethoxylated high hydrophile-lipophile-balance (HLB) surfactants each independently having a hydrophile-lipophile-balance (HLB) value of equal to or greater than about 14; one or more low hydrophile-lipophile-balance (HLB) surfactants each independently having a hydrophile-lipophile-balance (HLB) value less than about 10, and one or more phospholipid low hydrophile-lipophile-balance (HLB) surfactants each independently having a hydrophile-lipophile-balance (HLB) value less than about 10.

Suitable one or more ether type polyethoxylated high hydrophile-lipophile-balance (HLB) surfactants each independently having a hydrophile-lipophile-balance (HLB) value of equal to or greater than about 14 may include, for example, surfactants derived from addition of about 20 to about 100 moles of ethylene oxide to fatty alcohols such as lauryl alcohol, cetyl alcohol, oleyl alcohol, stearyl alcohol, and isotridecyl alcohol which may be referred to as alcohol ethoxylates, polyoxyethylene alkyl ethers, and polyoxyethylated fatty alcohols including laureth-23, ceteth-20, ceteareth-20, ceteareth-25, ceteareth-30, oleth-20, steareth-20, steareth-40, and steareth-100 which are available, for example, as commercial products including Brij® 123, Brij® CS20, Brij® O20, Brij® S20 and Brij® S100. Particularly preferred ether type polyethoxylated high hydrophile-lipophile-balance (HLB) surfactants include, for example, laureth-23, ceteareth-20, ceteareth-30 and steareth-40.

Preferably, the one or more ether type polyethoxylated high hydrophile-lipophile-balance (HLB) surfactants are selected from the group consisting of laureth-23, laureth-30, steareth-100, steareth-20, steareth-40, ceteareth-20, and ceteareth-30.

Suitable one or more ester type polyethoxylated high hydrophile-lipophile-balance (HLB) surfactants each independently having a hydrophile-lipophile-balance (HLB) value of equal to or greater than about 14 may include, for example, (1) Ester type polyethoxylated high hydrophile-lipophile-balance (HLB) surfactants derived from the addition of 20 to 100 moles of ethylene oxide to saturated or unsaturated fatty acids which may be referred to as polyethylene glycol carboxylates, poly(oxyethylene) carboxylates and poly(ethylene oxide) carboxylate esters including poly(ethylene oxide) laurate esters, poly(ethylene oxide) oleate esters, and poly(ethylene oxide) stearate esters, such as PEG-20 laurate, PEG-20 oleate, PEG-20 stearate, PEG-32 stearate, PEG-40 stearate, and PEG-100 stearate. Ester type polyethoxylated high hydrophile-lipophile-balance (HLB) surfactants are available, for example, as commercial products including Myrj® S40 and Myrj® S100; (2) Ester type polyethoxylated high hydrophile-lipophile-balance (HLB) surfactants derived from the addition of 20 to 100 moles of ethylene oxide to fatty acid sorbitan esters which may be referred to as polyoxyethylene sorbitan carboxylates, such as polysorbate 20, polysorbate 40, polysorbate 60, and polysorbate 80 which are available, for example, as commercial products including Tween® 20, Tween® 40, Tween® 60, and Tween® 80; (3) Ester type polyethoxylated high hydrophile-lipophile-balance (HLB) surfactants derived from the addition of 20 to 100 moles of ethylene oxide to fatty acid glycerin esters which may be referred to as polyethylene glycol glyceryl carboxylates such as PEG-30 glyceryl cocoate, poly(oxyethylene) glyceryl monolaurate and poly(oxyethylene) glyceryl monostearate, which are available, for example, as commercial products including Jeechem GL-30 and Jeechem GC-30; and (4) Ester type polyethoxylated high hydrophile-lipophile-balance (HLB) surfactants derived from the addition of 20 to 100 moles of ethylene oxide to castor oil or hydrogenated castor oil such as PEG-25 castor oi ethoxylate, PEG-40 castor oil ethoxylate, PEG-60 castor oil ethoxylate, hydrogenated PEG-25 castor oil ethoxylate, hydrogenated PEG-40 castor oil ethoxylate, and hydrogenated PEG-60 castor oil ethoxylate, which are available, for example, as commercial products including Kolliphor® RH40 and Kolliphor® RH60.

Preferably, the one or more ester type polyethoxylated high hydrophile-lipophile-balance (HLB) surfactants are selected from the group consisting of PEG100 stearate; PEG20 stearate; PEG30 glyceryl cocoate; PEG32 stearate; polysorbate 20, and polysorbate 80.

Suitable one or more non-polyethoxylated high hydrophile-lipophile-balance (HLB) surfactants each independently having a hydrophile-lipophile-balance (HLB) value of equal to or greater than about 14 may include, for example, (1) fatty ether mono-, di- and oligoglycosides containing a ether bond between a fatty alcohol and a mono-, di- and oligoglycosides, alkyl polyglucosides, and alkylpolyglycosides such as decyl glucoside, cocoglucoside, poly (D-glucopyranose) ether with (C8-C14) linear primary alcohols, and xylityl caprate/caprylate which are available, for example, as commercial products including Plantacare® 2000 UP and Giorbis GiO™-103; (2) polyglyceryl fatty acid monoesters with such as triglycerol monolaurate, tetraglycerol monolaurate, triglycerol monooleate, tetraglycerol monooleate, triglycerol monostearate, tetraglycerol monostearate; (3) mono- and di-esters of glycerin with linear or branched long chain (greater than about 8 carbon atoms) fatty acids further esterified with short chain monocarboxylic acids, for example, glycerol monostearate lactate; (4) Saturated or unsaturated, linear or branched aliphatic $C_8$ to $C_{22}$ alkyl sulfonate and sulfate compounds, for example, octanesulfonic acid, sulfuric acid ester with lauryl alcohol, and salts thereof such as sodium lauryl sulfate; (5) Saturated or unsaturated, linear or branched aliphatic $C_8$ to $C_{22}$ ethoxylated alkyl sulfonate and sulfate compounds, for example, sulfuric acid ester with the product of addition of four moles of ethylene oxide to lauryl alcohol, and salts thereof such as sodium laureth sulfate; (6) sulfonated succinic acid esters with saturated or unsaturated, linear or branched aliphatic $C_6$ to $C_{22}$ alcohols, for example, the bis(2-ethylhexyl) ester of sulfosuccinic acid and the lauryl poly(ethylene oxide) ester of sulfosuccinic acid, or a mixture of these surfactants; (7) esters of lactic acid or lactic acid oligomers with fatty acids and salts thereof such as sodium stearoyl-2-lactylate; (8) sulfonates of benzene, cumene, toluene and alkyl substituted aromatic compounds and salts thereof, for example, dodecyl benzene sulfonic acid, or a mixture of these surfactants; (9) carboxylates of alcohol ethoxylates, alcohol propoxylates, alcohol ethoxylate propoxylates and ethoxylated linear and branched alkylphenol compounds and salts thereof, for example, poly(ethylene oxide) tridecyl alcohol ether carboxylic acid and sodium poly(ethylene oxide) lauryl ether carboxylate, or a mixture of these surfactants; (10) long chain (greater than about 8 carbon atoms) acyl amino acids, for example, acyl glutamates, acyl peptides, acyl sarcosinates, acyl taurates, salts thereof, and mixtures of these surfactants; (11) Saturated or unsaturated, linear or branched aliphatic $C_8$ to $C_{22}$ alkyl amido propyl (dimethyl ammonio) acetate compounds, for example, lauramidopropyl betaine and stearamidopropyl betaine, and mixtures of these surfactants; (12) Sophorolipids, which consist of a hydrophobic fatty acid tall of a hydroxylated 16 or 18 carbon atom fatty acid, which is β-glycosidically linked to a hydrophilic sophorose head, including free acid (open) and internally esterified (lactonic) forms and acetylated forms (acetylated on the 6'- and/or 6"-positions). Sophorolipids useful in the practice of this invention include, for example, product mixtures produced by yeasts, for example, *Candida bombicola, Candida apicola, Starmerella bombicola*, and *Candida sp*. NRRL Y-2720 (as identified by Price et al., *Carbohydrate Research,* 348 (2012) 33-41) and chemically modified product mixtures; and (13) Rhamnolipids including mono-rhamnolipids, which consist of one or two 3-(hydroxyalkanoyloxy) alkanoic acid tails and a single rhamnose head and di-rhamnolipids, which consist of one or two 3-(hydroxyalkanoyloxy) alkanoic acid tails and two rhamnose heads, including mixtures of compounds produced by *Pseudomonas* and *Burkholderia* bacterial species, for example, *Pseudomonas aeruginosa* and *Burkholderia plantarii.*

Preferably, the one or more non-polyethoxylated high hydrophile-lipophile-balance (HLB) surfactants selected from the group consisting of cocoglucoside, decyl glucoside, xylityl caprate/caprylate and sodium laureth sulfate.

Suitable one or more low hydrophile-lipophile-balance (HLB) surfactants each independently having a hydrophile-lipophile-balance (HLB) value less than about 10 may include, for example, (1) Fatty acid esters including saccharide residues including sorbitan monolaurate, sorbitan monopalmitate, sorbitan stearate, sorbitan oleate, sorbitan isostearate, sorbitan sesquioleate, sorbitan trioleate, and sorbitan tristearate, which are available, for example, as commercial products including Span® 120, Span® 20, Span® 60, Span 80, Span® 83, and Span® 85; (2) fatty acid glycerides, for example, glycerol monooleate, glyceryl monostearate, glycerol dioleate, glycerol distearate, which are available, for example, as commercial products including Jeechem GMS-D and Jeechem GMIS; (3) fatty alcohol ethoxylates, fatty alcohol propoxylates, and fatty alcohol ethoxylate propoxylates for example, oleth-2, ceteareth-2, and lauryl alcohol 3 mole ethoxylate/6 mole propoxylate, which are available, for example, as commercial products including Brij® L4, Brij®O5, Brij®S2, and Alkomol® L 306; and (4) Saturated or unsaturated, linear or branched aliphatic $C_8$ to $C^{22}$ carboxylic acid functional compounds including fatty acids derived from the saponification of vegetable and animal fats and oils, for example, octanoic acid, coconut fatty acid, oleic acid, ricinoleic acid, stearic acid, and carboxylic acid terminated short chain (e.g., n=4) polymers of ricinoleic acid and mixtures of such surfactants.

Preferably, the one or more low hydrophile-lipophile-balance (HLB) surfactants selected from the group consisting of stearic acid, octanoic acid, glyceryl monostearate, sorbitan oleate, and sorbitan stearate.

Suitable one or more phospholipid low hydrophile-lipophile-balance (HLB) surfactants each independently having a hydrophile-lipophile-balance (HLB) value less than about 10 may include, for example, phosphatidyl choline, phosphatidylethanolamine, and phosphatidylinositol and compositions which include mixtures of these, for example, lecithins. Phospholipid products are available, for example, as commercial products including Phospholipon® 90G, Phospholipon® 90H, Alcolec® XTRA-A, Alcolec® PC 75 and Sunlipon® 65.

Preferably, the one or more phospholipid low hydrophile-lipophile-balance (HLB) surfactants selected from the group consisting of phosphatidylcholine and lecithin.

The nanoparticle dispersion may also include, for example, one or more oil soluble vitamin and provitamns. Preferably, the one or more oil soluble vitamin and provitamins are selected from the group consisting of ascorbyl palmitate and tocopheryl acetate.

The nanoparticle dispersion may also include, for example, one or water soluble polymers or gums, including: (1) Polysaccharides such as dextrins, gums, including maltodextrin, cyclodextin, hyaluronic acid, xanthan gum, guar gum, and water dispersible or water-soluble starches; (2) Water soluble cellulose derivatives including cellulose ethers such as methyl cellulose, carboxymethyl cellulose, hydroxypropyl methyl cellulose, and carboxyethyl cellulose; (3) Poly(acrylic) acid and salts thereof including Carbomer 940, and sodium carbomer such as Neutragel DA (product of 3V Sigma USA, Georgetown S.C.); (4) Acrylates/Vinyl Crosspolymers such as Rapidgel EZ1 (product of 3V Sigma USA); and (5) Poly(vinyl pyrrolidone).

Preferably, the one or more water soluble polymers or gums are selected from the group consisting of methyl cellulose, sodium carbomer, and acrylates/vinyl crosspolymers.

The nanoparticle dispersion may also include, for example, one or more cryoprotectants that prevent the freezing of nanoparticle dispersions, or prevents decomposition of nanoparticle dispersions during freezing. Preferred cryoprotectants are water miscible or water soluble compounds including glycerin, propylene glycol, ethylene glycol, diethylene glycol, diethylene glycol ethyl ether, sucrose, sorbitol, trehalose, and dimethyl sulfoxide (DMSO).

Preferably, the one or more cryoprotectants are selected from the group consisting of diethylene glycol, dimethyl sulfoxide, ethylene glycol, glycerin, propylene glycol, sorbitan, and trehalose.

The nanoparticle dispersion may also include, for example, one or more additives such as antioxidants, chelating agents, acidulants, and antimicrobial agents. Useful antioxidants include, for example, butylated hydroxyl toluene (BHT) and mixed tocopherols. Useful chelating agents include, for example, phosphates, ethylenediaminetetraacetic acid and salts thereof, sodium phytate, and nitrilotriacetic. Useful antimicrobial agents include, for example, phenoxy ethanol and caprylyl glycol such as Optiphen, product of Ashland Chemicals and Jeechem CAP-4, product of Jeen.

Preferably, the one or more additives are selected from the group consisting of tetrasodium ethylenediaminetetraacetic acid, citric acid, butylated hydroxytoluene, and sodium chloride.

Processing surfactant-oil-water compositions using a modified hot melt extruder: Although lipidic nanoparticles including liposomes, niosomes, nanostructured lipid carriers (NLCs), solid lipid nanoparticles (SLNs), and lipid nanocarriers (LNCs) have been widely investigated as drug delivery vehicles for routes of administration including, oral, intravenous, transmucosal, and dermal, processing such compositions has been problematic, especially for processes which include a particle comminution step and especially at higher particle concentrations. Consequently, commercial development of lipidic nanoparticle dispersions is limited, and commercial products of lipidic dispersions with volume average particle size less than 150 nm and nanoparticle concentrations greater than 25 percent are unknown, and examples in the scientific literature are rare. Typical methods for making nanoparticle dispersions by comminution include, for example, high pressure homogenization, sonication, and forcing larger particle size dispersions through filters or miroporous channels, which may be referred to as extrusion. Literature examples of the preparation of more highly concentrated lipidic nanoparticle dispersions include aggressive particle comminution by high pressure homogenization as described by Müller et al. (*Adv. Drug Deliv. Rev.,* 54 Suppl. 1 (2002) S131-S155). According to Müller, dispersions of solid lipid nanoparticles can be made by high pressure homogenization but as the lipid concentration exceeds 25 weight percent, the volume average particle size increases to values above 150 nm and the dispersions are no longer liquid or paste-like, they are solids that can be cut with a knife and are therefore of less interest for topical administration. Techniques such as high pressure homogenization and ultrasonication based on the use of large mechanical forces typically involve multistep processing, long processing time and frequent failures due to the presence of large particles and metal contamination (Puglia et al., *Expert Opin. Drug Deliv.* 9 (2012) 429-441. doi: 10.1517/17425247.2012.666967).

Lipidic nanoparticle dispersions can also be made by processes that do not involve comminution such as the so-called microemulsion process (which may also referred to as phase inversion emulsification or PIT emulsification) and solvent displacement, however such nanoparticle dispersions as prepared require an additional process step to remove solvent or excess water. The as prepared nanoparticle dispersions have unacceptably low particle concentrations, especially for topical applications (Montenegro et al., *J Drug Deliv Sci Technol* Volume 32, Part B, April 2016, Pages 100-112 https://doi.org/10.1016/j.jddst.2015.10.003).

The United States Food and Drug Administration supports the implementation of continuous processing, defined as those where material is simultaneously charged and discharged from the process, as opposed to batch processes, where all materials are charged before the start of processing and discharged at the end of processing. Processes with particle comminution, solvent displacement, and PIT emulsification are batch processes subject to batch to batch variations. Recently, however, researches have shown the possibilty of producing lipid nanoparticle dispersions continuously by combination of hot-melt extrusion technology and sonication (Bhagurkar et al., *J. Pharm. Sci.* 106 (2017) 1085-1091. doi:10.1016/J.XPHS.2016.12.015) and by combination of hot-melt extrusion and high pressure homogenization (Patil et al., *Int. J. Pharm.* 471 (2014) 153-156. doi:10.1016/J.IJPHARM.2014.05.024). Although these processes are capable to be continuous, they are multi-step and it is required to match the input and output rates of separate steps. Furthermore, the final processing step in each of these hot melt extrusion methods is particle comminution, which is subject to the same constraints and issues of sonication and high pressure homogenization as described above.

Surprisingly, we have found that highly concentrated dispersions with up to 60 weight percent dispersed nanoparticles and volume average particle size as low as about 25 nm can be made by a single step process using a twin screw extruder modified so as to provide a temperature gradient of greater than about 35° C. for surfactant-oil-water composition conveyed through it. Processing times for the conversion of a coarse, non-nanoparticle dispersion to a final concentrated nanoparticle dispersion can be less than 2 minutes which is remarkable considering that time and temperature cycling have been shown to be important for making nanoparticle dispersions by phase inversion methods (Heurtault et al., *Pharm. Res.* 19, 875, 2002 and Anton et al., *Int J Pharm.* 2007 Nov. 1; 344(1-2):44-52). Processing can be done at rates up to about 380 grams per minute using pilot scale twin screw extruders with 24 mm or 27 mm screw diameters. Preferably, surfactant-ol-water compositions are those which form lamellar microemulsions between about 75° C. and about 100° C., which are preferably processed with temperature gradients that include, for example, the temperature at which the composition is a microemulsion. The temperature gradient during processing can be provided by pre-heating the composition prior to introduction to the extruder or by heating in one or more of the first temperature control zones of the extruder, or both plus cooling the composition in one or more of the latter temperature zones of the extruder. In preferred embodiments, the process ΔT defined as the difference between the maximum of the composition temperature as introduced to the extruder and the extruder zone temperature minus the minimum temperature of the cooled extruder zones is greater than about 35° C., greater than about 50° C., and greater than about 60° C.

Heating of surfactant-oil-water for compositions processing can be done in bulk, as for example, using a beaker with a hot plate/stirrer or a temperature controlled vessel such as a Gigawort™ electric boil kettle, by using a heat exchanger, or by heating in one or more of the first temperature control zones of the extruder. In preferred embodiments, pre-heating the surfactant-oil-water composition with a heat exchanger before introduction into the extruder is preferred because it provides the advantage of short heat exposure in the case of temperature sensitive ingredients and minimizes heating of downstream extruder temperature zones caused by contact with upstream, heated extruder zones. In preferred embodiments, surfactant-oil-water compositions are preheated with a heat exchanger prior to introduction to an extruder in which none of the temperature control zones are heated.

In the art of hot melt processing of polymers, a variety of screw elements are known which have purposes including conveying, kneading, mixing and shearing. For processing surfactant-oil-water according to the present invention, screw elements are preferably selected primarily from conveying elements, for example, greater than about 50 percent conveying elements or greater than about 75 percent conveying elements, so long as sufficient mechanical mastication is provided so as to give nanoparticle dispersions. Failure to provide sufficient mechanical mastication results in production of coagulated, non-nanoparticle dispersions. Useful conveying elements include, for example, free cut conveying elements characterized by the presence of free volume between crests and opposing screw elements. It is preferred that a portion of the conveying screw elements are intermeshing as opposed to free cut in order to provide mechanical mastication. Preferably, conveying screw elements have a ratio between the crest and root of the screw greater than about 1.2, greater than 1.5 or greater than about 2.0 to a give greater fluid flow cross sectional area and higher material throughput. Particularly preferred screw elements are intermeshing conveying elements with crest to root ratios greater than 1.2.

Selection of polyethoxylated high hydrophile-lipophile-balance (HLB) surfactants: Use of relatively longer chain poly(ethylene oxide) surfactants in a process of phase inversion resulting from a change in temperature is described in U.S. Pat. No. 6,221,370. Typically phase inversion processes require polyethoxylated surfactants which have the property of decreasing hydrophilicity with increasing temperature. According to U.S. Pat. No. 6,221,370 Examples F1-F3, compositions including an ester type polyethoxylated high hydrophile-lipophile-balance (HLB) surfactant (palmitic/stearic acid+30 moles of ethylene oxide) were processed using a phase inversion temperature (PIT) emulsification method to give dispersions that were stable when stored for 4 weeks at 40° C. If the ester type polyethoxylated surfactant was replaced with an ether type polyethoxylated high hydrophile-lipophile-balance (HLB) surfactant (cetearyl alcohol+ 30 moles of ethylene oxide, Example F4) the processed dispersions are not stable.

Previously, it was found that, through a process of phase inversion, a composition with ibuprofen which included an ether type polyethoxylated high hydrophile-lipophile-balance (HLB) surfactant could give concentrated nanoparticle dispersions that are stable at 40° C. but compositions with ibuprofen and ester type polyethoxylated high hydrophile-lipophile-balance (HLB) surfactants gave large particle size, non-nanoparticle dispersions that are unstable. These results are the opposite of those from U.S. Pat. No. 6,221,370. It appeared that including ibuprofen, an organic compound with a carboxylic acid group, negated the need for the ester group, a carboxylic acid group residue, in the polyethoxylated high hydrophile-lipophile-balance (HLB) surfactant. Subsequently, it has been discovered that the requirement for ether type and not ester type polyethoxylated surfactants in order to obtain stable dispersions is not limited to compositions that contain ibuprofen, it also applies to ibuprofen free compositions with other hydrophobic drugs that have carboxylic acid groups and carboxylic acid group residues including diclofenac (carboxylic acid), aspirin (carboxylic acid and ester), and lidocaine (ester), and to ibuprofen free compositions that include, for example, drugs with no carboxylic acid group residues (hydrocortisone). In preferred embodiments of the present invention concentrated nanoparticles are prepared that are free of ibuprofen and S-ibuprofen. This surprisingly also applies to compositions without hydrophobic drugs as well. Surprisingly, a modified twin screw extruder can be used to prepare stable, highly concentrated nanoparticle dispersions through reactions characterized by phase inversion where the compositions contain ether type polyethoxylated high hydrophile-lipophile-balance (HLB) surfactants but not ester type polyethoxylated high hydrophile-lipophile-balance (HLB) surfactants, the opposite of what is useful in preparing stable PIT emulsions according to U.S. Pat. No. 6,221,370. By using ether type polyethoxylated high hydrophile-lipophile-balance (HLB) surfactants and a modified twin screw extruder, it is possible to prepare highly concentrated nanoparticle dispersions with volume average particle size less than 150 nm which include many hydrophobic active ingredients such as hydrophobic drugs, oil soluble vitamins and provitamins, and botanical extracts whether or not the compositions include, for example, ibuprofen or other compounds with carboxylic acid group residues.

Owing to their commercial importance, the phase behavior of ether type polyethoxylated surfactants has been studied in detail, and a key feature of these surfactants is their self-assembling and structuring behavior in aqueous compositions. The structuring behavior gives rise to many different phases depending upon concentration, temperature and the presence or absence of water immiscible oils. At higher concentrations, ether type polyethoxylated high hydrophile-lipophile-balance (HLB) surfactants form phases including liquid crystalline (LC), hexagonal, and cubic phases which exhibit marked gel-Ike properties and extraordinarily high viscosity [see, e.g., Kunieda et al., Highly Concentrated Cubic-Phase Emulsions: Basic Study on D-Phase Emulsification using isotropic Gels. *J Oleo Sci* 50(8):633-639 •January 2001]. The tendency towards highly structured phases and high viscosity can be remarkably reduced if a carbonyl (C=O) group is inserted into ether type polyethoxylated high hydrophile-lipophile-balance (HLB) surfactants (see, e.g., Spiering et al., Changes in Phase Behavior from the Substitution of Ethylene Oxide with Carbon Dioxide in the Head Group of Nonionic Surfactants. *ChemSusChem*. 2019, Nov. 25. doi:10.1002/cssc.201902855. [Epub ahead of print]), however the presence of a carbonyl group (from a carboxylic acid residue) in ester type polyethoxylated high hydrophile-lipophile-balance (HLB) surfactants is apparently the reason that compositions with ester type polyethoxylated high hydrophile-lipophile-balance (HLB) surfactants fail to give nanoparticle dispersions when processed with a modified twin screw extruder (compare Examples 10-13 with Examples 5-9 and Example 18 with Example 17).

Although Important for nanostructure and nanoparticle development, the rich phase behavior of ether type polyethoxylated surfactants is problematic for processing because of the formation of highly viscous phases. Because the surfactant-oil-water mixtures pass through complex, high viscosity intermediate phases, there is a need for constant positive mechanical provided by kneading or mastication during the process. It is for this reason that simply cooling surfactant-oil-water mixtures with a conventional plate type or concentric tube type heat exchanger gives coagulated, large particle size emulsions rather than nanoparticle dispersions. It has been found that a modified twin screw extruder in which the majority of screw elements are conveying elements with a minor fraction of mixing or kneading screw elements is capable to provide sufficient mechanical kneading and mastication during phase transformations so as to provide concentrated nanoparticles in the extrudate.

Support for the conclusion that structure formation during phase changes is responsible for fine particle size in extruded dispersions is provided by the observation that adding structure promoting additives allows the use of ester type polyethoxylated high hydrophile-lipophile-balance (HLB) surfactants in the practice of the current invention. It has been found to be possible to compensate for the inadequate structure forming properties of ester type polyethoxylated high hydrophile-lipophile-balance (HLB) surfactants by adding structure forming low hydrophile-lipophile-balance (HLB) surfactants as additives. Particularly useful structure forming low hydrophile-lipophile-balance (HLB) surfactants are phospholipids. Examples 19-23 show that by adding phospholipids to compositions with ester type polyethoxylated high hydrophile-lipophile-balance (HLB) surfactants that alone do not give nanoparticle dispersion. It is possible to obtain useful and stable nanoparticle dispersions. Useful phospholipids include, for example, dioleyl phosphatidyl choline, distearoyl phosphatidyl choline, and lecithin.

Skin permeation of concentrated nanoparticle dispersions: A challenging problem is maximizing bioavailability of drugs in topical products. Research shows that skin permeation of drugs is promoted by surfactants, including polyethoxylated surfactants. In the case of ether type polyethoxylated surfactants, permeation is high for relatively shorter poly(ethylene oxide) chains but diminishes for longer chains. For example, in the case of polyethoxylated oleyl alcohols used to promote permeation of ibuprofen across human skin, oleth-2 (HLB=5.2) was the most effective permeation enhancer and oleth-20 (HLB=15.6) was the worst (Walters et al., Int J Cosmet Sci. 1993 December; 15(6):260-71). Similarly, the permeation of methyl nicotinate across hairless mouse skin was 4 to 5 times greater for ceteth-8 (HLB=10.8) than for ceteth-20 (HLB=15.9) or ceteth-30 (HLB=17.1) and skin permeation of piroxicam in live guinea pigs measured as the AUC (area under the curve for plasma concentration) was optimal for ether type polyethoxylated surfactants when the chain lengths were between 10 and 15 units, dropping to essentially zero for chain lengths greater than 20 (Park et al., Int J Pharm. 2000 Nov. 19; 209(1-2):109-19).

On the other hand, for phase stability of concentrated nanoparticle dispersions made using a modified twin screw extruder which contain polyethoxylated high hydrophile-lipophile-balance (HLB) surfactants, it is believed that the average chain length poly(ethylene oxide) chain length must be greater than about 20 and for some compositions including those with ibuprofen, the chain length must be greater than about 30 in order to keep the temperature of phase transitions well above storage conditions thus avoiding phase separation. Surprisingly, it has been found that polyethoxylated surfactants with number average chain length greater than 30 provides excellent skin permeation of ibuprofen when present as constituents of nanoparticles. High permeation is attributable to the structure and properties of the ensemble of the polyethoxylated surfactant and other components which is the nanoparticle.

An important attribute of highly permeating nanoparticles is polydispersity in hydrophile-lipophile-balance (HLB) surfactant values. Hydrophile-lipophile-balance (HLB) polydispersity promotes formation of lamellar structures for nanoparticles which otherwise have no layer structures as prepared when they are applied to skin. Layered structures have been shown to be important for promoting dermal permeation of nanoparticles, for example, in liposomes and niosomes. Hydrophile-lipophile-balance (HLB) polydispersity can be calculated as the hydrophile-lipophile-balance (HLB) weight mean square deviation, $WMSD_{HLB}$ which is the sum of the products of the weight fraction of the i-th surfactant species times the square of the deviation of the hydrophile-lipophile-balance (HLB) of the i-th surfactant species from the weight average hydrophile-lipophile-balance (HLB) divided by the weight average hydrophile-lipophile-balance (HLB) hydrophile-lipophile-balance (HLB) polydispersity with $WMSD_{HLB}$ greater than about 1.5 is required to support development of lamellar structures subsequent to skin application for dispersions of nanoparticles with no layered structure as prepared. At high values of $WMSD_{HLB}$, nanoparticles with aqueous cores may form including multi-layered structures which are undesirable. In preferred nanoparticle dispersions, nanoparticles have oily cores and $WMSD_{HLB}$ is between about 1.5 and about 4.5, between about 1.75 and about 3.5, and between about 2 and about 3.

Figure 3:
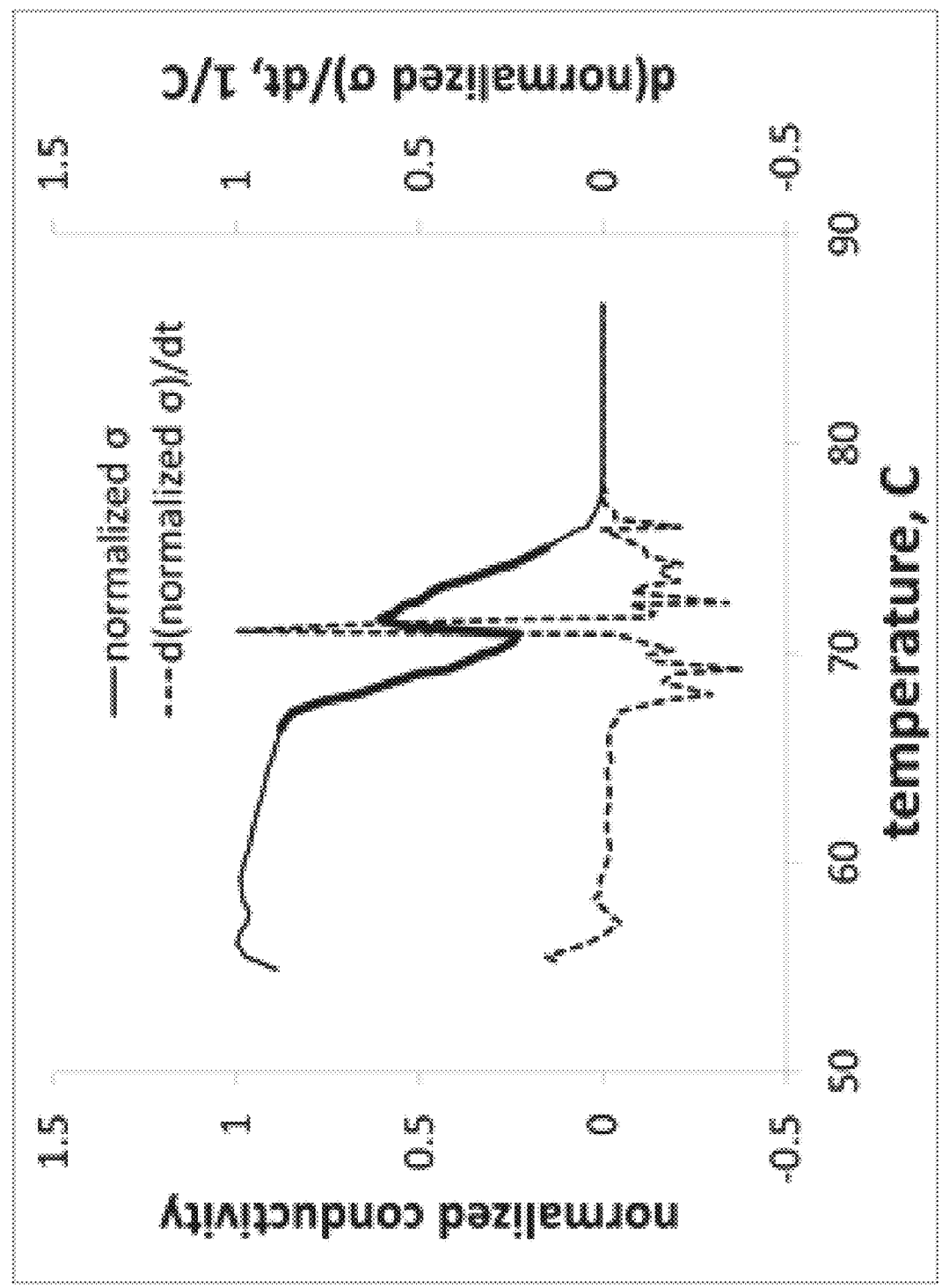
FIG. 3 is a plot of normalized conductivity vs temperature and first derivative of conductivity vs temperature for the nanoparticle dispersion of Example 19.
Figure 5:
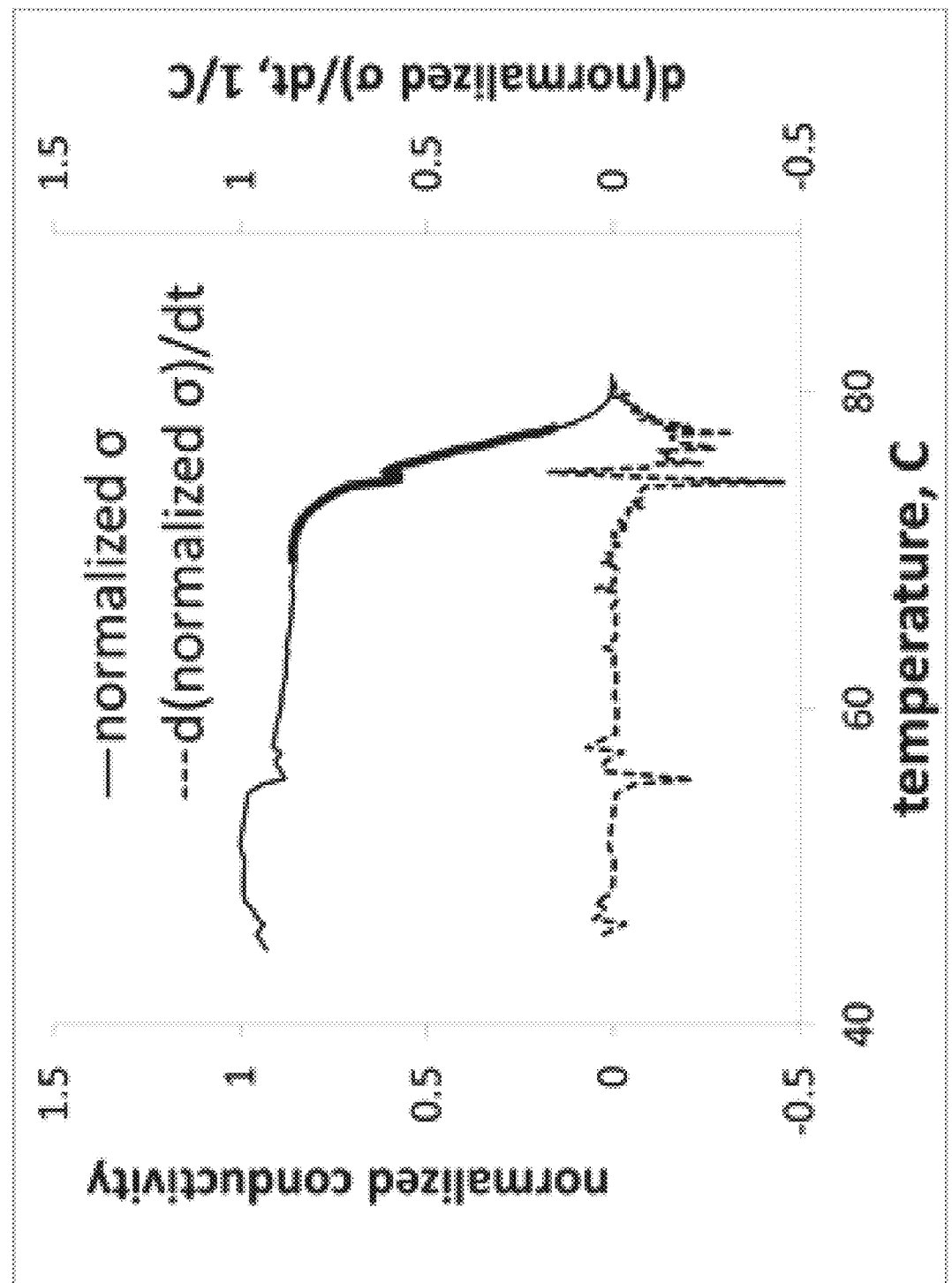
FIG. 5 is a plot of normalized conductivity vs temperature and first derivative of conductivity vs temperature for the nanoparticle dispersion of Example 55.

Preferred nanoparticle dispersions have latent lamellar structure, that is, the propensity for nanoparticle dispersions without lamellar structure to develop lamellar structure. Latent lamellar structure can be evaluated by inducing changes in nanoparticle dispersions such as by evaporation or heating and observing for characteristics of lamellar structures such as optical birefringence and electrical impedance. Optical birefringence can be observed by viewing through crossed polarized films. Electrical impedance can be observed as a negative peak in a plot of conductivity versus temperature and a corresponding positive peak in the first derivative plot of conductivity vs temperature for heated and stirred nanoparticle dispersions when heating at a rate of between 1 and 4° C. per minute and measuring conductivity with an open cell geometry electrode such as a 013005MD 4-cell conductivity electrode available from Thermo Scientific. FIGS. 3 and 5 are plots of normalized conductivity (that is, instantaneous conductivity divided by the maximum conductivity) versus temperature and the first derivative curve of normalized conductivity versus temperature for the nanoparticle dispersions of Example 19 and Example 55, respectively which show that these samples have latent lamellar structure. The presence of latent lamellar structure in heated or evaporated nanoparticle dispersions can also be discerned as layer spacing (d-spacing) from small angle x-ray scattering (SAXS) or from neutron diffraction in samples as described by Wu et al., *Biomed Spectrosc Imaging*, vol. 5, no. s1, pp. S45-S54, 2016, and by Gvaramia et al., *J. Colloid Interface Sci.* 525 (2018) 161-165). Layered structures in heated or evaporated compositions can also be observed directly by cryogenic scanning electron microscopy as described by Lee et al., *Langmuir*, 2014, Sep. 16; 30(36):10826-33. DOI: 10.1021/la502207f. Preferred nanoparticle dispersions exhibit one or more attributes of latent lamellar structure upon heating including birefringence, a negative peak in the plot of conductivity versus temperature, or a positive peak in the first derivative plot of normalized conductivity versus temperature with a peak amplitude greater than about 0.1 $C^{-1}$. The nanoparticle dispersions of Examples 4, 16, 19, 23, 38, 51, 55 and 57 were shown to exhibit one or more of these characteristics.

The ability of nanoparticles to permeate skin is known to be related to particle size, with generally better permeation for smaller particles. The appropriate quantity for particle size in a distribution of particles as it relates to dermal permeation is the weight average particle diameter because it defines the average on the basis of mass fractions of nanoparticles with a particular diameter and what matters is the mass fraction of nanoparticles that have sufficiently small diameters so as to effectively permeate skin. By comparison, an unspecified majority by mass fraction of particles can have diameters much greater than the number average particle diameter, making number average particle diameter a poor metric for permeability. Preferred nanoparticle dispersions have volume average particle diameter less than 150 nm, less than about 100 nm, and less than 50 nm.

Figure 6:
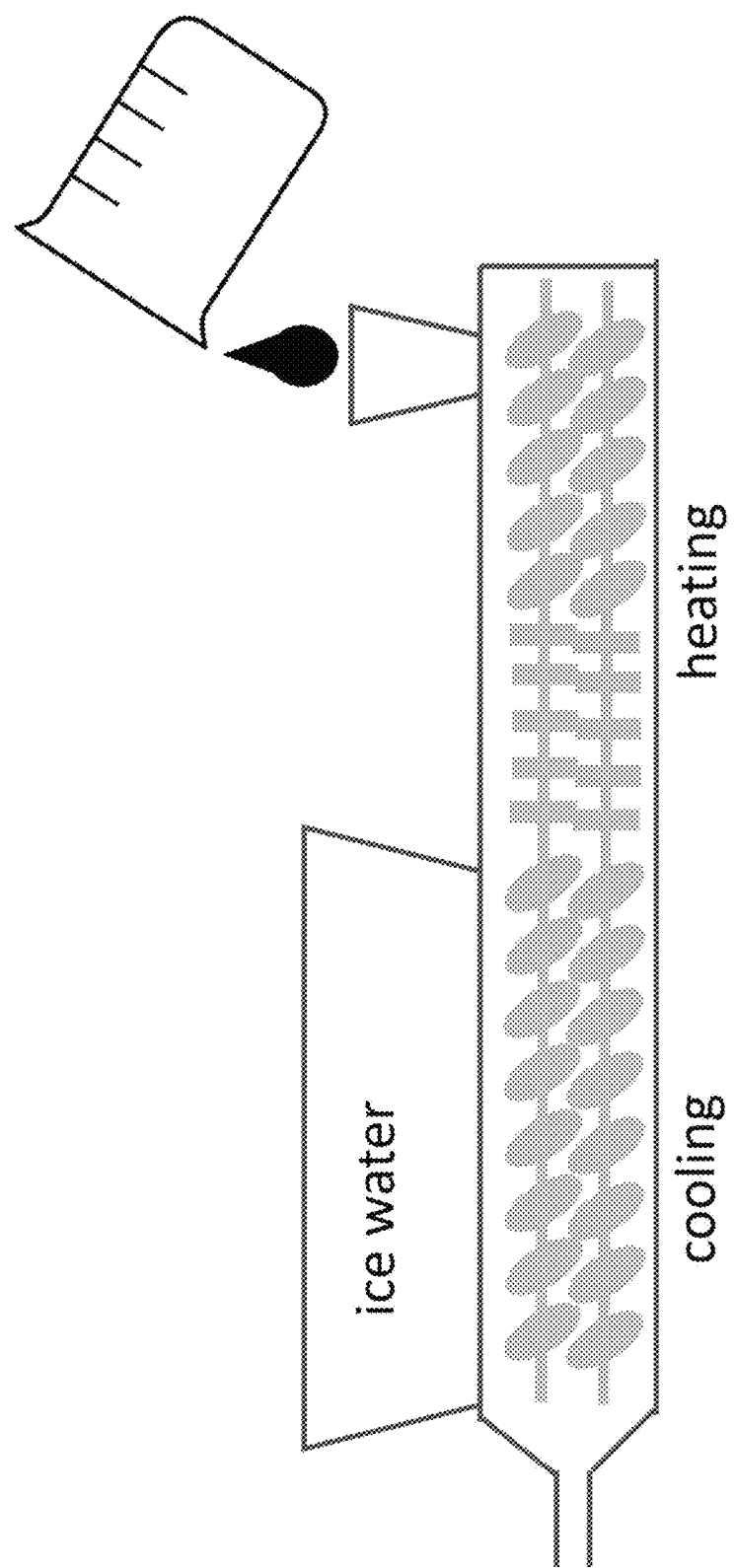
FIG. 6 is a diagram illustrating an exemplary method of using an exemplary modified twin screw extruder with a cooling reservoir.
Figure 7:
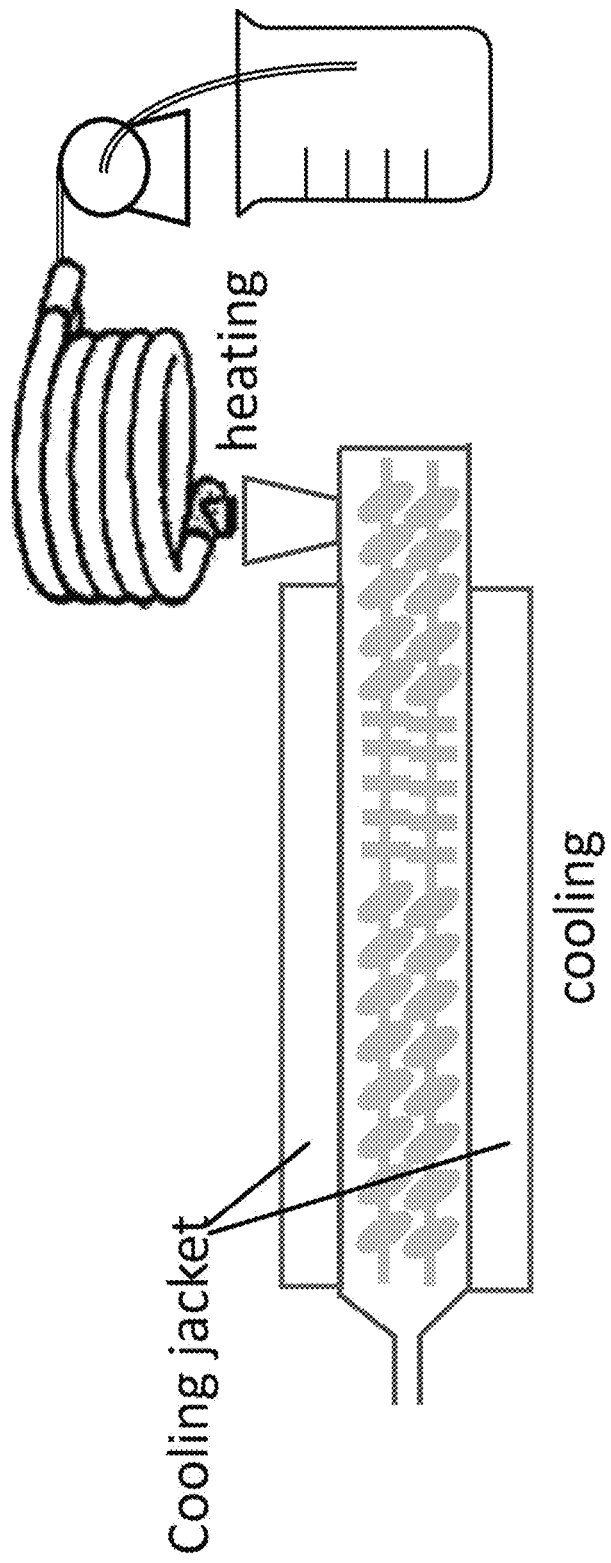
FIG. 7 is a diagram illustrating an exemplary method of using an exemplary modified twin screw extruder with a heat exchanger.

Regarding the hot-melt extruder used in preparing the nanoparticle dispersions described herein, FIG. 6 shows a modified twin screw extruder configured so as to provide heating in upstream temperature zones and cooling in downstream temperature zones. FIG. 7 shows a twin screw extruder modified so as to provide cooling throughout the majority of the extruder barrel, and in which none of the extruder temperature zones is heated. The mill base can be provided heated to an extruder modified so as to cool throughout the majority of the barrel by pre-heating either in bulk or using a heat exchanger as shown in FIG. 7. For the purposes of providing greater cooling to the extruder barrel, the cooling fluid flow path can preferably be enlarged, for example by changing fittings and hose connections in the original extruder equipment to fittings and hose connections with larger internal diameters.

The invention should now be illustrated with the following non-limiting examples. All chemicals were of reagent grade and distilled and deionized water was used. Unless otherwise indicated, all parts and percentages are by weight and all molecular weights are weight average molecular weight. Unless otherwise specified, al chemicals used are commercially available from, for example, Sigma-Aldrich (St. Louis, Mo.).

EXAMPLES

Unless otherwise indicated, all numbers expressing quantities of ingredients, properties such as molecular weight, reaction conditions, and so forth used in the specification and claims are to be understood as being modified in al instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

| ABBREVIATIONS, DESCRIPTIONS, AND SOURCES OF MATERIALS | |
|---|---|
| Description of Material | Sources of Material |
| ascorbyl palmitate | Making Cosmetics, Redmond, WA Solaray, Park City, UT |

| ABBREVIATIONS, DESCRIPTIONS, AND SOURCES OF MATERIALS | |
|---|---|
| Description of Material | Sources of Material |
| Liposomal Vitamin C | Making Cosmetics, Redmond, WA |
| BHT | Solaray, Park City, UT |
| citric acid | Making Cosmetics, Redmond, WA |
| | BME Lab and Science, Roseville MN |
| cannabidiol | Hemp Acres, Waconia, MN |
| | Mile High Labs, Broomfield, CO |
| ceteareth-20 | Making Cosmetics, Redmond WA |
| | Lotioncrafter, Eastsound WA |
| | Jeen International Corporation, Fairfield, NJ |
| ceteareth-30 | Jeen international Corporation, Fairfield, NJ |
| tetrasodium EDTA | Making Cosmetics, Redmond WA |
| capric/caprylic triglyceride oil | Making Cosmetics, Redmond WA |
| ibuprofen | BASF, Florham Park, NJ |
| isopropyl myristate | Making Cosmetics, Redmond, WA |
| | Lotioncrafter, Eastsound, WA |
| | Jeen International Corporation, Fairfield, NJ |
| | Soaper's Choice, Des Plaines, IL |
| laureth-23 | Making Cosmetics, Redmond, WA |
| | Lotioncrafter, Eastsound, WA |
| | Jeen International Corporation, Fairfield, NJ |
| lidocaine hydrochloride | onlinelidocain.com |
| | Medical Numbing Agents, Scottsdale AZ |
| limonene | Nature's Oil, Aurora, OH |
| | EcoClean Solutions, Copaigue, NY |
| medium chain triglyeride oil | BASF, Florham Park, NJ Soaper's Choice, Des Plaines, IL |
| light mineral oil (Drakeol 7) | CQ Concepts, Ringwood, IL |
| sodium chloride | Fisher Scientific, Waltham MA, |
| PEG100 stearate | BASF, Florham Park, NJ |
| | Jeen International Corporation, Fairfield, NJ |
| | Sigma Aldrich, Milwaukee, WI |
| Phospholipon 90G | Lipoid USA, Newark, NJ |
| stearic acid | Making Cosmetics, Redmond, WA |
| | Soaper's Choice, Des Plaines, IL |
| sorbitan oleate | Sigma Aldrich, Milwaukee, WI |
| sorbitan stearate | Making Cosmetics, Redmond, WA |
| | Lotioncrafter, Eastsound, WA |
| | Jeen International Corporation, Fairfield, NJ |
| tocopheryl acetate | Making Cosmetics, Redmond WA |
| | Lotioncrafter, Eastsound, WA |
| | Alcolec XTRA-A |
| lecithin | American Lecithin, Oxford, CT |

Example 1

Preparation of a concentrated Non-Nanoparticle Lipid Dispersion Including Sorbitan Oleate, Laureth-23, PEG-100 Stearate, Dioleyl Phosphatidyl Choline, Isopropyl Myristate, d-Limonene, Ibuprofen, and Medium Chain Triglyceride Oil A mill base was prepared consisting of about 3.1 weight percent (wt. %) sorbitan oleate (Sigma Aldrich, Milwaukee, Wis.), about 0.5 weight percent (wt. %) dioleyl phosphatidyl choline (Phospholipon 90G, Lipoid USA, Newark N.J.), about 1.0 weight percent (wt. %) of medium chain triglyceride oi (BASF Kollicream MCT 70. BASF, Florham Park, N.J.), about 6.2 weight percent (wt. %) laureth-23 (Lotioncrafter, Eastsound, Wash.), about 4.6 weight percent (wt. %) PEG 100 stearate (Sigma Aldrich, Milwaukee, Wis.), about 20.5 weight percent (wt. %) Isopropyl myristate (Lotioncrafter, Eastsound, Wash.), about 5.2 weight percent (wt. %) ibuprofen (BASF, Florham Park, N.J.), about 5.2 weight percent (wt. %) d-limonene (Nature's Oil) and about 53.7 weight percent (wt. %) water. The weight mean square deviation of the surfactants, $WMSD_{HLB}$, (neglecting Phosphlipon 90G) was 1.78. The sample was an opaque white liquid which upon dilution and analysis by dynamic light scattering had volume average particle diameter about 797.0 nm and number average particle diameter about 334.0 nm. When heated to about 90° C. and allowed to cool while stirring in a 50 mL beaker with a magnetic stirrer, about a 25 gram sample of the composition was observed without magnification between cross polarized films to be transparent and birefringent between about 79° C. and about 84° C.

The microemulsion composition was heated to about 83° C. and kept hot by intermittent heating using a hand held propane gas torch and was fed into a Thermo Fisher Process 11 Parallel Twin Extruder with a screw diameter=11 mm and total processing length of about 44 cm (40 L/D) in which the first 14.1 cm (13 L/D) consisted of 1/1 pitch conveying elements, the next about 6.6 cm (6 L/D) consisted of mixing elements, and the final 23.2 cm (21 L/D) consisted of 1/1 pitch conveying elements. The zone temperatures were set to: zone 2:80° C., zone 3:80° C., zone 4, 80° C., zone 5:15° C., zone 6:15° C., zone 7:15° C., zone 8:15° C., and the final 27.5 cm (25 L/D) of the barrel was cooled by draping with plastic bags filled with ice. With the screws turning at about 100 rpm, a total of about 200 grams of mill base was processed in about 10 minutes where upon the zone temperatures increased to: zone 1 (inlet): not recorded, zone 2:80° C., zone 3:80° C., zone 4, 80° C., zone 5:62° C., zone 6:49° C., zone 7:40° C., zone 8:30° C., and the die temperature was about 22° C.

The concentrated lipid dispersion had the appearance of an opaque liquid with viscosity approximately that of vegetable oil. When diluted with deionized water analyzed by dynamic light scattering, the sample was observed to have volume average particle diameter about 297 nm and number average particle diameter about 179 nm.

This example demonstrates that processing a mill base composition which exhibits macroscopic birefringence between about 60° C. and about 95° C. with a twin-screw extruder in which maximum $\Delta T=53°$ C. gives a concentrated lipid dispersion with volume average particle diameter greater than about 200 nm.

Example 2

Preparation of a Concentrated Non-Nanoparticle Lipid Dispersion Including Sorbitan Oleate, Laureth-23, PEG-100 Stearate, Dioleyl Phosphatidyl Choline, Isopropyl Myristate, d-Limonene, Ibuprofen and Medium Chain Triglyceride Oil A mill base was prepared as described in Example 1. The Thermo Fisher Process 11 Parallel Twin Extruder was modified by building a reservoir around the final 22 cm (20 L/D of the barrel) and the reservoir was filled with a mixture of ice and water. The microemulsion composition was heated to about 83° C. and kept hot by intermittent heating using a hand held propane gas torch and was fed into a Thermo Fisher Process 11 Parallel Twin Extruder with a screw diameter=11 mm and total processing length of about 44 cm (40 L/D) in which the first 14.1 cm (13 L/D) consisted of 1/1 pitch conveying elements, the next about 6.6 cm (6 LID) consisted of mixing elements, and the final 23.2 cm (21 L/D) consisted of 1/1 pitch conveying elements. Before introducing the warm microemulsion to the extruder the zone temperatures were: zone 2:80° C., zone 3:80° C., zone 4, 80° C., zone 5:38° C., zone 6:16° C., zone 7:15° C., zone 8:15° C. and the die temperature was about 17° C. With the screws turning at about 200 rpm, a total of about 300 grams of mill base was processed in about 5 minutes where upon the zone temperatures increased to: zone 1 (inlet): not recorded, zone 2:80° C., zone 3:80° C., zone 4, 80° C., zone 5:60° C., zone 6:48° C., zone 7:39° C., zone 8:30° C., and the die temperature was about 20° C.

The concentrated lipid dispersion had the appearance of an opaque liquid with viscosity approximately that of vegetable oil. When diluted with deionized water analyzed by dynamic light scattering, the sample was observed to have volume average particle diameter about 507 nm and number average particle diameter about 328 nm.

This example demonstrates that processing a mill base composition which exhibits macroscopic birefringence between about 60° C. and about 95° C. with a twin-screw extruder in which maximum $\Delta T=50°$ C. gives a concentrated lipid dispersion with volume average particle diameter greater than about 200 nm.

Example 3

Preparation of a Concentrated Lipid Nanoparticle Dispersion Including Sorbitan Oleate, Laureth-23, PEG-100 Stearate, Dioleyl Phosphatidyl Choline, Isopropyl Myristate, d-Limonene, Ibuprofen and Medium Chain Triglyceride Oil A mill base was prepared as described in Example 1. The Thermo Fisher Process 11 Parallel Twin Extruder was modified by building a reservoir around the final 22 cm (20 L/D of the barrel) and the reservoir was filled with a mixture of ice and water.

The microemulsion composition was heated to about 83° C. and kept hot by intermittent heating using a hand-held propane gas torch and was fed into a Thermo Fisher Process 11 Parallel Twin Extruder with a total of about 40 LID in which the first about 13 LID consisted of 1/1 conveying elements, the next about 6 L/D consisted of mixing elements, and the final 21 L/D consisted of 1/1 pitch conveying elements. Before introducing the hot microemulsion to the extruder the zone temperatures were: zone 2:80° C., zone 3:80° C., zone 4, 80° C., zone 5:35° C., zone 6:15° C., zone 7:15° C., zone 8:15° C. With the screws turning at about 200 rpm, a total of about 150 grams of mill base was processed in about 3 minutes where upon the zone temperatures increased to: zone 1 (inlet): not recorded, zone 2:80° C., zone 3:80° C., zone 4, 80° C., zone 5:54° C., zone 6:34° C., zone 7:25° C., zone 8:18° C., and the die temperature was about 18° C. The concentrated lipid nanoparticle dispersion had the appearance of a somewhat translucent liquid with viscosity approximately that of vegetable oil. When diluted with deionized water analyzed by dynamic light scattering, the sample was observed to have volume average particle diameter about 139 nm and number average particle diameter about 92 nm.

This example demonstrates that processing a mill base composition which exhibits macroscopic birefringence between about 60° C. and about 95° C. with a twin-screw extruder in which the maximum $\Delta T=85°$ C. gives a concentrated lipid nanoparticle dispersion with volume average particle diameter less than about 150 nm.

Example 4

Preparation of a Concentrated Lipid Nanoparticle Dispersion Including Sorbitan Oleate, Laureth-23, PEG-100 Stearate, Dioleyl Phosphatidyl Choline, Isopropyl Myristate, d-Limonene, Ibuprofen and Medium Chain Triglyceride Oil A mill base was prepared as described in Example 1. The Thermo Fisher Process 11 Parallel Twin Extruder was modified by building a reservoir around the final about 22 cm (20 L/D of the barrel) and the reservoir was filled with a mixture of ice and water.

The mill base composition was heated to about 40° C. at which point it was opaque and viscous. It was kept warm by intermittent heating using a hand-held propane gas torch and was fed into a Thermo Fisher Process 11 Parallel Twin Extruder with a total of about 40 L/D in which the first 13 L/D consisted of 1/1 pitch conveying elements, the next about 6 L/D consisted of mixing elements, and the final 21 L/D consisted of 1/1 pitch conveying elements. Before introducing the warm microemulsion to the extruder the zone temperatures were: zone 2:95° C., zone 3:95° C., zone 4, 95° C., zone 5:80° C., zone 6:45° C., zone 7:30° C., zone 8:22° C. and the die temperature was about 24° C. With the screws turning at about 200 rpm, a total of about 470 grams of mill base was processed in about 6 minutes where upon the zone temperatures increased to: zone 1 (inlet): not recorded, zone 2:95° C., zone 3:95° C., zone 4, 95° C., zone 5:80° C., zone 6:58° C., zone 7:45° C., zone 8:33° C., and the die temperature was about 24° C. The concentrated lipid nanoparticle dispersion had the appearance of a translucent beige liquid with viscosity approximately that of honey. When examined by cryogenic electron microscopy using the method described by Lee, et al. (Lee H, Morrison E., Frethem C., Zasadzinski J., McCormick A., Cryogenic Electron Microscopy Study of Nanoemulsion Formation from Microemulsion. *Langmuir,* 2014, 30 (38), 10826-10833), the concentrated lipid nanoparticle dispersion was seen to be a concentrated dispersion of particles less than about 100 nm diameter. When diluted with deionized water analyzed by dynamic light scattering, the sample was observed to have volume average particle diameter about 75.3 nm and number average particle diameter about 38.1 nm. A 20 mL sample of the nanoparticle dispersion was placed in a 30 mL beaker with a magnetic stirrer and gently heated to about 50° C. using a microwave oven on defrost mode. The warm sample was stirred on a magnetic stirrer/hotplate between about 100 rpm and about 400 rpm while heating at a rate of about 4° C. per minute. The sample was observed to be birefringent when observed between cross polarized films between about 79° C. and about 80° C., Indicating the dispersed nanoparticles have latent lamellar structure.

This example demonstrates that processing a mill base composition which exhibits macroscopic birefringence between about 60° C. and about 95° C. with a twin-screw extruder in which the maximum ΔT=82° C. gives a concentrated lipid nanoparticle dispersion with volume average particle diameter less than about 100 nm and latent lamellar structure.

A second sample of ibuprofen nanoparticle dispersion was prepared as described above having volume average particle diameter about 88.3 nm and number average particle diameter about 68.1 nm. Dermal permeation of ibuprofen in the concentrated nanoparticle dispersion was evaluated in a side-by-side test with Proff Schmerz Crème (Dolorgeit, Sankt Augustin Germany, containing about 5.0 weight percent (wt. %) ibuprofen) using test method essentially as described by Abdel-Mottaleb et al. (Abdel-Mottaleb M, Neumann D, Lamprecht A., Lipid nanocapsules for dermal application: a comparative study of lipid-based versus polymer-based nanocarriers. *Eur J. Pharm Biopharm.* 2011 September; 79(1):36-42. doi:10.1016/j.ejpb.2011.04.009) using 0.64 $cm^2$ Franz-type diffusion cells with pH about 7.4 phosphate buffer in the receiver compartment at about 37° C. Porcine skin samples were prepared from freshly harvested ears obtained from a local meat processing shop. Hair was carefully clipped to about 2 mm length, subdermal tissue was removed by hand using a scalpel and samples were cut into about 1.5 cm squares. Skin samples were placed in Franz cells and allowed to equilibrate to about 37° C. for about 60 minutes before about 2 mL of the nanoparticle dispersion or Proff Schmerz Crème was added to the Franz cell donor compartment. Samples of receiver fluid (300 microliters) were removed about 2, 4, 6 and 8 hours after introduction of lotion sample and about 300 microliters of fresh buffer added to keep receiver fluid level constant. The concentration of permeated ibuprofen was determined using a C18 reverse phase column using a Beckman-Coulter 125 Solvent Module HPLC System and 166 UV-Vis Detector operating at about 215 nm. FIG. 1 shows permeation of Ibuprofen from the nanoparticle dispersion is about 2.5 times that of Proff Schmerz Crème.

What this Example shows is that a concentrated nanoparticle dispersion with polydispersity in surfactant hydrophile-lipophile-balance (HLB) values with a weight mean square hydrophile-lipophile-balance (HLB) deviation equal to 1.78 and having latent lamellar structure provides more than twice the dermal permeation of ibuprofen than a conventional ibuprofen lotion dispersion with an equivalent concentration of ibuprofen.

Example 5

Preparation of a Concentrated Lipid Nanoparticle Dispersion Including Processing a Mill Base Including Oils, Water, Ibuprofen and an Ether Type Polyethoxylated High Hydrophile-Lipophile-Balance (HLB) Surfactant A mill base was prepared which contained about 11.4 weight percent (wt. %) ceteareth-20, about 5.7 weight percent (wt. %) ibuprofen, about 4.9 weight percent (wt. %) sorbitan oleate, about 13.8 weight percent (wt. %) isopropyl myristate, about 13.8 weight percent (wt. %) capric/caprylic triglyceride oil, about 4.1 weight percent (wt. %) limonene, and about 46.3 weight percent (wt. %) of a about 0.09 weight percent (wt. %) solution of sodium chloride in deionized water. The mill base was prepared by warming all ingredients except the sodium chloride solution to about 60° C. to give a clear solution, and then adding the sodium chloride solution to the warm, stirring lipophilic phase, giving an opaque dispersion. The mill base was heated and held at a temperature just below the boiling point and fed while hot into a modified Process 11 twin screw extruder with an ice water reservoir at a rate sufficient to maintain the screws under the inlet port in a submerged state. The zone temperatures were set to about 95° C. in zones 2, 3, and 4; to about 50° C. in zone 5, and to about 10° C. in zones 7, 8, and 9. The screw rotation rate was about 200 rpm. About 400 grams of extruded processed mill base was collected as a transparent colorless dispersion. The volume average particle diameter was about 54.6 nm and number average particle diameter was about 43.4 nm when measured by DLS (Dynamic Light Scattering).

This example demonstrates that processing a mill base including oils, water, surfactants and ibuprofen including an ether type polyethoxylated high hydrophile-lipophile-balance (HLB) surfactant gives an aqueous dispersion of about 54 weight percent (wt. %) lipophilic ibuprofen containing nanoparticles.

Examples 6-13

Preparation of Concentrated Lipid Nanoparticle Dispersions Including Oils, Water, Ibuprofen and an Ether Type Polyethoxylated High Hydrophile-Lipophile-Balance (HLB) Surfactant and Preparation of Lipid Non-Nanoparticle Dispersions Including Oils, Water, Ibuprofen and an Ester Type Polyethoxylated High Hydrophile-Lipophile-Balance (HLB) Surfactant Mill bases were prepared as described above except ceteareth-20 was replaced by other polyethoxylated high hydrophile-lipophile-balance (HLB) surfactants. Each mill base was processed as described as for Example 5 and the resulting volume average particle diameters of the extruded dispersions were measured by DLS (Dynamic Light Scattering). The composition of the mi bases and the resulting particle sizes are shown in Table E1.

Examples 5-13 demonstrate that processing a mill base including oils, water, surfactants and ibuprofen using a modified twin screw extruder gives nanoparticle dispersions if the mill base includes a high hydrophile-lipophile-balance (HLB) polyethoxylated surfactant which is an ether type polyethoxylated high hydrophile-lipophile-balance (HLB) surfactant or a blend of about 50 weight percent (wt. %) or greater of ether type polyethoxylated high hydrophile-lipophile-balance (HLB) surfactant with about 50 weight percent (wt. %) or less of an ester type polyethoxylated high hydrophile-lipophile-balance (HLB) surfactant. Processing a mill base including oils, water, surfactants and ibuprofen using a modified twin screw extruder does not give a nanoparticle dispersion if the mill base includes an ester type polyethoxylated high hydrophile-lipophile-balance (HLB) surfactant or a blend of about 50 weight percent (wt. %) or greater of ester type polyethoxylated high hydrophile-lipophile-balance (HLB) surfactant with less than about 50 weight percent (wt. %) ether type polyethoxylated high hydrophile-lipophile-balance (HLB) surfactant.

When a sample of the dispersion of Example 11 was heated from about 40° C. to about 85° C., the conductivity was constant at about 530 uS/cm until about 50° C., then decreased monotonically to about 0.23 uS/cm at about 85° C. At no temperature between about 40° C. and about 85° C. was the dispersion transparent or birefringent. This example demonstrates that a dispersion sample including polysorbate-80, sorbitan oleate, isopropyl myristate, medium chain triglyceride oil and ibuprofen with $WMSD_{HLB}$ equal to about 1.49 does not possess latent lamellar structure.

TABLE E1

|  | Ex. 5 | Ex. 6 | Ex. 7 | Ex. 8 | Ex. 9 | Ex. 10 | Ex. 11 | Ex. 10 | Ex. 12 |
| --- | --- | --- | --- | --- | --- | --- | --- | --- | --- |
| ceteareth-20 | 11.4 |  |  |  | 7.1 |  |  |  |  |
| ceteareth-30 |  | 11.9 |  |  |  |  |  |  |  |
| steareth-40 |  |  | 11 7 | 2.9 |  |  |  |  |  |
| steareth-20 |  |  |  | 2.9 |  |  |  |  |  |
| steareth-100 |  |  |  |  |  |  |  |  | 5.0 |
| PEG20 stearate |  |  |  |  |  |  |  |  | 6.6 |
| PEG32 stearate |  |  |  |  |  | 11.4 |  |  |  |
| PEG100 stearate |  |  |  |  | 3.9 |  |  |  |  |
| polysorbate 80 |  |  |  | 5.7 |  |  | 11.4 |  |  |
| PEG30 glyceryl cocoate |  |  |  |  |  |  |  | 11.4 |  |
| sorbitan oleate | 4.9 | 4.9 | 4.9 | 4.8 | 4.9 | 4.9 | 4.9 | 4.9 | 4.9 |
| isopropyl myristate | 13.8 | 13.8 | 13.8 | 13.8 | 13.9 | 13.8 | 13.8 | 13.8 | 13.8 |
| MCT oil | 13.8 | 13.8 | 13.8 | 13.8 | 13.9 | 13.8 | 13.8 | 13.8 | 13.8 |
| d-limonene | 4.1 | 4.1 | 4.0 | 4.1 | 4.1 | 4.1 | 4.1 | 4.1 | 4.0 |
| ibuprofen | 5.7 | 5.7 | 5.7 | 5.7 | 5.7 | 5.7 | 5.7 | 5.7 | 5.7 |
| Dilute NaCl/water | 46.3 | 45.9 | 46.2 | 46.5 | 46.5 | 46.4 | 46.4 | 46.4 | 46.3 |
| Ratio of ether type high hydrophile-lipophile-balance (HLB) surfactant to ester type high hydrophile-lipophile-balance (HLB) surfactant | 100:0 | 100:0 | 100:0 | 50:50 | 65:35 | 0:100 | 0:100 | 0:100 | 43:57 |
| HLB weight-mean-square-deviation, $WMSD_{HLB}$ | 1.75 | 2.01 | 2.83 | 2.21 | 2.11 | 2.12 | 1.49 |  | 2.11 |
| volume average diameter | 54.6 | 123.2 | 96.8 | 133 | 117.6 | 1153 | 468 | 1241 | 276.1 |

Example 14

Preparation of a Concentrated Lipid Nanoparticle Dispersion Including Oils, Water, Lidocaine and a Mixture of Ether Type Polyethoxylated High Hydrophile-Lipophile-Balance (HLB) Surfactant Plus Alkyl Glycoside Hydrophilic Surfactant A mill base was prepared which contained about 5.4 weight percent (wt. %) ceteareth-30, about 5.4 weight percent (wt. %) GIO-103 xylityl caprate/caprylate (Giorbis Laboratories, Glendale, Calif.), about 5.4 weight percent (wt. %) sorbitan oleate, about 3.2 weight percent (wt. %) Alcolec XTRA-A soy lecithin, about 8.7 weight percent (wt. %) isopropyl myristate, about 8.6 weight percent (wt. %) medium chain triglyceride oil, about 8.6 weight percent (wt. %) light mineral oil, about 1.1 weigh percent lidocaine and about 53.7 weight percent (wt. %) water. The weight ratio of hydrophobic nonionic surfactant to polyethoxylated high hydrophile-lipophile-balance (HLB) surfactant was about 1.6 to about 1. The mill base was prepared by warming all ingredients except water to about 60° C. to give a clear solution, and then adding water to the warm, stirring lipophilic phase, giving an opaque dispersion. The mill base was heated and held at a temperature just below the boiling point and fed into a modified Process 11 twin screw extruder with an ice water filed cooling reservoir at a rate sufficient to maintain the screws under the inlet port in a submerged state. The zone temperatures were set to about 95° C. in zones 2, 3, and 4; to about 50° C. in zone 5, and to about 10° C. in zones 7, 8, and 9. The screw rotation rate was about 200 rpm. About 400 grams of extruded processed mill base was collected as a translucent colorless dispersion. The volume average particle diameter of the processed dispersion was about 54.6 nm when measured by DLS (Dynamic Light Scattering).

This example demonstrates that processing a mill base including oils, water, surfactants and ibuprofen including a mixture of an ether type polyethoxylated high hydrophile-lipophile-balance (HLB) surfactant plus a glycoside hydrophilic surfactant wherein the weight ratio of ether type polyethoxylated high hydrophile-lipophile-balance (HLB) surfactant to glycoside hydrophilic surfactant is about 50:50 gives an aqueous dispersion of about 54 weight percent (wt. %) lipophilic ibuprofen containing nanoparticles.

Example 15

Preparation of a Concentrated Lipid Nanoparticle Dispersion Including Oils, Water, Ibuprofen and a Mixture of Ether Type Polyethoxylated High Hydrophile-Lipophile-Balance (HLB) Surfactant Plus Alkyl Glycoside Hydrophilic Surfactant A mill base was prepared which contained about 3.0 weight percent (wt. %) ceteareth-20, about 5.8 weight percent (wt. %) of about a 62 percent aqueous solution of cocoglucoside in water (Chemistry Connection, Conway, Ariz.), about 5.0 weight percent (wt. %) sorbitan oleate, about 2.5 weight percent (wt. %) Alcolec XTRA-A soy lecithin, about 8.7 weight percent (wt. %) Isopropyl myristate, about 9.3 weight percent (wt. %) medium chain triglyceride oil, about 6.2 weight percent (wt. %) Siclone SR-5, about 1.9 weight percent (wt. %) ibuprofen, about 0.6 weight percent (wt. %) BHT, about 0.6 weight percent (wt. %) tetrasodium EDTA, about 0.2 weight percent (wt. %) citric acid and about 56.2 weight percent (wt. %) water. The weight ratio of hydrophobic nonionic surfactant to polyethoxylated high hydrophile-lipophile-balance (HLB) surfactant was about 2.5 to about 1. The mill base was prepared by warming all ingredients except water to about 60° C. to give a clear solution, and then adding water to the warm, stirring lipophilic phase, giving an opaque mill base dispersion. The mill base was processed as described as for Example 14 to give a translucent product with volume average particle diameter about 63.3 nm when measured by DLS (Dynamic Light Scattering).

This example demonstrates that processing a mill base including oils, water, surfactants and ibuprofen including a mixture of an ether type polyethoxylated high hydrophile-lipophile-balance (HLB) surfactant plus a glycoside hydrophilic surfactant wherein the weight ratio of ether type polyethoxylated high hydrophile-lipophile-balance (HLB) surfactant to glycoside hydrophilic surfactant is about 45:55 gives an aqueous dispersion of about 46 weight percent (wt. %) lipophilic ibuprofen containing nanoparticles.

Example 16

Preparation of a Concentrated Lipid Nanoparticle Dispersion Including Oils, Water, Lidocaine and a Mixture of Ether Type Polyethoxylated High Hydrophile-Lipophile-Balance (HLB) Surfactant Plus Alkyl Glycoside Hydrophilic Surfactant A mill base was prepared which contained about 1.6 weight percent (wt. %) ceteareth-20, about 4.8 weight percent (wt. %) of about a 62 percent aqueous solution of cocoglucoside in water (Chemistry Connection, Conway, Ariz.), about 1.0 weight percent (wt. %) of about 50 percent aqueous solution of decyl glucoside (Chemistry Connection, Conway, Ariz.), about 5.1 weight percent (wt. %) sorbitan oleate, about 2.6 weight percent (wt. %) Alcolec XTRA-A soy lecithin, about 9.5 weight percent (wt. %) isopropyl myristate, about 8.9 weight percent (wt. %) medium chain triglyceride oil, about 6.4 weight percent (wt. %) Siclone SR-5, about 0.7 weight percent (wt. %) ibuprofen, about 0.6 weight percent (wt. %) BHT, about 0.5 weight percent (wt. %) tetrasodium EDTA, about 0.2 weight percent (wt. %) citric acid and about 58.1 weight percent (wt. %) water. The weight ratio of hydrophobic nonionic surfactant to polyethoxylated high hydrophile-lipophile-balance (HLB) surfactant was about 4.8 to about 1. The mill base was prepared by warming al ingredients except water to about 60° C. to give a clear solution, and then adding water to the warm, stirring lipophilic phase, giving an opaque mill base dispersion. The mill base was processed as described as for Example 14 to give a translucent product with volume average particle diameter about 70.2 nm when measured by DLS (Dynamic Light Scattering).

Figure 2:
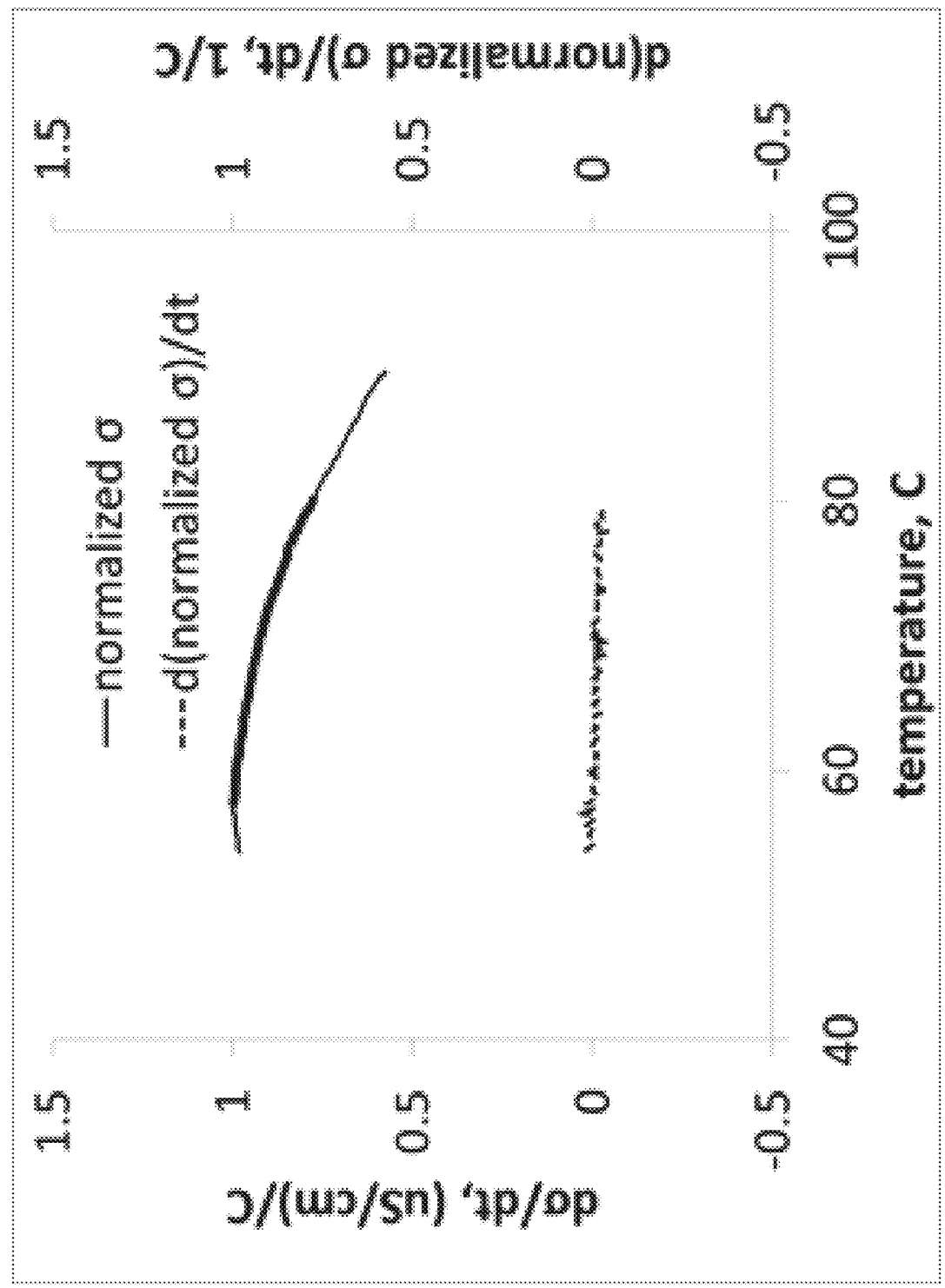
FIG. 2 is a plot of normalized conductivity vs temperature and first derivative of conductivity vs temperature for the nanoparticle dispersion of Example 55.

A sample of the nanoparticle dispersion product was tested for latent lamellar structure by heating and observing for optical birefringence and negative peaks in the plot of electrical conductivity vs temperature. Nanoparticle dispersion product (26.3 g) in a 30 mL Pyrex beaker heated and stirred on a hotplate at between about 100 rpm and about 400 rpm set to heat at a rate of about 2° C. per minute and the conductivity was measured about every 5 seconds using a Thermo Scientific Orion 3-star Conductivity Meter Model 1114000 with a 013005MD 4-cell conductivity cell electrode. Normalized conductivity was calculated as the ratio of conductivity to the maximum conductivity measured in the temperature range of about 55° C. to about 90° C. and the first derivative of normalized conductivity vs temperature was calculated for each conductivity and temperature pair between about 55° C. and about 90° C. Plots of normalized conductivity and the first derivative of normalized conductivity are shown in FIG. 2. The plot of normalized conductivity vs temperature did not show a negative peak and the first derivative plot did not show a value greater than about 0.05 C$^{-1}$. During the heating experiment, the nanoparticle dispersion composition became transparent and was observed to be birefringent between about 61° C. and about 75° C. when observed between two crossed pieces of polarizing film. The observation of optical birefringence in the heated nanoparticle dispersion indicates that nanoparticles in the dispersion have a latent lamellar structure. This example demonstrates that processing a mill base including oils, water, surfactants and lidocaine including a mixture of an ether type polyethoxylated high hydrophile-lipophile-balance (HLB) surfactant plus a glycoside hydrophilic surfactant wherein the weight ratio of ether type polyethoxylated high hydrophile-lipophile-balance (HLB) surfactant to glycoside hydrophilic surfactant is about 31:69 gives an aqueous dispersion of about 42 weight percent (wt. %) lipophilic ibuprofen containing nanoparticles with latent lamellar structure.

Examples 14-16 demonstrate that processing a mill base including oils, water, surfactants and ibuprofen or lidocaine using a modified twin screw extruder gives nanoparticle dispersions if the mill base includes an ether type polyethoxylated hydrophilic surfactant and a glycoside type non-polyethoxylated hydrophilic; surfactant where the weight ratio of ether type polyethoxylated high hydrophile-lipophile-balance (HLB) surfactant to glycoside type non-polyethoxylated hydrophilic surfactant is 50:50, 45:55, or 31:69. Compositions of Examples 14-16 and resulting volume average particle diameters are shown in Table E2.

TABLE E2

|  | Example 14 | Example 15 | Example 16 |
|---|---|---|---|
| ceteareth-20 |  | 3.0 | 1.6 |
| ceteareth-30 | 5.4 |  |  |
| GIO-103 xylityl caprylate | 5.4 |  |  |
| coco glucoside Chemistry Connection |  | 5.8 | 4.8 |
| decyl glucoside Chemistry Connection |  |  | 1.0 |
| sorbitan oleate | 5.4 | 5.0 | 5.1 |
| XTRA-A lecithin | 3.2 | 2.5 | 2.6 |
| MCT oil | 8.6 | 9.3 | 9.5 |
| isopropyl myristate | 8.7 | 8.7 | 8.9 |
| light mineral oil | 8.6 |  |  |
| Siclone SR-5 |  | 6.2 | 6.4 |
| Lidocaine | 1.1 |  | 0.7 |
| Ibuprofen |  | 1.9 |  |
| BHT |  | 0.6 | 0.6 |
| tetrasodillm EDTA |  | 0.6 | 0.5 |
| citric acid |  | 0.2 | 0.2 |
| water | 53.7 | 56.2 | 58.1 |
| Ratio of ether type high hydrophile-lipophile-balance (HLB) surfactant to glycoside type high hydrophile-lipophile-balance (HLB) surfactant | 50:50 | 45:55 | 31:69 |
| Ratio of hydrophobic nonionic surfactants to polyethoxylated high hydrophile-lipophile-balance (HLB) surfactant | 1.6:1 | 2.5:1 | 4.8:1 |
| HLB weight-mean-square-deviation; WMSD$_{HLB}$ | 3.27 | 2.97 | 3.38 |
| volume average diameter | 55.6 | 63.3 | 70.2 |

Example 17

Preparation of a Concentrated Lipid Nanoparticle Dispersion Including Oils, Water, Lidocaine and an Ether Type Polyethoxylated High Hydrophile-Lipophile-Balance (HLB) Surfactant A mill base was prepared which contained about 8.9 weight percent (wt. %) ceteareth-20, about 2.3 weight percent (wt. %) lidocaine, about 9.0 weight percent (wt. %) sorbitan stearate, about 9.0 weight percent (wt. %) isopropyl myristate, about 7.7 weight percent (wt. %) capric/caprylic triglyceride oil, about 8.3 weight percent (wt. %) light mineral oil, about 0.02 weight percent (wt. %) sodium chloride, and about 54.7 weight percent (wt. %) water. The mil base was prepared by warming all ingredients except sodium chloride and water to about 60° C. to give a clear solution, and then adding a sodium chloride solution in water to the warm, stirring lipophilic phase, giving a mill base as an opaque dispersion. The mill base was heated and held at a temperature just below the boiling point and fed while hot into a modified Process 11 twin screw extruder at a rate sufficient to maintain the screws under the inlet port in a submerged state. The zone temperatures were set to about 95° C. in zones 2, 3, and 4; to about 50° C. in zone 5, and to about 10° C. in zones 7, 8, and 9. The screw rotation rate was about 200 rpm. About 400 grams of extruded processed mill base was collected as a transparent colorless dispersion. The particle size of the processed dispersion was measured using dynamic light scattering and found to have volume average particle size about 29.7 nm and number average particle size about 26.5 nm.

This example demonstrates that processing a mill base including oils, water, surfactants and lidocaine where the polyethoxylated high hydrophile-lipophile-balance (HLB) surfactant is an ether type polyethoxylated high hydrophile-lipophile-balance (HLB) surfactant gives nanoparticle dispersion.

Example 18

Preparation of a Concentrated Lipid Non-Nanoparticle Dispersion Including Oils, Water, Lidocaine and an Ester Type Polyethoxylated High Hydrophile-Lipophile-Balance (HLB) Surfactant The procedure of Example 17 was repeated except the ceteareth-20 was replaced with an equal amount of PEG 20 stearate. About 400 grams of extruded processed mill base was collected as an opaque colorless dispersion. The particle size of the processed dispersion was measured using dynamic light scattering and found to have volume average particle size about 1873 nm and number average particle size about 136.7 nm.

Examples 17 and 18 demonstrate that processing a mill base including oils, water, surfactants and lidocaine using a modified twin screw extruder gives a nanoparticle dispersion if the mill base includes an ether type polyethoxylated high hydrophile-lipophile-balance (HLB) surfactant but does not give nanoparticle dispersions if the mill base includes an ester type polyethoxylated high hydrophile-lipophile-balance (HLB) surfactant.

Example 19

Preparation of a Concentrated Lipid Nanoparticle Dispersion Including Ois, Water, Ibuprofen, and an Ester Type Polyethoxylated High Hydrophile-Lipophile-Balance (HLB) Surfactant Plus Lecithin A mill base was prepared which contained about 10.9 weight percent (wt. %) PEG32 stearate (Jeemate 1540-DPS Flake, Jeen International Corporation, Fairfield, N.J.), about 5.5 weight percent (wt. %) ibuprofen, about 4.8 weight percent (wt. %) sorbitan oleate, about 3.5 weight percent (wt. %) Alcolec XTRA-A lecithin (soybean lecithin with minimum 66% acetone insolubles, American Lecithin Oxford, Conn.), about 13.3 weight percent (wt. %) isopropyl myristate, about 13.3 weight medium chain triglyceride oi, about 4.1 weight percent (wt. %) limonene, and about 44.6 weight percent (wt. %) of a about 0.09 weight percent (wt. %) solution of sodium chloride in deionized water. The weight mean square deviation of the surfactants, $WMSD_{HLB}$, was 3.90. This is the same composition as Example 10 except that it includes lecithin, a phospholipid. The mill base was prepared by warming al ingredients except the sodium chloride solution to about 60° C. to give a clear solution, and then adding the sodium chloride solution to the warm, stirring lipophilic phase, giving a mill base as an opaque dispersion. The mill base was heated and held at a temperature just below the boiling point and fed while hot into a Process 11 twin screw extruder modified with a reservoir of ice water at a rate sufficient to maintain the screws under the inlet port in a submerged state. The zone temperatures were set to about 95° C. in zones 2, 3, and 4; to about 50° C. in zone 5, and to about 10° C. in zones 7, 8, and 9. The screw rotation rate was about 200 rpm. About 400 grams of extruded processed mill base was collected as a translucent light yellow dispersion. The particle size of the processed dispersion was measured using dynamic light scattering and found to have volume average particle size about 97.5 nm compared to about 1153 nm for the composition of Example 10 with no phospholipid.

A sample of the nanoparticle dispersion product was tested for latent lamellar structure by heating and observing for optical birefringence and negative peaks in the plot of electrical conductivity vs temperature. Nanoparticle dispersion product (28.1 g) in a 30 mL Pyrex beaker was warmed gently in a microwave oven on defrost cycle to about 55° C., making it sufficiently fluid so as to be stirred using a magnetic stirrer/hotplate with a stirring rate of between about 100 and about 400 rpm. The hotplate was set to heat the stirring sample at a rate of about 4° C. per minute and the conductivity was measured about every 5 seconds using a Thermo Scientific Orion 3-star Conductivity Meter Model 1114000 with a 013005MD 4-cell conductivity cell electrode. Normalized conductivity was calculated as the ratio of conductivity to the maximum conductivity measured in the temperature range of about 55° C. to about 87° C. and the first derivative of normalized conductivity vs temperature was calculated for each conductivity and temperature pair between about 55° C. and about 87° C. Plots of normalized conductivity and the first derivative of normalized conductivity are shown in FIG. 3. The plot of normalized conductivity vs temperature shows a negative peak at about 71° C. and the first derivative plot shows a peak with amplitude about 1.0 $C^{-1}$ at about 71° C. The presence of a negative peak in the plot of conductivity vs temperature and the amplitude of the first derivative plot with greater than about 0.15 $C^{-1}$ indicate nanoparticles in the dispersion product have a latent lamellar structure. During the heating experiment, the nanoparticle dispersion composition became transparent and was observed to be birefringent between about 72° C. and about 75° C. when observed between two crossed pieces of polarizing film. The observation of optical birefringence in the heated nanoparticle dispersion indicates that nanoparticles in the dispersion have a latent lamellar structure.

This example demonstrates that processing a mill base including oils, water, surfactants and ibuprofen with an ester type polyethoxylated high hydrophile-lipophile-balance (HLB) surfactant gives a non-nanoparticle dispersion and processing including oils, water, surfactants and ibuprofen with an ester type polyethoxylated high hydrophile-lipophile-balance (HLB) surfactant plus lecithin, a phospholipid gives a dispersion of nanoparticles with latent lamellar structure.

Examples 20-22

Preparation of Concentrated Lipid Nanoparticle Dispersions Including Oils, Water, Ibuprofen, an Ester Type Polyethoxylated High Hydrophile-Lipophile-Balance (HLB) Surfactant and a Phospholipid Mill bases were prepared as described above except Alcolec XTRA-A lecithin was replaced by Phospholipon 90G (unsaturated diacyl-phosphatidylcholine with about 94 to about 100% soy phosphatidyl choline, Lipoid USA, Newark, N.J.), Phospholipon 90H (hydrogenated phosphatidyl choline with approximately about 85% stearate and about 15% palmitate, Lipoid USA, Newark, N.J.) or Sunlipon 65 (phospholipids containing at least about 60% phosphatidylcholine from sunflower lecithin, Perimondo, New York, N.Y.). Each mill base was processed as described as for Example 19 and the resulting volume average particle diameters of the extruded dispersions were measured by dynamic light scattering. The composition of the mil bases and the resulting particle sizes are shown in Table E3.

Example 23

Preparation of a Concentrated Lipid Nanoparticle Dispersion Including Ois, Water, Ibuprofen, and an Ester Type Polyethoxylated High Hydrophile-Lipophile-Balance (HLB) Surfactant Plus Lecithin Example 19 was repeated except that PEG32 stearate was replaced with polysorbate 80. This is the same composition as Example 11 except that it contains Alcolec XTRA-A lecithin, a phospholipid. When processed as described for Example 19, the product was a translucent light yellow dispersion with volume average particle size about 111.9 nm compared to about 468 nm for Example 11. The composition of the mill base is shown in Table E3.

Examples 19-23 demonstrate that processing a mill base including oils, water, surfactants and Ibuprofen using a modified twin screw extruder gives nanoparticle dispersions if the mill base includes an ester type polyethoxylated high hydrophile-lipophile-balance (HLB) surfactant plus a phospholipid compound. Processing a mill base including oils, water, surfactants and ibuprofen using a modified twin screw extruder does not give nanoparticle dispersions if the mill base includes an ester type polyethoxylated high hydrophile-lipophile-balance (HLB) surfactant without a phospholipid compound.

When a sample of the dispersion was heated from about 40° C. to about 80° C., conductivity was constant at about 930 uS/cm until about 50° C., then decreased monotonically to about 1.0 uS/cm at about 80° C. The sample was transparent and birefringent between about 60° C. and about 64° C., Indicating the presence of a lamellar structure. This example demonstrates that a dispersion sample including polysorbate-80, sorbitan oleate, isopropyl myristate, medium chain triglyceride oil and ibuprofen plus lecithin, a phospholipid and having WMSD$_{HLB}$ equal to 2.06 possesses latent lamellar structure.

TABLE E3

| | Example 19 | Example 20 | Example 21 | Example 22 | Example 23 |
|---|---|---|---|---|---|
| PEG32 stearate | 10.9 | 10.9 | 11.3 | 11.2 | |
| polysorbate 80 | | | | | 11.2 |
| sorbitan oleate | 4.8 | 4.7 | 4.8 | 4.8 | 4.8 |
| Alecolec XTRA-A lecithin | 3.5 | | | | 1.2 |
| Phospholipon P90G | | 4.4 | | | |
| Phospholipon 90H | | | 1.0 | | |
| Sunlipon 65 | | | | 2.0 | |
| isopropyl myristate | 13.3 | 13.2 | 13.7 | 13.5 | 13.7 |
| capric/caprylic triglyceride | 13.3 | 13.2 | 13.7 | 13.6 | 13.8 |
| d-limonene | 4.1 | 3.9 | 4.0 | 4.0 | 4.0 |
| ibuprofen | 5.5 | 5.4 | 5.6 | 5.6 | 5.6 |
| NaCl | 0.04 | 0.03 | 0.04 | 0.04 | 0.03 |
| water | 44.6 | 44.3 | 45.8 | 45.4 | 45.7 |
| total | 100.0 | 100.0 | 100.0 | 100.0 | 100.0 |
| volume average diameter | 97.5 | 139.9 | 136.3 | 100.6 | 111.9 |

Example 24

Preparation of a Concentrated Lipid Nanoparticle Dispersion Including Oils, Water, Lidocaine, and an Ether Type Polyethoxylated High Hydrophile-Lipophile-Balance (HLB) Surfactant A mii base was prepared which contained about 9.8 weight percent (wt. %) ceteareth-20, about 2.5 weight percent (wt. %) lidocaine base, about 9.7 weight percent (wt. %) sorbitan stearate, about 8.9 weight percent (wt. %) isopropyl myristate, about 9.0 weight percent (wt. %) capric/caprylic triglyceride oil, about 9.0 weight percent (wt. %) light mineral oil, about 0.04 weight percent (wt. %) sodium chloride, and about 51.0 weight percent (wt. %) water. The mil base was prepared by warming all ingredients except the sodium chloride solution and water to about 60° C. to give a clear solution, and then adding the sodium chloride/water solution to the warm, stirring lipophilic phase, giving a mi base as an opaque dispersion. The mill base was heated and held at between about 80° C. and about 85° C. and fed while hot into a Process 11 twin screw extruder modified with a reservoir of ice water at a rate sufficient to maintain the screws under the inlet port in a submerged state. The zone temperatures were set to about 95° C. in zones 2, 3, and 4; to about 50° C. in zone 5, and to about 10° C. in zones 7, 8, and 9. The screw rotation rate was about 200 rpm. About 400 grams of extruded processed mill base was collected as a transparent colorless dispersion. The particle size of the processed dispersion was measured using dynamic light scattering and found to have volume average particle size about 28.8 nm.

Examples 25-28

Preparation of Concentrated Lipid Nanoparticle Dispersion Including Oils, Water, an Ether Type Polyethoxylated High Hydrophile-Lipophile-Balance (HLB) Surfactant and Hydrocortisone, Benzocaine, Diclofenac, or Aspirin Mill bases were prepared as described above with the compositions listed in Table E4. Each mill base was processed as described as for Example 24 except that mill bases for Examples 27 and 28 were heated to nearly boiling before feeding into the extruder. The composition of the mill bases and the resulting particle sizes are shown in Table E4. What these Examples show is mill bases including oils, water, an ether type polyethoxylated high hydrophile-lipophile-balance (HLB) surfactant and drugs including lidocaine, hydrocortisone, benzocaine, diclofenac and aspirin can be processed using a modified twin screw extruder to give nanoparticle dispersions.

TABLE E4

| | Example 24 | Example 25 | Example 26 | Example 27 | Example 28 |
|---|---|---|---|---|---|
| ceteareth-20 | 9.8 | | 4.3 | 9.2 | 10.2 |
| ceteareth-30 | | 4.0 | | | |
| steareth-40 | | 4.0 | 4.3 | | |
| sorbitan stearate | 9.7 | 7.5 | | | |
| sorbitan oleate | | | 6.4 | 4.1 | 5.1 |
| Phospholipon 90G | | | 1.1 | 1.7 | |
| Alcolec XTRA-A lecithin | | | | | 3.4 |
| oleyl alcohol | | 7.5 | | | |
| cetyl alcohol | | | | 3.1 | |
| benzyl alcohol | | 3.4 | | | |
| fractionated coconut oil | 9.0 | 7.5 | 2.1 | 20.1 | |
| medium chain triglyceride oil | | | | | 14.4 |
| isopropyl myristate | 8.9 | 7.6 | 21.4 | 12.3 | 13.5 |
| light mineral oil | 9.0 | | 4.3 | | |
| lidocaine base | 2.5 | | | | |
| hydrocortisone | | 0.5 | | | |
| benzocaine | | | 2.1 | | |
| diclofenac sodium | | | | 1.6 | |
| aspirin | | | | | 2.5 |
| NaCl | 0.04 | 0.05 | 0.04 | 0.04 | 0.10 |
| tetrasodilim EDTA | | | | 0.22 | |
| citric acid | | | | 0.34 | |
| BHT | | | | 0.11 | |
| water | 51.0 | 57.9 | 53.9 | 47.1 | 50.7 |
| total | 100.00 | 100.00 | 100.00 | 100.00 | 100.00 |
| HLB weight-mean-square-deviation, WMSD$_{HLB}$ | 2.47 | 3.92 | | | 3.41 |
| volume average diameter, nm | 28.76 | 76.5 | 42 | 52.4 | 90.8 |

Example 29

Preparation of a Concentrated Lipid Nanoparticle Dispersion Including Isopropyl Myristate, Capric/Caprylic Triglyceride Oil, Limonene, Water, Ibuprofen and an Ether Type Polyethoxylated High Hydrophile-Lipophile-Balance (HLB) Surfactant A mill base was prepared which contained about 9.8 weight percent (wt. %) ceteareth-30, about 5.1 weight percent (wt. %) ibuprofen, about 4.4 weight percent (wt. %) sorbitan oleate, about 12.4 weight percent (wt. %) isopropyl myristate, about 12.8 weight percent (wt. %) capric/caprylic triglyceride oil, about 3.6 weight percent (wt. %) limonene, and about 51.9 weight percent (wt. %) water of a about 750 ppm solution of NaCl in water. The mill base was prepared by warming al ingredients except the sodium chloride solution and water to about 60° C. to give a clear solution, and then adding the sodium chloride/water solution to the warm, stirring lipophilic phase, giving a mill base as an opaque dispersion. The mill base was heated and held at about 90° C. and fed while hot into a Process 11 twin screw extruder modified with an ice water flied reservoir at a rate sufficient to maintain the screws under the inlet port in a submerged state. The zone temperatures were set to about 80° C. in zones 2, 3, and 4 and to about 15° C. in zones 5 through 9. The screw rotation rate was about 200 rpm. About 400 grams of extruded processed mill base was collected as a translucent colorless dispersion. The particle size of the processed dispersion was measured using dynamic light scattering and found to have volume average particle size about 51.9 nm

Examples 30-33

Preparation of Concentrated Lipid Nanoparticle Dispersions Including Isopropyl Myristate, Limonene, an oil Selected from sesame Oil or Mineral Oil or Coco-Caprylate/Caprate Oil, Water, Ibuprofen and an Ether Type Polyethoxylated High Hydrophile-Lipophile-Balance (HLB) Surfactant Mill bases were prepared as described for Example 29 with the compositions listed in Table E5. Each mill base was processed as described as for Example 29 except that the mill base for Examples 32 was heated only to about 80° C. before feeding into the extruder. The composition of the mi bases and the resulting particle sizes are shown in Table E5. What these Examples show is that processing mill bases including oils, water, an ether type polyethoxylated high hydrophile-lipophile-balance (HLB) surfactant and oils including isopropyl myristate, capric/caprylic triglyceride oi, limonene, sesame oil, mineral oil, and coco-caprylate/caprate oil with ibuprofen and s-ibuprofen can be processed using a modified twin screw extruder to give concentrated nanoparticle dispersions.

TABLE E5

| | Example 29 | Example 30 | Example 31 | Example 32 | Example 33 |
|---|---|---|---|---|---|
| ceteareth-30 | 10.0 | 10.0 | 10.0 | 10.0 | 10.0 |
| sorbitan oleate | 4.4 | 4.4 | 4.4 | 4.4 | 4.4 |
| isopropyl myristate | 12.4 | 24.9 | 21.2 | 12.4 | 12.4 |
| limonene | 3.6 | 3.7 | 3.7 | 3.7 | 3.7 |
| capric/caprylic triglyercide oil | 12.6 | | | | |
| sesame seed oil | | | 3.7 | | |
| light mineral oil | | | | 12.5 | |
| coco-caprylatelcaprate | | | | | 12.5 |
| ibuprofen | 5.1 | 5.1 | 5.1 | 5.1 | |
| S-ibuprofen | | | | | 5.1 |
| 1000 uS/cm saline | 51.9 | 52.0 | 52.0 | 52.0 | 52.0 |
| total | 100.0 | 100.0 | 100.0 | 100.0 | 100.0 |
| volume average particle size, nm | 70.2 | 73.7 | 55.3 | 33.6 | 53.9 |

Example 34

Preparation of a Concentrated Lipid Nanoparticle Dispersion Including Oils, Water, Ibuprofen, an Ether Type Polyethoxylated High Hydrophile-Lipophile-Balance (HLB) Surfactant, and Methyl Cellulose Water Soluble Polymer A mill base was prepared which contained about 11.3 weight percent (wt. %) ceteareth-20, about 5.7 weight percent (wt. %) Ibuprofen, about 4.9 weight percent (wt. %) sorbitan oleate, about 13.8 weight percent (wt. %) isopropyl myristate, about 13.3 weight percent (wt. %) medium chain triglyceride, oil, about 4.1 weight percent (wt. %) limonene, about 0.03 weight percent (wt. %) NaCl, and about 48.4 weight percent (wt. %) water. The mill base was prepared by warming all ingredients except sodium chloride and water to about 60° C. to give a clear solution, and then adding the sodium chloride as a solution to the warm, stirring lipophilic phase, giving a mill base as an opaque dispersion. The mill base (500 grams) was heated and held at a temperature just below the boiling point and about 0.25 grams of methyl cellulose powder (Methylcellulose HV, Modernist Pantry, Eliot, Me.) added. The viscosity of the hot sample did not increase when methyl cellulose powder was added. Then the composition was fed while hot into a Process 11 twin screw extruder modified with an ice water filled reservoir at a rate sufficient to maintain the screws under the inlet port in a submerged state. The zone temperatures were set to about 95° C. in zones 2, 3, and 4; to 60° C. in zone 5, and to about 10° C. in zones 7, 8, and 9. The screw rotation rate was about 100 rpm. About 400 grams of extruded processed mill base was collected as a hazy transparent colorless gel. The particle size of the processed dispersion was measured using dynamic light scattering and found to have volume average particle size about 53.6 nm.

This example demonstrates that a viscosity modifying, high molecular weight cellulose ether polymer that is insoluble in hot water but soluble in room temperature water can be added to a hot mill base including oils, water, surfactants and ibuprofen and then processed with a modified twin screw extruder to give a dispersion of lipid nanoparticles in a matrix of aqueous water soluble polymer solution.

Examples 35-37

Preparation of Concentrated Lipid Nanoparticle Dispersions Including Oils, Water, Ibuprofen, an Ether Type Polyethoxylated High Hydrophile-Lipophile-Balance (HLB) Surfactant, and Water Soluble Polymers Mill bases were prepared as described for Example 34 that contain other high molecular weight water soluble polymers including acrylates/vinyl crosspolymer (and) PEG-6 (Rapidgel EZ1, 3V Sigma USA, Georgetown, S.C.), sodium carbomer (Lotioncrafter, Eastsound, Wash.) or hyaluronic acid (Making Cosmetics, Redmond. Wash.). The mill bases were prepared by blending polymers as a liquid (Rapidgel EZ1) or dry powders (sodium carbomer and hyaluronic acid) into the premixes at room temperature giving thickened premix solutions. Each mill base was heated to about 100° C. whereupon the viscosity decreased and were fed into a Process 11 twin screw extruder modified with an ice water filed reservoir at a rate sufficient to maintain the screws under the inlet port in a submerged state. The zone temperatures were set to about 95° C. in zones 2, 3, and 4; to 60° C. in zone 5, and to about 10° C. in zones 7, 8, and 9. The screw rotation rate was about 100 rpm. The compositions of the mill bases resulting volume average particle diameters of the extruded dispersions are shown in Table E6.

A sample of the nanoparticle dispersion of Example 37 (8 mL) was placed in a 30 mL beaker with a magnetic stirrer and gently heated to about 60° C. by stirring with a spatula while immersed in a 250 mL beaker filled with hot water. The warm sample was placed on a magnetic stirrer/hotplate and stirred at between about 100 rpm and about 400 rpm while heating at a rate of about 4° C. per minute. The sample was observed to be birefringent when observed between cross polarized films between about 67° C. and about 68° C., Indicating the dispersed nanoparticles have latent lamellar structure.

TABLE E6

|  | Example 34 | Example 35 | Example 36 | Example 37 |
|---|---|---|---|---|
| ceteareth-20 | 11.3 | 11.2 | 11.4 | 11.0 |
| sorbitan oleate | 4.9 | 4.9 | 4.9 | 4.7 |
| isopropyl myristate | 13.8 | 13.7 | 14.0 | 13.2 |
| fractionated coconut oil | 13.8 | 13.7 | 14.0 | 0.0 |
| medium chain trialyceride oil |  |  | 0.0 | 13.1 |
| d-limonene | 4.1 | 4.1 | 4.1 | 3.9 |
| ibuprofen | 5.7 | 5.7 | 5.8 | 5.5 |
| methyl cellulose | 0.04 |  |  |  |
| RapidGel Ez1 |  | 0.3 |  |  |
| sodium carbomer |  |  | 0.1 |  |
| hyaluronic acid |  |  |  | 0.1 |
| NaCl | 0.03 | 0.06 |  |  |
| water | 46.4 | 46.3 | 45.8 | 48.5 |
| total | 100.0 | 100.0 | 100.0 | 100.0 |
| volume average particle size, nm | 53.6 | 55.8 | 83.6 | 54.2 |

Example 38

Preparation of an Edible Concentrated Lipid Nanoparticle Dispersion Including Oils, Water, an Ester Type Polyethoxylated High Hydrophile-Lipophile-Balance (HLB) Surfactant, Lecithin and Cannabidiol A mill base was prepared which contained about 6.4 weight percent (wt. %) polysorbate 80, about 3.3 weight percent (wt. %) polysorbate 20, about 5.8 weight percent (wt. %) of Alcolec XTRA-A lecithin, about 1.3 weight percent (wt. %) glyceryl stearate, about 30.1 weight percent (wt. %) ethyl oleate (Spectrum Chemical and Lab Products, Gardena, Calif.), about 11.7 weight percent (wt. %) medium chain triglyceride oil, about 1.7 weight percent (wt. %) cannabidiol isolate, about 0.03 weight percent (wt. %) NaCl, and about 39.6 weight percent (wt. %) water. All of the ingredients are selected from compounds that are approved by the United States Food and Drug Administration as direct additives for food. The mill base was prepared by warming all ingredients except sodium chloride and water to about 60° C. to give a clear solution, and then adding the sodium chloride as a solution to the warm, stirring lipophilic phase, giving a mill base as an opaque beige dispersion. The mill base (500 grams) was heated and held at a temperature between about 80° C. and about 85° C. and fed into a Process 11 twin screw extruder modified with an ice water filled reservoir at a rate sufficient to maintain the screws under the inlet port in a submerged state. The zone temperatures were set to about 85° C. in zones 2, 3, and 4 and to about 10° C. in zones 5 through 9. The screw rotation rate was about 200 rpm. About 400 grams of extruded processed mill base was collected as a translucent yellow viscous liquid. The volume average particle diameter of the processed dispersion was measured by DLS (Dynamic Light Scattering) and found to be about 131.9 nm. This example demonstrates that a mill base consisting entirely of edible ingredients can be processed with a modified twin screw extruder to give concentrated dispersion of edible lipid nanoparticles in water.

Examples 39-40

Preparation of Edible Concentrated Lipid Nanoparticle Dispersions Including Oils, Water, an Ester Type Polyethoxylated High Hydrophile-Lipophile-Balance (HLB) Surfactant, and Lecithin Mill bases were prepared and processed as described for Example 38. All of the ingredients are approved by the United States FDA as direct additives for food. The composition of the mill bases and the resulting volume average particle diameters of the extruded dispersions as measured by dynamic light scattering are shown in Table E7. Methyl salicylate (Consolidated Chemicals and Solvents LLC, Quakerstown, Pa.).

TABLE E7

|  | Example 38 | Example 39 | Example 40 |
|---|---|---|---|
| polysorbate 80 | 6.4 | 9.4 | 9.7 |
| polysorbate 20 | 3.3 |  |  |
| sodium lauryl sulfate |  | 1.0 |  |

TABLE E7-continued

|  | Example 38 | Example 39 | Example 40 |
|---|---|---|---|
| Alcolec XTRA-A lecithin | 5.8 | 5.7 | 5.8 |
| glyceryl monostearate | 1.3 | 1.3 | 1.3 |
| ethyl oleate | 30.1 | 30.2 | 31.1 |
| medium chain triglyceride oil | 11.7 | 11.4 | 9.1 |
| cannabidiol isolate | 1.7 | 1.9 |  |
| methyl salicylate |  |  | 3.0 |
| BHT |  | 0.1 |  |
| NaCl | 0.03 | 0.03 | 0.04 |
| water | 39.6 | 39.1 | 40.0 |
| total | 100.0 | 100.0 | 100.0 |
| Ratio of water immiscible oil to surfactants | 2.5:1 | 2.4:1 | 2.3:1 |
| HLB weight-mean-square-deviation, $WMSD_{HLB}$ | 4.15 | 3.95 | 3.90 |
| volume average particle size, nmn | 131.9 | 80.1 | 74.1 |

Example 41

Preparation of a Concentrated Lipid Nanoparticle Dispersion Including Oils, Water, an Ether Type Polyethoxylated High Hydrophile-Lipophile-Balance (HLB) Surfactant, a Phospholipid and an Oil Soluble Vitamin A mill base was prepared which contained about 6.6 weight percent (wt. %) laureth-23, about 5.1 weight percent (wt. %) PEG100 stearate, about 0.6 weight percent (wt. %) Phospholipon 90G, about 5.0 weight percent (wt. %) sorbitan oleate, about 5.0 weight percent (wt. %) stearic acid, about 16.6 weight percent (wt. %) isopropyl myristate, about 1.2 weight percent (wt. %) capric/caprylic triglyceride oil, about 5.0 weight percent (wt. %) tocopheryl acetate (oil soluble vitamin E), and about 55.1 weight percent (wt. %) water. The mill base was prepared by warming all ingredients except water to about 60° C. to give a clear solution, and then adding water to the warm, stirring lipophilic phase, giving a mill base as an opaque dispersion. The mill base was heated to about 90° C. and fed while hot into a Process 11 twin screw extruder modified with an ice water filled reservoir at a rate sufficient to maintain the screws under the inlet port in a submerged state. The zone temperatures were set to about 90° C. in zones 2, 3, and 4 and to about 15° C. in zones 6, 7, 8, and 9. The screw rotation rate was about 200 rpm. About 400 grams of extruded processed mill base was collected as a translucent very light yellow dispersion. The volume average particle diameter of the processed dispersion was measured by DLS (Dynamic Light Scattering) and found to be about 65.5 nm. This example demonstrates that processing a mill base including oils, water, surfactants and an oil soluble vitamin with a modified twin screw extruder gives a tocopheryl acetate nanoparticle containing dispersion with about 44.9 weight percent (wt. %) nanoparticles.

Examples 42-50

Preparation of Concentrated Lipid Nanoparticle Dispersions Including Oils, Water, an Ether Type Polyethoxylated High Hydrophile-Lipophile-Balance (HLB) Surfactant, an oil Soluble Vitamin or a Botanical Extract Mill bases were prepared as described above with the compositions shown in Table AE. Tocopheryl acetate (Making Cosmetics, Redmond, Wash.), ascorbyl palmitate (Solaray, Park City Utah (Liposomal Vitamin® C product), retinyl palmitate (Making Cosmetics, Redmond, Wash.), Youth Garden oil blend containing tetrahexyldecyl ascorbate, red raspberry (rubus ideaus) seed oi, cranberry (vaccinium macrocarpon) seed oil, tomato (Solanum lycopersicum) seed oi, black cumin (nigella sativa) seed oil, and mixed tocopherols (Vitamin E) is a product of Botanic Innovations, Spooner Wis. Birch bark extract (The Actives Factory, Waconia, Minn.), cannabidiol (Hemp Acres, Waconia, Minn.), frankincense essential oil (Piping Rock, Ronkonkoma, N.Y.), omega-3 fatty acid oil (iWi, Houston, Tex.), resveratrol (Bulk Actives, New Taipei City, Taiwan), undecylenic acid (Sigma-Aldrich), stearic acid (Making Cosmetics, Redmond, Wash. or Soaper's Choice, Des Plaines, Ill.), soy biodiesel (methyl soyate) (Minnesota Soybean Processors. Brewster, Minn.), diisopropyl adipate (Alzo International Inc., Sayreville, N.J.), and octanoic acid (P&G Chemicals, Cincinnati, Ohio).

Mill bases were processed using a Process 11 twin screw extruder modified with a reservoir filed with ice water. The temperature of the mill base when fed into the modified extruder and the set points of the extruder barrel zones were varied as shown in Table E8. For each of the Examples, the first three zones (zones 2 through 4) had the same temperature set points and the last three zones (zones 6-8) had the same temperature set points which were generally cooler than the set points of the first three zones while the zone 5 set point was controlled independently. Compositions and processing data and volume average particle diameters of the processed dispersions are also shown in Table E8.

When a sample of the nanoparticle dispersion of Example 49 was extruded onto a glass slide and allowed to partially dry, it was observed to be birefringent when viewed through cross polarizing films, indicating that it has latent lamellar structure. When stored in a closed container at 40° C. for about 6 days, the sample was stable to phase separation.

What these Examples show is that processing a mill base including oils, water, surfactants with oil soluble vitamins and provitamins, and botanically derived ingredients with a modified twin screw extruder gives a nanoparticle dispersion with between about 40 and about 50 weight percent (wt. %) nanoparticle concentrations. Oil soluble vitamins and provitamins exemplified include, for example, tocopheryl acetate (Vitamin E), ascorbyl palmitate (Vitamin C), retinyl palmitate (Vitamin A), tetrahexyldecyl ascorbate (Vitamin C), mixed tocopherols (Vitamin E), and coenzyme Q. Exemplified botanically derived ingredients include, for example, birch bark extract, cannabidiol, frankincense essential oil, omega-3 fatty acid oil, resveratrol, red raspberry (rubus ideaus) seed oil, cranberry (vaccinium macrocarpon) seed oil, tomato (Solanum lycopersicum) seed oil, black cumin (nigella sativa) seed oil, undecylenic acid, soy lecithin, stearic acid, and octanoic acid. Oils exemplified include, for example, capric/caprylic triglyceride oil, medium chain triglyceride oil, isopropyl myristate, diisopropyl adipate, soy biodiesel (methyl soyate), mineral oi, and hydrocarbons.

TABLE E8

| | Ex. 41 | Ex. 42 | Ex. 43+0 | Ex. 44 | Ex. 45 | Ex 46 | Ex 47 | Ex. 48 | Ex. 49 | Ex. 50 |
|---|---|---|---|---|---|---|---|---|---|---|
| laureth-23 | 6.6 | | | | | | 6.7 | | | |
| PEG100 stearate | 5.1 | 5.1 | | | | | 5.1 | | | |
| laureth-30 | 6.8 | | | | | | | | | |
| ceteareth-20 | | | 9.6 | | 10.1 | 8.0 | | 10.1 | | 9.8 |
| ceteareth-30 | | | | 9.5 | | | | | 9.8 | |
| Phospholipon 90G | 0.6 | 0.7 | | 0.6 | | 0.4 | 0.6 | | | |
| Alcolec XTRA-A soy lecithin | | | | | | | | | 3.3 | 2.7 |
| sorbitan oleate | 5.0 | 2.6 | | 4.3 | | | 5.0 | | 4.4 | 5.2 |
| sorbitan stearate | | | 2.8 | | 4.5 | 3.6 | | 10.1 | | |
| stearic acid | 5.0 | | | | 2.3 | 1.8 | | | | |
| octanoic acid | | | | 4.8 | | | 5.0 | | | |
| isopropyl myristate | 16.6 | 12.9 | 10.9 | 12.3 | 11.3 | 8.9 | 16.7 | 10.0 | 13.1 | 7.8 |
| CCT oil | 1.2 | 1.4 | | 12.7 | | | 1.1 | 8.6 | | |
| MCT oil | | | 17.0 | | 11.4 | 11.0 | | | 13.1 | 8.6 |
| diisopropyl adipate | | 12.8 | | | | | | | | |
| limonene | | | | 3.5 | | | | | | |
| soy biodiesel | | | | | | 8.9 | | | | |
| light mineral oil | | | | | | | | 9.4 | | |
| Siclone SR-5 | | | | | | | | | | 5.3 |
| tocopheryl acetate | 5.0 | | 2.2 | | 2.3 | | | | | |
| ascorbyl palmitate | | 2.6 | 2.1 | | | | | | | |
| birch bark extract | | | 2.1 | | 2.0 | | | | | 1.0 |
| retinyl palmitate | | | 2.1 | | 2.3 | 1.8 | | | | |
| cannabidiol isolate | | | | 1.6 | | 0.0 | | | | |
| frankincense oil | | | | | | 3.6 | | | | |
| omega-3 oil | | | | | | | 2.6 | | | |
| Coenzyme Q | | | | | | | | 0.5 | | |
| resveratrol | | | | | | | | 0.5 | | |
| undecylenic acid | | | | | | | | | 4.9 | |
| Youth Garden | | | | | | | | | | 3.2 |
| Optiphen | | | | | | 0.7 | | 1.2 | | |
| BHT | | | | | | | | | | 0.5 |
| tetrasodium EDTA | | | | | | | | | | 0.5 |
| citric acid | | | | | | | | | | 0.2 |
| NaCl | | 0.04 | 0.04 | 0.04 | 0.04 | 0.03 | 0.04 | 0.04 | 0.05 | |
| water | 55.1 | 55.0 | 50.9 | 50.8 | 53.9 | 51.3 | 57.1 | 49.5 | 51.3 | 55.3 |
| Ratio of hydrophobic nonionic surfactant to polyethoxylated high HLB surfactant | 0.90:1 | 0.28:1 | 0.29:1 | 1.0:1 | 0.67:1 | 0.73:1 | 0.90:1 | 1.0:1 | 0.79:1 | 0.81:1 |
| Ratio of water immiscible oil to surfactants | 0.80:1 | 1.8:1 | 2.4:1 | 1.5:1 | 1.3:1 | 2.2:1 | 0.79:1 | 1.4:1 | 1.5:1 | 1.2:1 |
| volume average diameter | 65.5 | 50.5 | 55.7 | 89.9 | 64.7 | 108 | 40 | 41.3 | 44.1 | 86.7 |
| feed temperature | 90 | 90 | 85 | 85 | 88 | 84 | 20 | 90-100 | 90-100 | 90-100 |
| barrel set points zones 2-4 | 90 | 90 | 85 | 80 | 90 | 85 | 95 | 95 | 95 | 95 |
| barrel set point zones 5 | 15 | 15 | 60 | 60 | 60 | 60 | 60 | 10 | 10 | 10 |
| barrel set points zones 6-8 | 15 | 15 | 10 | 10 | 10 | 10 | 10 | 10 | 10 | 10 |

Example 51

Preparation of a Concentrated Lipid Nanoparticle Dispersion Including Oils, Water, an Ether Type Polyethoxylated High Hydrophile-Lipophile-Balance (HLB) Surfactant, Ibuprofen and a Cryoprotectant A mill base was prepared which contained about 11.1 weight percent (wt. %) ceteareth-20, about 5.5 weight percent (wt. %) ibuprofen, about 4.8 weight percent (wt. %) sorbitan oleate, about 13.5 weight percent (wt. %) isopropyl myristate, about 13.5 weight percent (wt. %) medium chain triglyceride oil, about 3.9 weight percent (wt. %) limonene, about 16.0 percent glycerin (Crafter's Choice, Independence, Ohio), about 2.0 weight percent (wt. %) dimethyl sulfoxide (DMSO, product of Heiltropfen, London, UK), about 0.02 weight percent (wt. %) NaCl, and about 29.7 weight percent (wt. %) water. The mill base was prepared by warming all ingredients except glycerin, DMSO and water to about 60° C. to give a clear solution, and then adding NaCl, water, glycerin and DMSO to the warm, stirring lipophilic phase giving a mill base as an opaque dispersion. The mill base has about 52.3 weight percent (wt. %) lipophilic phase and about 47.7 weight percent (wt. %) aqueous phase. The mill base (500 grams) was heated and held at a temperature between about 90° C. and about 100° C. and fed while hot into a Process 11 twin screw extruder modified with an ice water containing reservoir at a rate sufficient to maintain the screws under the inlet port in a submerged state. The zone temperatures were set to about 95° C. in zones 2, 3, and about 10° C. in zones 6, 7, 8, and 9. The screw rotation rate was about 200 rpm. About 400 grams of extruded processed mill base was collected as a transparent colorless gel. The particle size of the processed dispersion was measured using dynamic light scattering and found to have volume average particle size about 58.3 nm. When the sample was stored overnight in a freezer at −15° C. and thawed, the appearance remained transparent and the volume average particle diameter as measured by DLS (Dynamic Light Scattering) was 58.5 nm. By comparison, when the nanoparticle dispersion of Example 5 without DMSO and glycerin was stored overnight, the volume average particle diameter increased to 3840 nm and the composition phase separated at room temperature overnight. A 25 mL sample of the nanoparticle dispersion was placed in a 30 mL beaker with a magnetic stirrer and gently heated to 40° C. by stirring with a spatula while immersed in a 250 mL beaker filled with hot water. The warm sample was stirred on a magnetic stirrer/hotplate between 100 rpm and 400 rpm while heating at a rate of about 4° C. per minute. The sample was observed to be birefringent when observed between cross polarized films between about 43° C. and 47° C., indicating the dispersed nanoparticles have latent lamellar structure. This example demonstrates that that processing a mill base including oils, water, surfactants and a cryoprotectant mixture of glycerin and DMSO using a modified twin screw extruder gives a nanoparticle containing dispersion with latent lamellar structure that is stable to freezing and thawing. This example demonstrates that that processing a mill base including oils, water, surfactants and a cryoprotectant mixture of glycerin and DMSO using a modified twin screw extruder gives a nanoparticle containing dispersion that is stable to freezing and thawing.

Examples 52-53

Preparation of Concentrated Lipid Nanoparticle Dispersion Including Oils, Water, an Ether Type Polyethoxylated High Hydrophile-Lipophile-Balance (HLB) Surfactant, and Cryoprotectants Mill bases were prepared that contain cryoprotectants including glycerin, trehalose, propylene glycol, and sorbitol as shown in Table AF. The mill bases were prepared as described for Example 51, that is, lyophilic ingredients (al ingredients except for NaCl, glycerin, propylene glycol, trehalose, sorbitan, and ethylene glycol blend) were mixed and warmed to about 80° C. to give a transparent liquid and then the remaining ingredients were added to give opaque mill base dispersions. Propylene glycol (BASF, Florham Park, N.J.), and trehalose (Spectrum Chemicals). The ethylene glycol blend was Menards 50/50 Pre-diluted Extended Life Antifreeze/Coolant (Menards Inc., Eau Claire, Wis.) and contained water, ethylene glycol and diethylene glycol. Each mill base was heated to about 100° C. whereupon the viscosity decreased and the hot mill base was fed into a Process 11 twin screw extruder modified with an ice water filled reservoir at a rate sufficient to maintain the screws under the inlet port in a submerged state. The zone temperatures were set to about 95° C. in zones 2, 3, and 4 and to about 10° C. in zones 8, 7, 8, and 9. The screw rotation rate was about 200 rpm. When the samples were stored overnight in a freezer at about −15° C. and thawed, their appearances remained unchanged and the volume average particle diameter as measured by DLS (Dynamic Light Scattering) remained below about 150 nm. The volume average particle diameters of the nanoparticle dispersions as prepared and those of samples that were frozen and thawed as measured by dynamic light scattering and composition of the mill bases and particle sizes are shown in Table E9.

TABLE E9

|  | Example 51 | Example 52 | Example 53 |
| --- | --- | --- | --- |
| ceteareth-20 | 11.1 | 8.4 | 10.8 |
| PEG100 stearate |  | 2.3 |  |
| sodium lauryl sulfate |  | 1.1 | 1.0 |
| sorbitan oleate | 4.8 | 4.9 | 4.7 |
| isopropyl myristate | 13.5 | 13.8 | 13.3 |
| medium chain triglyceride oil | 13.5 | 13.8 | 13.2 |
| d-limonene | 3.9 | 3.8 | 4.0 |
| ibuprofen | 5.5 | 5.8 | 5.5 |
| glycerin | 16.0 | 3.8 | 8.8 |
| DMSO | 2.0 |  |  |
| trehalose |  | 3.8 |  |
| propylene glycol |  | 3.8 |  |
| sorbitol |  | 3.8 |  |
| ethylene glycol blend |  |  | 18.2 |
| NaCl | 0.02 | 0.03 | 0.02 |
| water | 29.7 | 30.7 | 20.5 |
| total | 100.0 | 100.0 | 100.0 |
| volume average particle size, nm | 56.3 | 139.3 | 258.6 |
| volume average particle size after freezing and thawing, nm | 56.5 | 142.1 | 296.0 |

Example 54

Figure 4:
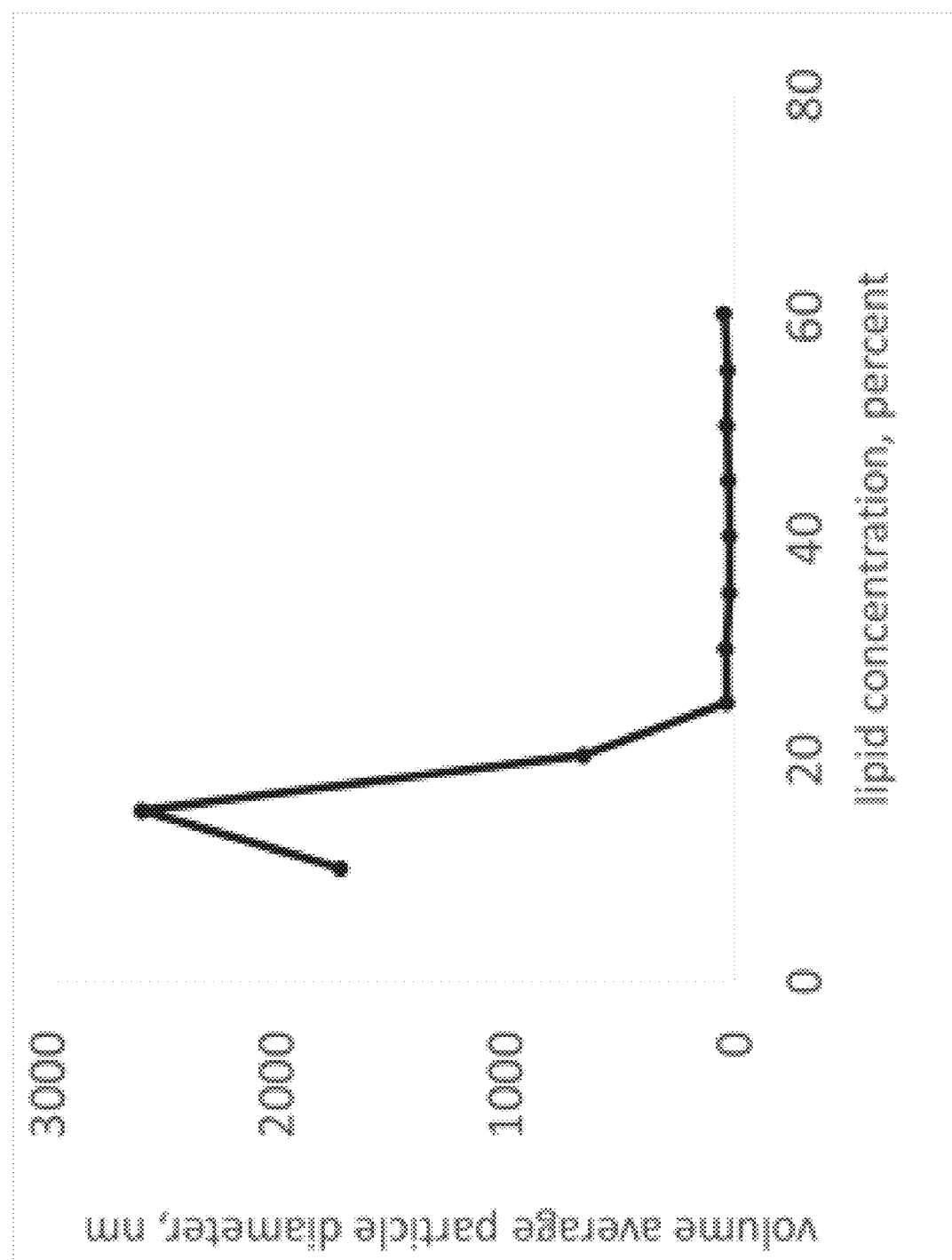
FIG. 4 is a plot of volume average particle diameters vs weight percent lipid concentration for a series of mill bases with between 10 and 60 weight percent lipids.

Processing Lipid Dispersion Compositions Including Oils, Water, an Ether Type Polyethoxylated High Hydrophile-Lipophile-Balance (HLB) Surfactant, and lidocaine with Between about 10 and about 60 Weight Percent (Wt. %) Lipid Concentrations A mill base was prepared which contained about 11.9 weight percent (wt. %) ceteareth-20, about 3.0 weight percent (wt. %) lidocaine, about 12.0 weight percent (wt. %) sorbitan stearate, about 12.0 weight percent (wt. %) isopropyl myristate, about 10.3 weight percent (wt. %) capric/caprylic triglyceride, oil, about 11.1 weight percent (wt. %) light mineral oil, about 0.03 weight percent (wt. %) NaCl, and about 39.6 weight percent (wt. %) water. The mill base was prepared by warming all ingredients except sodium chloride and water to about 60° C. to give a clear solution, and then adding the sodium chloride as a solution to the warm, stirring lipophilic phase, giving a mill base as an opaque dispersion with about 60.3 weight percent (wt. %) lipophilic phase. A portion of the mill base (500 grams) was heated and held at about 80° C. and fed while hot into a Process 11 twin screw extruder modified with an ice water containing reservoir at a rate sufficient to maintain the screws under the inlet port in a submerged state. The zone temperatures were set to about 80° C. in zones 2, 3, and 4; to about 60° C. in zone 5, and to about 10° C. in zones 7, 8, and 9. The screw rotation rate was about 200 rpm. About 400 grams of extruded processed mill base was collected as a hazy transparent colorless gel. The particle size of the processed dispersion was measured using dynamic light scattering and found to have volume average particle size about 50.1 nm. Portions of the mill base were diluted with water to give diluted mill bases with between about 10.2 weight percent (wt. %) and about 55.2 weight percent (wt. %) lipophilic phase which were processed with the modified twin screw extruder under conditions identical to those for the about 60.3 weight percent (wt. %) lipophilic phase mill base. The volume average particle diameters for each processed mill charge is shown in Table E10 and a plot of particle diameters vs lipophilic phase content is shown in FIG. 4. This example demonstrates compositions including oils, water and surfactants with between about 25 weight percent (wt. %) and up to about 60 weight percent (wt. %) lipophilic phase content can be processed using a modified twin screw extruder to give nanoparticle dispersions.

TABLE E10

| lipophilic phase concentration, weight percent (wt. %) | volume average particle size, nm |
|---|---|
| 10.2 | 1725.3 |
| 15.4 | 2593.6 |
| 20.5 | 663.0 |
| 25.2 | 34.6 |
| 30.1 | 38.8 |
| 35.1 | 24.8 |
| 40.2 | 23.4 |
| 45.3 | 29.7 |
| 50.2 | 35.0 |
| 55.2 | 33.9 |
| 60.3 | 50.1 |

Example 55

Processing of a Mill Base Including Sorbitan Oleate, Laureth-23, PEG-100 Stearate, Dioleyl Phosphatidyl Choline, Isopropyl Myristate, d-Limonene, Ibuprofen and Preservative to Give a Nanoparticle Dispersion A mill base was prepared consisting of about 3.0 weight percent (wt. %) sorbitan oleate (Making Cosmetics, Redmond, Wash.), about 0.5 weight percent (wt. %) dioleyl phosphatidyl choline (Phospholipon 90G, product of Lipold USA, Newark, N.J.), about 1.1 weight percent (wt. %) of capric/caprylic triglyceride oil (Lotioncrafter, Eastsound, Wash.), about 6.1 weight percent (wt. %) laureth-23 (Lotioncrafter, Eastsound, Wash.), about 4.6 weight percent (wt. %) PEG 100 stearate (Myrj S100, available from Spectrum Chemical), about 20.2 weight percent (wt. %) isopropyl myristate (Lotioncrafter, Eastsound, Wash.), about 5.1 weight percent (wt. %) ibuprofen (BASF, Florham Park, N.J.), about 5.1 weight percent (wt. %) d-limonene (Eco-Clean Solutions, Copaigue, N.Y.), about 0.5 weight percent (wt. %) Optiphen preservative (Lotioncrafter, Eastsound, Wash.), about 0.1 weight percent (wt. %) tetrasodium EDTA (Making Cosmetics, Redmond. Wash.), about 0.03 weight percent (wt. %) anhydrous citric acid and about 53.7 weight percent (wt. %) water. The weight ratio of hydrophobic nonionic surfactants to polyethoxylated high hydrophile-lipophile-balance (HLB) surfactant was about 0.33 to about 1. The mill base was prepared by heating al ingredients except for water, sodium EDTA, and Optiphen to about 60° C., then adding Optiphen and then the solution of sodium chloride plus sodium EDTA plus citric acid to give a viscous, opaque dispersion. The mill base was charged to a Gigawort™ 4.4 gallon electric boil kettle (Northern Brewer) and heated to 78° C. and then processed in a Thermo Fisher Process 24 twin screw extruder with a screw diameter=24 mm and total processing length of about 96 cm (40 L/D). The Process 24 twin screw extruder has 10 temperature zones, each of which is approximately 4 L/D in length (the first zone is not temperature controlled). For each of the two screws, the first 21.3 cm (8.9 L/D) consisted of 1/1 pitch conveying elements, the next 10.6 cm (4.5 L/D) consisted of mixing elements, the next 10.6 cm (4.5 LID) consisted of 1/1 pitch conveying elements, the next about 5.3 cm (2.2 L/D) consisted of mixing elements, and the final about 48 cm (20 L/D) consisted of 1/1 pitch conveying elements. Before beginning to introduce premix to the extruder, the extruder was conditioned by setting all of the temperature zone set points to about 10° C. and pumping cold water at about 10° C. with a flow rate of about 13 L/min through the cooling system for about 30 minutes. Immediately before beginning introduction of mill base, the temperature set points in zones 2, 3 and 4 were increased to about 95° C. With the screw rotation rate at about 100 rpm, introduction of mill base heated to about 78° C. began with the temperatures in zone 2=95° C., zone 3=94° C., zone 4=89° C., zone 5=62° C., zone 6=37° C., zone 7=32° C., zone 8=29° C., zone 9=27° C., and zone 10=25° C. After a total of about 3.7 Kg of mill base was processed, the temperature in zone 2=95° C., zone 3=94° C., zone 4=90° C., zone 5=65° C., zone 6=39° C., zone 7=34° C., zone 8=30° C., zone 9=29° C., and zone 10=27° C. The extruded nanoparticle dispersion had the appearance of a translucent ivory colored liquid having viscosity approximately that of honey. When diluted with water and analyzed by DLS (Dynamic Light Scattering), the sample was observed to have volume average particle diameter about 95.8 nm. This example demonstrates that processing a mill base composition including ibuprofen, a hydrophobic drug, with a conditioned 24 mm twin-screw extruder in which the maximum ΔT=88° C. gives an extruded product with volume average particle size less than about 100 nm.

A sample of the nanoparticle dispersion product was tested for latent lamellar structure by heating and observing for optical birefringence and negative peaks in the plot of electrical conductivity vs temperature. Nanoparticle dispersion product (about 108.9 g) in a 150 mL Pyrex beaker was warmed gently in a microwave oven on defrost cycle to about 45° C., making it sufficiently fluid so as to be stirred using a magnetic stirrer/hotplate with a stirring rate of between about 100 and about 400 rpm. The hotplate was set to heat the stirring sample at a rate of about 2° C. per minute and the conductivity was measured about every 10 seconds using a Thermo Scientific Orion 3-star Conductivity Meter Model 1114000 with a 013005MD 4-cell conductivity cell electrode. Normalized conductivity was calculated as the ratio of conductivity to the maximum conductivity measured in the temperature range of about 45° C. to about 80° C. and the first derivative of normalized conductivity vs temperature was calculated for each conductivity and temperature pair between about 45° C. and about 80° C. Plots of normalized conductivity and the first derivative of normalized conductivity are shown in FIG. 5. The plot of normalized conductivity vs temperature shows a small negative peak at about 75° C. and the first derivative plot shows a peak with amplitude about 0.17 C$^{-1}$ at about 75° C. The presence of a negative peak in the plot of conductivity vs temperature and the amplitude of the first derivative plot with greater than about 0.15 C$^{-1}$ indicate nanoparticles in the dispersion product have a latent lamellar structure. During the heating experiment, the nanoparticle dispersion composition became transparent and was observed to be birefringent between about 71° C. and about 74° C. when observed between two crossed pieces of polarizing film. The observation of optical birefringence in the heated nanoparticle dispersion indicates that nanoparticles in the dispersion have a latent lamellar structure.

When the sample was stored at 40° C. for about six months, it was stable with respect to phase separation.

Example 58

Processing of a Mill Base Including Sorbitan Stearate, Ceteareth-20, Isopropyl Myristate, Capric/Caprylic Triglyceride Oil, Mineral Oil, Cannabidiol and Preservative to Give a Nanoparticle Dispersion A mill base was prepared consisting of about 5.6 weight percent (wt. %) sorbitan stearate (Lotioncrafter, Eastsound, Wash.), about 10.1 weight percent (wt. %) ceteareth-20 (Making Cosmetics, Redmond, Wash.), about 9.4 weight percent (wt. %) of capric/caprylic triglyceride oil (Lotioncrafter, Eastsound, Wash.), about 9.3 weight percent (wt. %) isopropyl myristate (Lotioncrafter, Eastsound, Wash.), about 9.4 weight percent (wt. %) light mineral oil (Drakeol 7, available from CQ Concepts, Ringwood, Ill.), about 1.1 weight percent (wt. %) cannabidiol (Mile High Labs, Boulder, Colo.), about 1.1 weight percent (wt. %) Optiphen preservative (Lotioncrafter, Eastsound, Wash.), about 0.1 weight percent (wt. %) BHT, about 0.2 weight percent (wt. %) tetrasodium EDTA (Making Cosmetics, Redmond, Wash.), about 0.08 weight percent (wt. %) anhydrous citric acid and about 51.5 weight percent (wt. %) water with about 750 mg/L sodium chloride. The weight ratio of hydrophobic nonionic surfactants to polyethoxylated high hydrophile-lipophile-balance (HLB) surfactant was 0.about 55 to about 1. The mill base was prepared by heating all ingredients except for water, sodium EDTA, and Optiphen to about 60° C., then adding Optiphen and then the solution of sodium chloride plus sodium EDTA plus citric acid to give a viscous, opaque dispersion. The mill base was charged to a Gigawort™ 4.4 gallon electric boil kettle (Northern Brewer) and heated to 87° C. and then processed in a Thermo Fisher Process 24 twin screw extruder with a screw diameter=24 mm and total processing length of about 96 cm (40 LD). The Process 24 twin screw extruder has 10 temperature zones, each of which is approximately 4 L/D in length (the first zone is not temperature controlled). For each of the two screws, the first 21.3 cm (8.9 L/D) consisted of 1/1 pitch conveying elements, the next 10.6 cm (4.5 LID) consisted of mixing elements, the next 10.6 cm (4.5 L/D) consisted of 1/1 pitch conveying elements, the next about 5.3 cm (2.2 L/D) consisted of mixing elements, and the final about 48 cm (20 L/D) consisted of 1/1 pitch conveying elements. Before beginning to introduce premix to the extruder, the extruder barrel was conditioned by setting all of the temperature zone set points to about 10° C. and pumping cold water at about 10° C. with a flow rate of about 13 L/min through the cooling system for about 30 minutes. Just before beginning introduction of the mill base to the extruder, the temperature set points in zones 2, 3, and 4 were raised to about 95° C. With the screw rotation rate at about 150 rpm, introduction of mill base heated to about 87° C. began with the temperatures in zones 2-10=93° C., 84° C., 74° C., 36° C., 23° C., 22° C., 18° C., 17° C., and 16° C., respectively. After a total of 2.8 Kg of mill base was processed, the temperatures in zones 2-10 were about 95° C., 92° C., 82° C., 49° C., 32° C., 30° C., 25° C., 22° C., and 21° C., respectively. The extruded nanoparticle dispersion had the appearance of a translucent white liquid having viscosity approximately that of vegetable oil. When diluted with deionized water analyzed by DLS (Dynamic Light Scattering), the sample was observed to have volume average particle diameter about 54.7 nm. When the sample was stored at 40° C. for about six months, it was stable with respect to phase separation.

This example demonstrates that processing a mill base composition including cannabidiol, a hydrophobic botanical extract, with a 24 mm twin-screw extruder with a conditioned barrel in which the maximum ΔT=69° C. gives an extruded product with volume average particle size less than about 60 nm and stability with respect to phase separation for over six months.

Example 57

Processing of a Mill Base Including Ceteareth-20, Medium Chain Triglyceride Oil, Isopropyl Myristate, Mineral Oil, Sorbitan Oleate, Soy Lecithin, Phenoxy Ethanol, BHT, Caprylyl Glycol, EDTA, and Citric Acid Using a Modified Twin Screw Extruder A mill base was prepared consisting of about 9.9 percent ceteareth-20, about 9.9 percent medium chain triglyceride oil, about 9.2 percent isopropyl myristate, about 6.6 percent mineral oil, about 5.3 percent sorbitan oleate, about 1.0 percent soy lecithin, about 0.7 percent BHT, about 0.6 percent phenoxy ethanol, about 0.6 percent tetrasodium EDTA, about 0.4 percent caprylyl glycol, about 0.2 percent citric acid and about 55.8 percent water. The weight ratio of hydrophobic nonionic surfactants to polyethoxylated high hydrophile-lipophile-balance (HLB) surfactant was about 0.64 to about 1. The mill base was prepared by heating all ingredients except for water, sodium EDTA, and citric acid to about 60° C., then adding solution of sodium chloride plus sodium EDTA plus citric acid to give a viscous, opaque dispersion. The mil base volume average diameter was about 1270 nm and number average diameter was about 171 nm.

A Leistritz 27 mm twin screw extruder was modified by removing the cooling water manifold and the hoses between the manifold and the barrel. Fittings screwed into the barrel connecting the barrel to cooling water manifold hoses were replaced with hose barbs and ⅜ inch ID braided flexible clear PVC tubing was used to connect the motor end entrance of each barrel section cooling channel to the die end entrance of the cooing channel of the preceding (closer to the motor) section of the extruder barrel. Tap water from a hose sink connection was routed through a Copperhead® 50-foot copper immersion wort chiller (Northern Brewer, St. Paul Minn.) submerged in a 5 gallon pail of stirring ice water and then to the die end entrance of the last temperature control zone (zone 9, nearest the die). Cooing water flowed in the direction from the die to the motor for each of zones in reverse order (that is, zone 9 then zone 8, zone 7, zone 6, zone 5, zone 4 and zone 3), exited the barrel at the motor end fitting of the third temperature control zone through a garden hose leading to drain.

The pellet feeder of the extruder was removed leaving the tops of the screws visible and replaced with a system for introducing mill base. The mill base introduction system included a peristaltic pump for pumping mill base from a five gallon pail through the inner channel of a stainless steel counter flow wort chiller available (Northern Brewer) into the zone 1 inlet while water was recirculated from a Gigawort™ 4.4 gallon electric boil kettle (Northern Brewer) in a counter flow direction through the outer channel. The holdup volume of the inner channel of the counter flow wort chiller is about 285 mL.

The screw configuration in unites of length over diameter was: L/D 0.0-1.1:15 mm pitch intermeshing conveying, L/D 1.1-4.5:40 mm pitch non-intermeshing conveying, L/D 4.5-6.7:30 mm pitch intermeshing conveying, L/D 6.7-10.0:30 mm pitch intermeshing conveying, L/D 10.0-11.1:30 degree kneading block, L/D 11.1-13.3:60 degree kneading block, L/D 13.3-16.6:40 mm pitch intermeshing conveying, L/D 16.6-18.9:30 mm pitch intermeshing conveying, L/D 18.9-20.0:30 degree kneading block, L/D 20.0-22.2:60 degree kneading block, L/D 22.2-23.3:30 mm pitch intermeshing conveying, L/D 23.3-25.5:90 degree kneading discs, L/D 25.5-26.6:20 mm pitch intermeshing conveying, L/D 26.6-28.8:90 degree kneading discs, L/D 28.8-29.9:40 mm pitch intermeshing conveying, L/D 29.9-33.3:40 mm pitch intermeshing conveying, and L/D 33.3-38.6:30 mm pitch intermeshing conveying.

With the water recirculating between the Gigawort™ 4.4 gallon electric boil kettle and the outer channel of the counter flow wort chiller maintained at about 96° C., mill base was pumped through the counter flow wort chiller and admitted into the inlet previously used for the pellet feeder in zone 1 at a rate of 275 g/minute with extruder zone temperatures maintained at steady state temperatures of about 56° C., 54° C., 17° C., 15° C., 13° C., 14° C., 18° C., and 15° C., for Zones 1 through 8, respectively. The temperature of the mill base entering the extruder was about 90° C. and the extruded mi base temperature was about 15° C. The screw speed was about 200 rpm and the average residence time of mill base was approximately 60 seconds in the counter flow wort chiller and approximately 40 seconds in the extruder barrel. The extruded mil base had the appearance of a light yellow, hazy transparent liquid with viscosity about that of vegetable oil. The volume average particle diameter was about 47.7 nm and the number average particle diameter was about 34.1 nm when measured by DLS (Dynamic Light Scattering).

This example demonstrates that processing a coarse, non-nanoparticle emulsion including an ether type polyethoxylate hydrophilic surfactant, oil and water by passing it successively through a heat exchanger and a modified twin screw extruder with a total residence time less than about 2 minutes is effective to produce a about 44 weight percent (wt. %) nanoparticle dispersion with volume average particle diameter equal to about 50 nm.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fail within the four corners of a claim that recites those three steps.

Similarly, except as explicitly required by claim language, a single substance or component may meet more than a single functional requirement, provided that the single substance or component fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicant reserves the right to physically incorporate into this specification any and all materials and Information from any such patents, applications, publications, scientific articles, web sites, electronically available information, and other referenced materials or documents. Applicant reserves the right to physically incorporate into any part of this document, including any part of the written description, the claims referred to above including but not limited to any original claims.

What is claimed is:

1. A nanoparticle dispersion for topical delivery to skin of a mammal, the nanoparticle dispersion comprising;
   one or more hydrophobic drugs selected from the group consisting of aspirin, benzocaine, hydrocortisone, and lidocaine;
   one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30;
   one or more low hydrophile-lipophile-balance (HLB) surfactants selected from the group consisting of stearic acid, sorbitan oleate, and sorbitan stearate;
   one or more water immiscible oils selected from the group consisting of cocoyl caprate/caprylate, benzyl alcohol, diisopropyl adipate, capric/caprylic triglyceride oil, isopropyl rnyristate, limonene, medium chain triglyceride oil, mineral oil, oleyl alcohol, sesame oil, and a combination of isohexadecane, isododecane, and a $C_{13-15}$ alkane;
   water, and
      wherein the one or more hydrophobic drugs each independently having a log P>1 do not form crystals from the nanoparticle dispersion for greater than about 8 months at a temperature from about 18° C. to about 22° C.;
wherein the dispersion is without lamellar structure; and
wherein the dispersion has a latent lamellar structure.

2. The nanoparticle dispersion of claim 1, further comprising one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80.

3. The nanoparticle dispersion of claim 1, further comprising one or more phospholipid low hydrophile-lipophile-balance (HLB) surfactants selected from the group consisting of phosphatidylcholine and lecithin.

4. The nanoparticle dispersion of claim 1, further comprising one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80 and one or more phospholipid low hydrophile-lipophile-balance (HLB) surfactants selected from the group consisting of phosphatidylcholine and lecithin.

5. The nanoparticle dispersion of claim 1, further comprising one or more non-polyethoxylated high hydrophile-lipophile-balance (HLB) surfactants selected from the group consisting of cocoglucoside, decyl glucoside, and xylityl caprate/caprylate.

6. The nanoparticle dispersion of claim 1, wherein the nanoparticle dispersion has a weight square mean deviation value of hydrophile-lipophile-balance (HLB) ($WMSD_{HLB}$) between about 1.5 and about 4.5.

7. The nanoparticle dispersion of claim 1, wherein the nanoparticle dispersion has a volume average particle size less than about 150 nm.

8. A nanoparticle dispersion for topical delivery to skin of a mammal, the nanoparticle dispersion comprising;
one or more hydrophobic drugs selected from the group consisting of aspirin, benzocaine, hydrocortisone, and lidocaine;
one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30;
one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80;
one or more low hydrophile-lipophile-balance (HLB) surfactants selected from the group consisting of stearic acid, sorbitan oleate, and sorbitan stearate;
one or more water immiscible oils selected from the group consisting of cocoyl caprate/caprylate, benzyl alcohol, diisopropyl adipate, capric/caprylic triglyceride oil, isopropyl myristate, limonene, medium chain triglyceride oil, mineral oil, omega 3 fatty acid, oleyl alcohol, sesame oil, and a combination of isohexadecane, isododecane, and a $C_{13-15}$ alkane;
water, and
wherein the one or more hydrophobic drugs each independently having a log P>1 do not form crystals from the nanoparticle dispersion for greater than about 8 months at a temperature from about 18° C. to about 22° C.; and wherein the dispersion exhibits a positive peak between about 45° C. and 80° C. in the first derivative plot of normalized conductivity versus temperature, the positive peak having a peak amplitude greater than about $0.1° C.^{-1}$.

9. The nanoparticle dispersion of claim 8, further comprising one or more phospholipid low hydrophile-lipophile-balance (HLB) surfactants selected from the group consisting of phosphatidylcholine and lecithin.

10. The nanoparticle dispersion of claim 8, further comprising one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80 and one or more phospholipid low hydrophile-lipophile-balance (HLB) surfactants selected from the group consisting of phosphatidylcholine and lecithin.

11. The nanoparticle dispersion of claim 8, further comprising one or more non-polyethoxylated high hydrophile-lipophile-balance (HLB) surfactants selected from the group consisting of cocoglucoside, decyl glucoside, and xylityl caprate/caprylate.

12. The nanoparticle dispersion of claim 8, wherein the nanoparticle dispersion has a weight square mean deviation value of hydrophile-lipophile-balance (HLB) ($WMSD_{HLB}$) between about 1.5 and about 4.5.

13. The nanoparticle dispersion of claim 8, wherein the nanoparticle dispersion has a volume average particle size less than about 150 nm.

14. The nanoparticle dispersion of claim 8, wherein the nanoparticle dispersion has a latent lamellar structure.

15. A nanoparticle dispersion for topical delivery to skin of a mammal, the nanoparticle dispersion comprising;
one or more hydrophobic drugs selected from the group consisting of aspirin, benzocaine, hydrocortisone, and lidocaine;
one or more ether type polyethoxylated high hydrophile-lipophile-balance (HLB) surfactants selected from the group consisting of laureth-23, laureth-30, steareth-100, steareth-20, steareth-40, ceteareth-20, and ceteareth-30;
one or more ester type polyethoxylated high hydrophile-lipophile-balance (HLB) surfactants selected from the group consisting of PEG100 stearate; PEG20 stearate; PEG30 glyceryl cocoate; PEG32 stearate; polysorbate 20, and polysorbate 80;
one or more phospholipid low hydrophile-lipophile-balance (HLB) surfactants selected from the group consisting of phosphatidylcholine and lecithin;
one or more low hydrophile-lipophile-balance (HLB) surfactants selected from the group consisting of stearic acid, sorbitan oleate, and sorbitan stearate;
one or more water immiscible oils selected from the group consisting of cocoyl caprate/caprylate, benzyl alcohol, diisopropyl adipate, capric/caprylic triglyceride oil, isopropyl myristate, limonene, medium chain triglyceride oil, mineral oil, omega 3 fatty acid, oleyl alcohol, sesame oil, and a combination of isohexadecane, isododecane, and a $C_{13-15}$ alkane;
water,
wherein the nanoparticle dispersion has a latent lamellar structure below 40° C., and wherein the one or more hydrophobic drugs each independently having a log P>1 do not form crystals from the nanoparticle dispersion for greater than about 8 months at a temperature from about 18° C. to about 22° C.

16. The nanoparticle dispersion of claim 15, further comprising one or more non-polyethoxylated high hydrophile-lipophile-balance (HLB) surfactants selected from the group consisting of cocoglucoside, decyl glucoside, and xylityl caprate/caprylate.

17. The nanoparticle dispersion of claim 15, wherein the nanoparticle dispersion has a weight square mean deviation value of hydrophile-lipophile-balance (HLB) ($WMSD_{HLB}$) between about 1.5 and about 4.5.

\* \* \* \* \*